(12) United States Patent
Cappello et al.

(10) Patent No.: US 6,380,154 B1
(45) Date of Patent: *Apr. 30, 2002

(54) SYNTHETIC PROTEINS FOR IN VIVO DRUG DELIVERY AND TISSUE AUGMENTATION

(75) Inventors: Joseph Cappello; Erwin R. Stedronsky, both of San Diego, CA (US)

(73) Assignee: Protein Polymer Technologies, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/806,029

(22) Filed: Feb. 24, 1997

Related U.S. Application Data

(63) Continuation-in-part of application No. 08/212,237, filed on Mar. 11, 1994, now Pat. No. 5,606,019.

(51) Int. Cl.[7] .......................... C07K 7/06; A61K 38/00; A61K 38/17
(52) U.S. Cl. ............................ 514/2; 514/17; 530/329; 530/330; 435/69.1; 435/172.3
(58) Field of Search ............... 514/17, 2; 530/329–330; 435/69.1, 172.3

(56) References Cited

U.S. PATENT DOCUMENTS

| | | | |
|---|---|---|---|
| 4,215,200 A | 7/1980 | Miyata et al. | 435/273 |
| 4,589,882 A | 5/1986 | Urry | 623/11 |
| 5,171,505 A | 12/1992 | Lock | 264/202 |
| 5,235,041 A | 8/1993 | Cappello et al. | 530/353 |
| 5,243,038 A | 9/1993 | Ferrari et al. | 536/23.1 |
| 5,523,291 A | * | 6/1996 | Janzen et al. | 514/21 |

FOREIGN PATENT DOCUMENTS

| | | | |
|---|---|---|---|
| WO | 88/01623 | 3/1988 | |
| WO | 88/03533 | 5/1988 | |
| WO | 90/05177 | 5/1990 | |
| WO | 95/23611 | 9/1995 | |
| WO | 95/24478 | * 9/1995 | C12N/15/11 |

OTHER PUBLICATIONS

Cappello et al., "Genetic Engineering of Structural Protein Polymers," *Biotechnol. Prog.*, 6:198–202 (1990).

Cappello, "The Biological Production of Protein Polymers and Their Use," *TIBTECH*, 8:309–311 (1990).

Cappello, "Bioresorption of Implanted Protein Polymer Films Controlled by Adjustment of Their Silk/Elastin Block Lengths," 207th National Meeting of the American Chemical Society, San Diego, Mar. 13–17, vol. 204, No. 82 (1994) (Abstract No. XP000654884).

* cited by examiner

*Primary Examiner*—Bennett Celsa
(74) *Attorney, Agent, or Firm*—Flehr Hohbach Test Albritton & Herbert LLP; Richard F. Trecartin, Esq.

(57) ABSTRACT

Method and compositions are provided which are useful for delivering a biologically active substance to a localized site in vivo and for altering the physical dimensions of a body tissue. These method and compositions employ protein polymers having varying ratios of elastin-like collagen-like, keratin-like repeating units and repeating units which promote protein crystallization such as silk-like repeating units. By varying the length of segments of the repeating units and/or the concentration of the protein polymers in the composition, the rate of delivery of a biologically active substance to a localized site can be greatly varied. Moreover, because the compositions are capable of acquiring a non-liquid form under normal physiological conditions, they find use as biocompatible tissue augmentation products.

10 Claims, 8 Drawing Sheets

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:1:

Gly Ala Gly Ala Gly Ser
1               5

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:2:

Ser Gly Ala Gly Ala Gly
1               5

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:3:

Val Pro Gly Gly
1

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:4:

Ala Pro Gly Val Gly Val
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown

```
        (ii) MOLECULE TYPE: protein (ix) FEATURE:
             (A) NAME/KEY: Modified-site
             (B) LOCATION: 2..3
             (D) OTHER INFORMATION: /note= "The 'xaa' at position 2
                 represents val, lys, his, glu, arg, asp, ser, trp, tyr,
                 phe, leu, glu, asn, cys or met, usually val and lys,
                 preferably val."

(xi) SEQUENCE DESCRIPTION: SEQ ID NO:5:

Gly Xaa Gly Val Pro
1               5

(2) INFORMATION FOR SEQ ID NO:6:

(i) SEQUENCE CHARACTERISTICS:
            (A) LENGTH: 5 amino acids
            (B) TYPE: amino acid
            (C) STRANDEDNESS: unknown
            (D) TOPOLOGY: unknown (ii) MOLECULE TYPE: protein (ix) FEATURE:
             (A) NAME/KEY: Modified-site
             (B) LOCATION: 4..5
             (D) OTHER INFORMATION: /note= "The 'xaa' at position 4
                 represents val, lys, his, glu, arg, asp, ser, trp, tyr,
                 phe, leu, glu, asn, cys or met, usually val and lys,
                 preferably val."

(xi) SEQUENCE DESCRIPTION: SEQ ID NO:6:

Val Pro Gly Xaa Gly
1               5

(2) INFORMATION FOR SEQ ID NO:7:

(i) SEQUENCE CHARACTERISTICS:
            (A) LENGTH: 5 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:7:

Val Pro Gly Val Gly
1               5

(2) INFORMATION FOR SEQ ID NO:8:

(i) SEQUENCE CHARACTERISTICS:
            (A) LENGTH: 5 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:8:

Gly Val Gly Val Pro
1               5

(2) INFORMATION FOR SEQ ID NO:9:

(i) SEQUENCE CHARACTERISTICS:
            (A) LENGTH: 1136 amino acids
            (B) TYPE: amino acid
            (C) STRANDEDNESS: unknown
```

(D) TOPOLOGY: unknown (ii) MOLECULE TYPE: protein (xi) SEQUENCE DESCRIPTION: SEQ ID NO:9:

```
Asp Pro Val Val Leu Gln Arg Arg Asp Trp Glu Asn Pro Gly Val Thr
1               5                   10                  15
Gln Leu Asn Arg Leu Ala Ala His Pro Pro Phe Ala Ser Asp Pro Met
            20                  25                  30
Gly Ala Gly Ser Gly Ala Gly Ala Gly Ser Gly Ala Gly Ala Gly Ser
        35                  40                  45
Gly Ala Gly Ala Gly Ser Gly Ala Gly Ala Gly Ser Gly Ala Gly Ala
    50                  55                  60
Gly Ser Gly Ala Gly Ala Gly Ser Gly Ala Gly Ala Gly Ser Gly Ala
65                  70                  75                  80
Gly Ala Gly Ser Gly Ala Gly Ala Gly Ser Gly Ala Ala Gly Tyr Gly
                85                  90                  95
Ala Gly Ala Gly Ser Gly Ala Gly Ala Gly Ser Gly Ala Gly Ala Gly
            100                 105                 110
Ser Gly Ala Gly Ala Gly Ser Gly Ala Gly Ala Gly Ser Gly Ala Gly
        115                 120                 125
Ala Gly Ser Gly Ala Gly Ala Gly Ser Gly Ala Gly Ala Gly Ser Gly
    130                 135                 140
Ala Gly Ala Gly Ser Gly Ala Ala Gly Tyr Gly Ala Gly Ala Gly Ser
145                 150                 155                 160
Gly Ala Gly Ala Gly Ser Gly Ala Gly Ala Gly Ser Gly Ala Gly Ala
                165                 170                 175
Gly Ser Gly Ala Gly Ala Gly Ser Gly Ala Gly Ala Gly Ser Gly Ala
            180                 185                 190
Gly Ala Gly Ser Gly Ala Gly Ala Gly Ser Gly Ala Gly Ala Gly Ser
        195                 200                 205
Gly Ala Ala Gly Tyr Gly Ala Gly Ala Gly Ser Gly Ala Gly Ala Gly
    210                 215                 220
Ser Gly Ala Gly Ala Gly Ser Gly Ala Gly Ala Gly Ser Gly Ala Gly
225                 230                 235                 240
Ala Gly Ser Gly Ala Gly Ala Gly Ser Gly Ala Gly Ala Gly Ser Gly
                245                 250                 255
Ala Gly Ala Gly Ser Gly Ala Gly Ala Gly Ser Gly Ala Ala Gly Tyr
            260                 265                 270
Gly Ala Gly Ala Gly Ser Gly Ala Gly Ala Gly Ser Gly Ala Gly Ala
        275                 280                 285
Gly Ser Gly Ala Gly Ala Gly Ser Gly Ala Gly Ala Gly Ser Gly Ala
    290                 295                 300
Gly Ala Gly Ser Gly Ala Gly Ala Gly Ser Gly Ala Gly Ala Gly Ser
305                 310                 315                 320
Gly Ala Gly Ala Gly Ser Gly Ala Ala Gly Tyr Gly Ala Gly Ala Gly
                325                 330                 335
Ser Gly Ala Gly Ala Gly Ser Gly Ala Gly Ala Gly Ser Gly Ala Gly
            340                 345                 350
Ala Gly Ser Gly Ala Gly Ala Gly Ser Gly Ala Gly Ala Gly Ser Gly
        355                 360                 365
Ala Gly Ala Gly Ser Gly Ala Gly Ala Gly Ser Gly Ala Gly Ala Gly
    370                 375                 380
Ser Gly Ala Ala Gly Tyr Gly Ala Gly Ala Gly Ser Gly Ala Gly Ala
```

-continued

```
385                 390                 395                 400
Gly Ser Gly Ala Gly Ala Gly Ser Gly Ala Gly Ala Gly Ser Gly Ala
                405                 410                 415
Gly Ala Gly Ser Gly Ala Gly Ala Gly Ser Gly Ala Gly Ala Gly Ser
                420                 425                 430
Gly Ala Gly Ala Gly Ser Gly Ala Gly Ala Gly Ser Gly Ala Ala Gly
                435                 440                 445
Tyr Gly Ala Gly Ala Gly Ser Gly Ala Gly Ala Gly Ser Gly Ala Gly
                450                 455                 460
Ala Gly Ser Gly Ala Gly Ala Gly Ser Gly Ala Gly Ala Gly Ser Gly
465                 470                 475                 480
Ala Gly Ala Gly Ser Gly Ala Gly Ala Gly Ser Gly Ala Gly Ala Gly
                485                 490                 495
Ser Gly Ala Gly Ala Gly Ser Gly Ala Ala Gly Tyr Gly Ala Gly Ala
                500                 505                 510
Gly Ser Gly Ala Gly Ala Gly Ser Gly Ala Gly Ala Gly Ser Gly Ala
                515                 520                 525
Gly Ala Gly Ser Gly Ala Gly Ala Gly Ser Gly Ala Gly Ala Gly Ser
                530                 535                 540
Gly Ala Gly Ala Gly Ser Gly Ala Gly Ala Gly Ser Gly Ala Gly Ala
545                 550                 555                 560
Gly Ser Gly Ala Ala Gly Tyr Gly Ala Gly Ala Gly Ser Gly Ala Gly
                565                 570                 575
Ala Gly Ser Gly Ala Gly Ala Gly Ser Gly Ala Gly Ala Gly Ser Gly
                580                 585                 590
Ala Gly Ala Gly Ser Gly Ala Gly Ala Gly Ser Gly Ala Gly Ala Gly
                595                 600                 605
Ser Gly Ala Gly Ala Gly Ser Gly Ala Gly Ala Gly Ser Gly Ala Ala
                610                 615                 620
Gly Tyr Gly Ala Gly Ala Gly Ser Gly Ala Gly Ala Gly Ser Gly Ala
625                 630                 635                 640
Gly Ala Gly Ser Gly Ala Gly Ala Gly Ser Gly Ala Gly Ala Gly Ser
                645                 650                 655
Gly Ala Gly Ala Gly Ser Gly Ala Gly Ala Gly Ser Gly Ala Gly Ala
                660                 665                 670
Gly Ser Gly Ala Gly Ala Gly Ser Gly Ala Ala Gly Tyr Gly Ala Gly
                675                 680                 685
Ala Gly Ser Gly Ala Gly Ala Gly Ser Gly Ala Gly Ala Gly Ser Gly
                690                 695                 700
Ala Gly Ala Gly Ser Gly Ala Gly Ala Gly Ser Gly Ala Gly Ala Gly
705                 710                 715                 720
Ser Gly Ala Gly Ala Gly Ser Gly Ala Gly Ala Gly Ser Gly Ala Gly
                725                 730                 735
Ala Gly Ser Gly Ala Ala Gly Tyr Gly Ala Gly Ala Gly Ser Gly Ala
                740                 745                 750
Gly Ala Gly Ser Gly Ala Gly Ala Gly Ser Gly Ala Gly Ala Gly Ser
                755                 760                 765
Gly Ala Gly Ala Gly Ser Gly Ala Gly Ala Gly Ser Gly Ala Gly Ala
                770                 775                 780
Gly Ser Gly Ala Gly Ala Gly Ser Gly Ala Gly Ala Gly Ser Gly Ala
785                 790                 795                 800
Ala Gly Tyr Gly Ala Gly Ala Gly Ser Gly Ala Gly Ala Gly Ser Gly
                805                 810                 815
```

```
Ala Gly Ala Gly Ser Gly Ala Gly Ser Gly Ala Gly
            820             825             830

Ser Gly Ala Gly Ala Ser Gly Ala Gly Ala Gly Ser Gly Ala Gly
            835             840             845

Ala Gly Ser Gly Ala Gly Ala Gly Ser Gly Ala Ala Gly Tyr Gly Ala
            850             855             860

Gly Ala Gly Ser Gly Ala Gly Ala Gly Ser Gly Ala Gly Ala Gly Ser
865             870             875             880

Gly Ala Gly Ala Gly Ser Gly Ala Gly Ala Gly Ser Gly Ala Gly Ala
            885             890             895

Gly Ser Gly Ala Gly Ala Gly Ser Gly Ala Gly Ala Gly Ser Gly Ala
            900             905             910

Gly Ala Gly Ser Gly Ala Ala Gly Tyr Gly Ala Gly Ala Gly Ser Gly
            915             920             925

Ala Gly Ala Gly Ser Gly Ala Gly Ala Gly Ser Gly Ala Gly Ala Gly
            930             935             940

Ser Gly Ala Gly Ala Gly Ser Gly Ala Gly Ala Gly Ser Gly Ala Gly
945             950             955             960

Ala Gly Ser Gly Ala Gly Ala Gly Ser Gly Ala Gly Ala Gly Ser Gly
            965             970             975

Ala Ala Gly Tyr Gly Ala Gly Ala Gly Ser Gly Ala Gly Ala Gly Ser
            980             985             990

Gly Ala Gly Ala Gly Ser Gly Ala Gly Ala Gly Ser Gly Ala Gly Ala
            995             1000            1005

Gly Ser Gly Ala Gly Ala Gly Ser Gly Ala Gly Ala Gly Ser Gly Ala
            1010            1015            1020

Gly Ala Gly Ser Gly Ala Gly Ala Gly Ser Gly Ala Ala Gly Tyr Gly
1025            1030            1035            1040

Ala Gly Ala Gly Ser Gly Ala Gly Ala Gly Ser Gly Ala Gly Ala Gly
            1045            1050            1055

Ser Gly Ala Gly Ala Gly Ser Gly Ala Gly Ala Gly Ser Gly Ala Gly
            1060            1065            1070

Ala Gly Ser Gly Ala Gly Ala Gly Ser Gly Ala Gly Ala Gly Ser Gly
            1075            1080            1085

Ala Gly Ala Gly Ser Gly Ala Ala Gly Tyr Gly Ala Gly Ala Gly Ser
            1090            1095            1100

Gly Ala Gly Ala Gly Ser Gly Ala Gly Ala Met Asp Pro Gly Arg Tyr
1105            1110            1115            1120

Gln Leu Ser Ala Gly Arg Tyr His Tyr Gln Leu Val Trp Cys Gln Lys
                1125            1130            1135

(2) INFORMATION FOR SEQ ID NO:10:

(i) SEQUENCE CHARACTERISTICS:
        (A) LENGTH: 1059 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:10:

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30
```

Met Gly Ala Gly Ser Gly Ala Gly Ser Gly Ala Gly
    35              40              45

Ser Gly Ala Gly Ala Gly Ser Gly Ala Gly Ser Gly Ala Gly
50              55              60

Ala Gly Ser Gly Ala Gly Ala Gly Ser Gly Ala Gly Ser Gly
65              70              75              80

Ala Gly Ala Gly Ser Gly Ala Gly Ala Gly Ser Gly Ala Gly
            85              90              95

Ser Gly Ala Gly Ala Gly Ser Gly Ala Gly Ala Gly Ser Gly Ala Gly
        100             105             110

Ala Gly Ser Gly Ala Gly Ala Gly Ser Gly Ala Gly Ser Gly
        115             120             125

Ala Gly Ala Gly Ser Gly Ala Gly Ala Gly Ser Gly Ala Gly
    130             135             140

Ser Gly Ala Gly Ala Gly Ser Gly Ala Gly Ala Gly Ser Gly Ala Gly
145             150             155             160

Ala Gly Ser Gly Ala Gly Ala Gly Ser Gly Ala Gly Ser Gly
        165             170             175

Ala Gly Ala Gly Ser Gly Ala Gly Ala Gly Ser Gly Ala Gly
        180             185             190

Ser Gly Ala Gly Ala Gly Ser Gly Ala Gly Ala Gly Ser Gly Ala Gly
        195             200             205

Ala Gly Ser Gly Ala Gly Ala Gly Ser Gly Ala Gly Ser Gly
    210             215             220

Ala Gly Ala Gly Ser Gly Ala Gly Ala Gly Ser Gly Ala Gly
225             230             235             240

Ser Gly Ala Gly Ala Gly Ser Gly Ala Gly Ala Gly Ser Gly Ala Gly
            245             250             255

Ala Gly Ser Gly Ala Gly Ala Gly Ser Gly Ala Gly Ser Gly
        260             265             270

Ala Gly Ala Gly Ser Gly Ala Gly Ala Gly Ser Gly Ala Gly
        275             280             285

Ser Gly Ala Gly Ala Gly Ser Gly Ala Gly Ala Gly Ser Gly Ala Gly
        290             295             300

Ala Gly Ser Gly Ala Gly Ala Gly Ser Gly Ala Gly Ser Gly
305             310             315             320

Ala Gly Ala Gly Ser Gly Ala Gly Ala Gly Ser Gly Ala Gly
            325             330             335

Ser Gly Ala Gly Ala Gly Ser Gly Ala Gly Ala Gly Ser Gly Ala Gly
        340             345             350

Ala Gly Ser Gly Ala Gly Ala Gly Ser Gly Ala Gly Ser Gly
        355             360             365

Ala Gly Ala Gly Ser Gly Ala Gly Ala Gly Ser Gly Ala Gly
    370             375             380

Ser Gly Ala Gly Ala Gly Ser Gly Ala Gly Ala Gly Ser Gly Ala Gly
385             390             395             400

Ala Gly Ser Gly Ala Gly Ala Gly Ser Gly Ala Gly Ser Gly
        405             410             415

Ala Gly Ala Gly Ser Gly Ala Gly Ala Gly Ser Gly Ala Gly
        420             425             430

Ser Gly Ala Gly Ala Gly Ser Gly Ala Gly Ala Gly Ser Gly Ala Gly
        435             440             445

-continued

```
Ala Gly Ser Gly Ala Gly Ala Gly Ser Gly Ala Gly Ala Gly Ser Gly
    450                 455                 460
Ala Gly Ala Gly Ser Gly Ala Gly Ala Gly Ser Gly Ala Gly Ala Gly
465                 470                 475                 480
Ser Gly Ala Gly Ala Gly Ser Gly Ala Gly Ala Gly Ser Gly Ala Gly
            485                 490                 495
Ala Gly Ser Gly Ala Gly Ala Gly Ser Gly Ala Gly Ala Gly Ser Gly
        500                 505                 510
Ala Gly Ala Gly Ser Gly Ala Gly Ala Gly Ser Gly Ala Gly Ala Gly
    515                 520                 525
Ser Gly Ala Gly Ala Gly Ser Gly Ala Gly Ala Gly Ser Gly Ala Gly
530                 535                 540
Ala Gly Ser Gly Ala Gly Ala Gly Ser Gly Ala Gly Ala Gly Ser Gly
545                 550                 555                 560
Ala Gly Ala Gly Ser Gly Ala Gly Ala Gly Ser Gly Ala Gly Ala Gly
            565                 570                 575
Ser Gly Ala Gly Ala Gly Ser Gly Ala Gly Ala Gly Ser Gly Ala Gly
        580                 585                 590
Ala Gly Ser Gly Ala Gly Ala Gly Ser Gly Ala Gly Ala Gly Ser Gly
    595                 600                 605
Ala Gly Ala Gly Ser Gly Ala Gly Ala Gly Ser Gly Ala Gly Ala Gly
    610                 615                 620
Ser Gly Ala Gly Ala Gly Ser Gly Ala Gly Ala Gly Ser Gly Ala Gly
625                 630                 635                 640
Ala Gly Ser Gly Ala Gly Ala Gly Ser Gly Ala Gly Ala Gly Ser Gly
            645                 650                 655
Ala Gly Ala Gly Ser Gly Ala Gly Ala Gly Ser Gly Ala Gly Ala Gly
        660                 665                 670
Ser Gly Ala Gly Ala Gly Ser Gly Ala Gly Ala Gly Ser Gly Ala Gly
    675                 680                 685
Ala Gly Ser Gly Ala Gly Ala Gly Ser Gly Ala Gly Ala Gly Ser Gly
    690                 695                 700
Ala Gly Ala Gly Ser Gly Ala Gly Ala Gly Ser Gly Ala Gly Ala Gly
705                 710                 715                 720
Ser Gly Ala Gly Ala Gly Ser Gly Ala Gly Ala Gly Ser Gly Ala Gly
            725                 730                 735
Ala Gly Ser Gly Ala Gly Ala Gly Ser Gly Ala Gly Ala Gly Ser Gly
        740                 745                 750
Ala Gly Ala Gly Ser Gly Ala Gly Ala Gly Ser Gly Ala Gly Ala Gly
    755                 760                 765
Ser Gly Ala Gly Ala Gly Ser Gly Ala Gly Ala Gly Ser Gly Ala Gly
770                 775                 780
Ala Gly Ser Gly Ala Gly Ala Gly Ser Gly Ala Gly Ala Gly Ser Gly
785                 790                 795                 800
Ala Gly Ala Gly Ser Gly Ala Gly Ala Gly Ser Gly Ala Gly Ala Gly
            805                 810                 815
Ser Gly Ala Gly Ala Gly Ser Gly Ala Gly Ala Gly Ser Gly Ala Gly
        820                 825                 830
Ala Gly Ser Gly Ala Gly Ala Gly Ser Gly Ala Gly Ala Gly Ser Gly
    835                 840                 845
Ala Gly Ala Gly Ser Gly Ala Gly Ala Gly Ser Gly Ala Gly Ala Gly
    850                 855                 860
Ser Gly Ala Gly Ala Gly Ser Gly Ala Gly Ala Gly Ser Gly Ala Gly
```

```
                     865                 870                 875                 880
Ala Gly Ser Gly Ala Gly Ala Gly Ser Gly Ala Gly Ala Gly Ser Gly
                    885                 890                 895
Ala Gly Ala Gly Ser Gly Ala Gly Ala Gly Ser Gly Ala Gly Ala Gly
                900                 905                 910
Ser Gly Ala Gly Ala Gly Ser Gly Ala Gly Ala Gly Ser Gly Ala Gly
            915                 920                 925
Ala Gly Ser Gly Ala Gly Ala Gly Ser Gly Ala Gly Ala Gly Ser Gly
        930                 935                 940
Ala Gly Ala Gly Ser Gly Ala Gly Ala Gly Ser Gly Ala Gly Ala Gly
945                 950                 955                 960
Ser Gly Ala Gly Ala Gly Ser Gly Ala Gly Ala Gly Ser Gly Ala Gly
                965                 970                 975
Ala Gly Ser Gly Ala Gly Ala Gly Ser Gly Ala Gly Ala Gly Ser Gly
            980                 985                 990
Ala Gly Ala Gly Ser Gly Ala Gly Ala Gly Ser Gly Ala Gly Ala Gly
        995                 1000                1005
Ser Gly Ala Gly Ala Gly Ser Gly Ala Gly Ala Gly Ser Gly Ala Gly
    1010                1015                1020
Ala Gly Ser Gly Ala Gly Ala Gly Ser Gly Ala Gly Ala Met Asp Pro
1025                1030                1035                1040
Gly Arg Tyr Gln Leu Ser Ala Gly Arg Tyr His Tyr Gln Leu Val Trp
                1045                1050                1055
Cys Gln Lys
```

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:11:

```
Gly Lys Gly Val Pro
1               5
```

(2) INFORMATION FOR SEQ ID NO:12:

(i) SEQUENCE CHARACTERISTICS:
        (A) LENGTH: 384 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..384

(xi) SEQUENCE DESCRIPTION: SEQ ID NO:12:

```
GGT GCC GGC AGC GGT GCA GGA GCC GGT TCT GGA GCT GGC GCG GGC TCT      48
Gly Ala Gly Ser Gly Ala Gly Ala Gly Ser Gly Ala Gly Ala Gly Ser
1               5                   10                  15

GGA GTA GGT GTG CCA GGT GTA GGA GTT CCG GGT GTA GGC GTT CCG GGA      96
Gly Val Gly Val Pro Gly Val Gly Val Pro Gly Val Gly Val Pro Gly
            20                  25                  30

GTT GGT GTA CCT GGA GTG GGT GTT CCA GGC GTA GGT GTG CCC GGG GTA     144
```

```
Val Gly Val Pro Gly Val Gly Val Pro Gly Val Gly Val Pro Gly Val
            35                  40                  45

GGC GTT CCG GGA GTA GGG GTG CCA GGT GTA GGA GTT CCG GGT GTA GGC        192
Gly Val Pro Gly Val Gly Val Pro Gly Val Gly Val Pro Gly Val Gly
         50                  55                  60

GTT CCC GGG GTA GGC GTT CCG GGA GTA GGG GTG CCA GGT GTA GGA GTT        240
Val Pro Gly Val Gly Val Pro Gly Val Gly Val Pro Gly Val Gly Val
 65                  70                  75                  80

CCG GGT GTA GGC GTT CCC GGG GTA GGA GTA CCA GGG GTA GGC GTC CCT        288
Pro Gly Val Gly Val Pro Gly Val Gly Val Pro Gly Val Gly Val Pro
                 85                  90                  95

GGA GCG GGT GCT GGT AGC GGC GCA GGC GCG GGC TCT GGC GCG GGC GCA        336
Gly Ala Gly Ala Gly Ser Gly Ala Gly Ala Gly Ser Gly Ala Gly Ala
            100                 105                 110

GGA TCC GGC GCA GGC GCT GGC TCA GGT GCT GGA GCA GGA AGC GGA GCG        384
Gly Ser Gly Ala Gly Ala Gly Ser Gly Ala Gly Ala Gly Ser Gly Ala
         115                 120                 125
```

(2) INFORMATION FOR SEQ ID NO:13:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:13:

```
Gly Ala Gly Ser Gly Ala Gly Ala Gly Ser Gly Ala Gly Ala Gly Ser
 1               5                  10                  15

Gly Val Gly Val Pro Gly Val Gly Val Pro Gly Val Gly Val Pro Gly
            20                  25                  30

Val Gly Val Pro Gly Val Gly Val Pro Gly Val Gly Val Pro Gly Val
         35                  40                  45

Gly Val Pro Gly Val Gly Val Pro Gly Val Gly Val Pro Gly Val Gly
     50                  55                  60

Val Pro Gly Val Gly Val Pro Gly Val Gly Val Pro Gly Val Gly Val
 65                  70                  75                  80

Pro Gly Val Gly Val Pro Gly Val Gly Val Pro Gly Val Gly Val Pro
                 85                  90                  95

Gly Ala Gly Ala Gly Ser Gly Ala Gly Ala Gly Ser Gly Ala Gly Ala
            100                 105                 110

Gly Ser Gly Ala Gly Ala Gly Ser Gly Ala Gly Ala Gly Ser Gly Ala
         115                 120                 125
```

(2) INFORMATION FOR SEQ ID NO:14:

(i) SEQUENCE CHARACTERISTICS:
        (A) LENGTH: 953 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:14:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
```

-continued

```
                35                  40                  45
Ser Gly Val Gly Val Pro Gly Val Gly Val Pro Gly Val Gly Val Pro
 50                  55                  60
Gly Val Gly Val Pro Gly Val Gly Val Pro Gly Val Gly Val Pro Gly
 65                  70                  75                  80
Val Gly Val Pro Gly Val Gly Val Pro Gly Val Gly Val Pro Gly Val
                 85                  90                  95
Gly Val Pro Gly Val Gly Val Pro Gly Val Gly Val Pro Gly Val Gly
                100                 105                 110
Val Pro Gly Val Gly Val Pro Gly Val Gly Val Pro Gly Val Gly Val
                115                 120                 125
Pro Gly Ala Gly Ala Gly Ser Gly Ala Gly Ala Gly Ser Gly Ala Gly
130                 135                 140
Ala Gly Ser Gly Ala Gly Ala Gly Ser Gly Ala Gly Ala Gly Ser Gly
145                 150                 155                 160
Ala Gly Ala Gly Ser Gly Ala Gly Ala Gly Ser Gly Ala Gly Ala Gly
                165                 170                 175
Ser Gly Val Gly Val Pro Gly Val Gly Val Pro Gly Val Gly Val Pro
                180                 185                 190
Gly Val Gly Val Pro Gly Val Gly Val Pro Gly Val Gly Val Pro Gly
                195                 200                 205
Val Gly Val Pro Gly Val Gly Val Pro Gly Val Gly Val Pro Gly Val
                210                 215                 220
Gly Val Pro Gly Val Gly Val Pro Gly Val Gly Val Pro Gly Val Gly
225                 230                 235                 240
Val Pro Gly Val Gly Val Pro Gly Val Gly Val Pro Gly Val Gly Val
                245                 250                 255
Pro Gly Ala Gly Ala Gly Ser Gly Ala Gly Ala Gly Ser Gly Ala Gly
                260                 265                 270
Ala Gly Ser Gly Ala Gly Ala Gly Ser Gly Ala Gly Ala Gly Ser Gly
                275                 280                 285
Ala Gly Ala Gly Ser Gly Ala Gly Ala Gly Ser Gly Ala Gly Ala Gly
                290                 295                 300
Ser Gly Val Gly Val Pro Gly Val Gly Val Pro Gly Val Gly Val Pro
305                 310                 315                 320
Gly Val Gly Val Pro Gly Val Gly Val Pro Gly Val Gly Val Pro Gly
                325                 330                 335
Val Gly Val Pro Gly Val Gly Val Pro Gly Val Gly Val Pro Gly Val
                340                 345                 350
Gly Val Pro Gly Val Gly Val Pro Gly Val Gly Val Pro Gly Val Gly
                355                 360                 365
Val Pro Gly Val Gly Val Pro Gly Val Gly Val Pro Gly Val Gly Val
                370                 375                 380
Pro Gly Ala Gly Ala Gly Ser Gly Ala Gly Ala Gly Ser Gly Ala Gly
385                 390                 395                 400
Ala Gly Ser Gly Ala Gly Ala Gly Ser Gly Ala Gly Ala Gly Ser Gly
                405                 410                 415
Ala Gly Ala Gly Ser Gly Ala Gly Ala Gly Ser Gly Ala Gly Ala Gly
                420                 425                 430
Ser Gly Val Gly Val Pro Gly Val Gly Val Pro Gly Val Gly Val Pro
                435                 440                 445
Gly Val Gly Val Pro Gly Val Gly Val Pro Gly Val Gly Val Pro Gly
                450                 455                 460
```

-continued

Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Val Gly
                485                 490                 495

Val Pro Gly Val Gly Val Pro Gly Val Gly Val Pro Gly Val Gly Val
            500                 505                 510

Pro Gly Ala Gly Ala Gly Ser Gly Ala Gly Ala Gly Ser Gly Ala Gly
        515                 520                 525

Ala Gly Ser Gly Ala Gly Ala Gly Ser Gly Ala Gly Ala Gly Ser Gly
    530                 535                 540

Ala Gly Ala Gly Ser Gly Ala Gly Ala Gly Ser Gly Ala Gly Ala Gly
545                 550                 555                 560

Ser Gly Val Gly Val Pro Gly Val Gly Val Pro Gly Val Gly Val Pro
                565                 570                 575

Gly Val Gly Val Pro Gly Val Gly Val Pro Gly Val Gly Val Pro Gly
            580                 585                 590

Val Gly Val Pro Gly Val Gly Val Pro Gly Val Gly Val Pro Gly Val
        595                 600                 605

Gly Val Pro Gly Val Gly Val Pro Gly Val Gly Val Pro Gly Val Gly
    610                 615                 620

Val Pro Gly Val Gly Val Pro Gly Val Gly Val Pro Gly Val Gly Val
625                 630                 635                 640

Pro Gly Ala Gly Ala Gly Ser Gly Ala Gly Ala Gly Ser Gly Ala Gly
                645                 650                 655

Ala Gly Ser Gly Ala Gly Ala Gly Ser Gly Ala Gly Ala Gly Ser Gly
            660                 665                 670

Ala Gly Ala Gly Ser Gly Ala Gly Ala Gly Ser Gly Ala Gly Ala Gly
        675                 680                 685

Ser Gly Val Gly Val Pro Gly Val Gly Val Pro Gly Val Gly Val Pro
    690                 695                 700

Gly Val Gly Val Pro Gly Val Gly Val Pro Gly Val Gly Val Pro Gly
705                 710                 715                 720

Val Gly Val Pro Gly Val Gly Val Pro Gly Val Gly Val Pro Gly Val
                725                 730                 735

Gly Val Pro Gly Val Gly Val Pro Gly Val Gly Val Pro Gly Val Gly
            740                 745                 750

Val Pro Gly Val Gly Val Pro Gly Val Gly Val Pro Gly Val Gly Val
        755                 760                 765

Pro Gly Ala Gly Ala Gly Ser Gly Ala Gly Ala Gly Ser Gly Ala Gly
    770                 775                 780

Ala Gly Ser Gly Ala Gly Ala Gly Ser Gly Ala Gly Ala Gly Ser Gly
785                 790                 795                 800

Ala Gly Ala Gly Ser Gly Ala Gly Ala Gly Ser Gly Ala Gly Ala Gly
                805                 810                 815

Ser Gly Val Gly Val Pro Gly Val Gly Val Pro Gly Val Gly Val Pro
            820                 825                 830

Gly Val Gly Val Pro Gly Val Gly Val Pro Gly Val Gly Val Pro Gly
        835                 840                 845

Val Gly Val Pro Gly Val Gly Val Pro Gly Val Gly Val Pro Gly Val
    850                 855                 860

Gly Val Pro Gly Val Gly Val Pro Gly Val Gly Val Pro Gly Val Gly
865                 870                 875                 880

```
Val Pro Gly Val Gly Val Pro Gly Val Gly Val Pro Gly Val Gly Val
            885                 890                 895

Pro Gly Ala Gly Ala Gly Ser Gly Ala Gly Ser Gly Ala Gly
        900                 905                 910

Ala Gly Ser Gly Ala Gly Ala Gly Ser Gly Ala Gly Ala Gly Ser Gly
        915                 920                 925

Ala Gly Ala Met Asp Pro Gly Arg Tyr Gln Leu Ser Ala Gly Arg Tyr
        930                 935                 940

His Tyr Gln Leu Val Trp Cys Gln Lys
945                 950
```

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:15:

```
CTGGAGCGGG AGCCTGCATG TACATCCGAG T                                31
```

(2) INFORMATION FOR SEQ ID NO:16:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:16:

```
ACTCGGATGT ACATGCAGGC ACCCGCTCCA GAGC                             34
```

(2) INFORMATION FOR SEQ ID NO:17:

(i) SEQUENCE CHARACTERISTICS:
        (A) LENGTH: 192 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..192

(xi) SEQUENCE DESCRIPTION: SEQ ID NO:17:

```
GGT GCC GGT TCT GGA GCT GGC GCG GGC TCT GGA GTA GGT GTG CCA GGT     48
Gly Ala Gly Ser Gly Ala Gly Ala Gly Ser Gly Val Gly Val Pro Gly
  1               5                  10                  15

GTA GGA GTT CCG GGT GTA GGC GTT CCG GGA GTT GGT GTA CCT GGA GTG     96
Val Gly Val Pro Gly Val Gly Val Pro Gly Val Gly Val Pro Gly Val
                 20                  25                  30

GGT GTT CCA GGC GTA GGT GTG CCC GGG GTA GGA GTA CCA GGG GTA GGC    144
Gly Val Pro Gly Val Gly Val Pro Gly Val Gly Val Pro Gly Val Gly
             35                  40                  45

GTC CCT GGA GCG GGT GCT GGT AGC GGC GCA GGC GCG GGC TCT GGA GCG    192
Val Pro Gly Ala Gly Ala Gly Ser Gly Ala Gly Ala Gly Ser Gly Ala
         50                  55                  60
```

(2) INFORMATION FOR SEQ ID NO:18:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO:18:

```
Gly Ala Gly Ser Gly Ala Gly Ala Gly Ser Gly Val Gly Val Pro Gly
 1               5                  10                  15

Val Gly Val Pro Gly Val Gly Val Pro Gly Val Gly Val Pro Gly Val
             20                  25                  30

Gly Val Pro Gly Val Gly Val Pro Gly Val Gly Val Pro Gly Val Gly
         35                  40                  45

Val Pro Gly Ala Gly Ala Gly Ser Gly Ala Gly Ala Gly Ser Gly Ala
     50                  55                  60
```

(2) INFORMATION FOR SEQ ID NO:19:

(i) SEQUENCE CHARACTERISTICS:
        (A) LENGTH: 889 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:19:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
             20                  25                  30

Met Gly Ala Gly Ser Gly Ala Gly Ala Gly Ser Gly Val Gly Val Pro
         35                  40                  45

Gly Val Gly Val Pro Gly Val Gly Val Pro Gly Val Gly Val Pro Gly
     50                  55                  60

Val Gly Val Pro Gly Val Gly Val Pro Gly Val Gly Val Pro Gly Val
65                   70                  75                  80

Gly Val Pro Gly Ala Gly Ala Gly Ser Gly Ala Gly Ala Gly Ser Gly
             85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
            115                 120                 125

Val Gly Val Pro Gly Val Gly Val Pro Gly Val Gly Val Pro Gly Val
            130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
            165                 170                 175

Gly Val Gly Val Pro Gly Val Gly Val Pro Gly Val Gly Val Pro Gly
            180                 185                 190

Val Gly Val Pro Gly Val Gly Val Pro Gly Val Gly Val Pro Gly Val
            195                 200                 205

Gly Val Pro Gly Ala Gly Ala Gly Ser Gly Ala Gly Ala Gly Ser Gly
            210                 215                 220

Ala Gly Ala Gly Ser Gly Ala Gly Ala Gly Ser Gly Val Gly Val Pro
```

```
                225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Val Pro Gly Val
                260                 265                 270
Gly Val Pro Gly Ala Gly Ala Gly Ser Gly Ala Gly Ala Gly Ser Gly
                275                 280                 285
Ala Gly Ala Gly Ser Gly Ala Gly Ala Gly Ser Gly Val Gly Val Pro
                290                 295                 300
Gly Val Gly Val Pro Gly Val Gly Val Pro Gly Val Gly Val Pro Gly
305                 310                 315                 320
Val Gly Val Pro Gly Val Gly Val Pro Gly Val Gly Val Pro Gly Val
                325                 330                 335
Gly Val Pro Gly Ala Gly Ala Gly Ser Gly Ala Gly Ala Gly Ser Gly
                340                 345                 350
Ala Gly Ala Gly Ser Gly Ala Gly Ala Gly Ser Gly Val Gly Val Pro
                355                 360                 365
Gly Val Gly Val Pro Gly Val Gly Val Pro Gly Val Gly Val Pro Gly
                370                 375                 380
Val Gly Val Pro Gly Val Gly Val Pro Gly Val Gly Val Pro Gly Val
385                 390                 395                 400
Gly Val Pro Gly Ala Gly Ala Gly Ser Gly Ala Gly Ala Gly Ser Gly
                405                 410                 415
Ala Gly Ala Gly Ser Gly Ala Gly Ala Gly Ser Gly Val Gly Val Pro
                420                 425                 430
Gly Val Gly Val Pro Gly Val Gly Val Pro Gly Val Gly Val Pro Gly
                435                 440                 445
Val Gly Val Pro Gly Val Gly Val Pro Gly Val Gly Val Pro Gly Val
                450                 455                 460
Gly Val Pro Gly Ala Gly Ala Gly Ser Gly Ala Gly Ala Gly Ser Gly
465                 470                 475                 480
Ala Gly Ala Gly Ser Gly Ala Gly Ala Gly Ser Gly Val Gly Val Pro
                485                 490                 495
Gly Val Gly Val Pro Gly Val Gly Val Pro Gly Val Gly Val Pro Gly
                500                 505                 510
Val Gly Val Pro Gly Val Gly Val Pro Gly Val Gly Val Pro Gly Val
                515                 520                 525
Gly Val Pro Gly Ala Gly Ala Gly Ser Gly Ala Gly Ala Gly Ser Gly
                530                 535                 540
Ala Gly Ala Gly Ser Gly Ala Gly Ala Gly Ser Gly Val Gly Val Pro
545                 550                 555                 560
Gly Val Gly Val Pro Gly Val Gly Val Pro Gly Val Gly Val Pro Gly
                565                 570                 575
Val Gly Val Pro Gly Val Gly Val Pro Gly Val Gly Val Pro Gly Val
                580                 585                 590
Gly Val Pro Gly Ala Gly Ala Gly Ser Gly Ala Gly Ala Gly Ser Gly
                595                 600                 605
Ala Gly Ala Gly Ser Gly Ala Gly Ala Gly Ser Gly Val Gly Val Pro
                610                 615                 620
Gly Val Gly Val Pro Gly Val Gly Val Pro Gly Val Gly Val Pro Gly
625                 630                 635                 640
Val Gly Val Pro Gly Val Gly Val Pro Gly Val Gly Val Pro Gly Val
                645                 650                 655
```

```
Gly Val Pro Gly Ala Gly Ala Gly Ser Gly Ala Gly Ala Gly Ser Gly
            660                 665                 670

Ala Gly Ala Gly Ser Gly Ala Gly Ala Gly Ser Gly Val Gly Val Pro
            675                 680                 685

Gly Val Gly Val Pro Gly Val Gly Val Pro Gly Val Gly Val Pro Gly
            690                 695                 700

Val Gly Val Pro Gly Val Gly Val Pro Gly Val Gly Val Pro Gly Val
705                 710                 715                 720

Gly Val Pro Gly Ala Gly Ala Gly Ser Gly Ala Gly Ala Gly Ser Gly
            725                 730                 735

Ala Gly Ala Gly Ser Gly Ala Gly Ala Gly Ser Gly Val Gly Val Pro
            740                 745                 750

Gly Val Gly Val Pro Gly Val Gly Val Pro Gly Val Gly Val Pro Gly
            755                 760                 765

Val Gly Val Pro Gly Val Gly Val Pro Gly Val Gly Val Pro Gly Val
            770                 775                 780

Gly Val Pro Gly Ala Gly Ala Gly Ser Gly Ala Gly Ala Gly Ser Gly
785                 790                 795                 800

Ala Gly Ala Gly Ser Gly Ala Gly Ala Gly Ser Gly Val Gly Val Pro
            805                 810                 815

Gly Val Gly Val Pro Gly Val Gly Val Pro Gly Val Gly Val Pro Gly
            820                 825                 830

Val Gly Val Pro Gly Val Gly Val Pro Gly Val Gly Val Pro Gly Val
            835                 840                 845

Gly Val Pro Gly Ala Gly Ala Gly Ser Gly Ala Gly Ala Gly Ser Gly
            850                 855                 860

Ala Gly Ala Met Asp Pro Gly Arg Tyr Gln Leu Ser Ala Gly Arg Tyr
865                 870                 875                 880

His Tyr Gln Leu Val Trp Cys Gln Lys
            885

(2) INFORMATION FOR SEQ ID NO:20:

(i) SEQUENCE CHARACTERISTICS:
        (A) LENGTH: 93 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:20:

ATGGCAGCGA AAGGGGACCG GTGCCGGCGC AGGTAGCGGA GCCGGTGCGG GCTCAAAAAG      60

GGCTCTGGTG CCTTTCCGCT AAAGTCCTGC CGT                                  93

(2) INFORMATION FOR SEQ ID NO:21:

(i) SEQUENCE CHARACTERISTICS:
        (A) LENGTH: 35 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:21:

AAGAAGGAGA TATCATATGG CAGCGAAAGG GGACC                                35
```

(2) INFORMATION FOR SEQ ID NO:22:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:22:

CGCAGATCTT TAAATTACGG CAGGACTTTA GCGGAAA                    37

(2) INFORMATION FOR SEQ ID NO:23:

(i) SEQUENCE CHARACTERISTICS:
        (A) LENGTH: 180 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..180

(xi) SEQUENCE DESCRIPTION: SEQ ID NO:23:

```
GGT GCC GGT GCG GGC TCT GGT GTT GGA GTG CCA GGT GTC GGT GTT CCG        48
Gly Ala Gly Ala Gly Ser Gly Val Gly Val Pro Gly Val Gly Val Pro
 1               5                  10                  15

GGT GTA GGC GTT CCG GGA GTT GGT GTA CCT GGA AAA GGT GTT CCG GGG        96
Gly Val Gly Val Pro Gly Val Gly Val Pro Gly Lys Gly Val Pro Gly
                20                  25                  30

GTA GGT GTG CCG GGC GTT GGA GTA CCA GGT GTA GGC GTC CCG GGA GCG       144
Val Gly Val Pro Gly Val Gly Val Pro Gly Val Gly Val Pro Gly Ala
            35                  40                  45

GGT GCT GGT AGC GGC GCA GGC GCG GGC TCT GGT GCA                       180
Gly Ala Gly Ser Gly Ala Gly Ala Gly Ser Gly Ala
        50                  55                  60
```

(2) INFORMATION FOR SEQ ID NO:24:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:24:

```
Gly Ala Gly Ala Gly Ser Gly Val Gly Val Pro Gly Val Gly Val Pro
 1               5                  10                  15

Gly Val Gly Val Pro Gly Val Gly Val Pro Gly Lys Gly Val Pro Gly
                20                  25                  30

Val Gly Val Pro Gly Val Gly Val Pro Gly Val Gly Val Pro Gly Ala
            35                  40                  45

Gly Ala Gly Ser Gly Ala Gly Ala Gly Ser Gly Ala
        50                  55                  60
```

(2) INFORMATION FOR SEQ ID NO:25:

(i) SEQUENCE CHARACTERISTICS:
        (A) LENGTH: 750 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:25:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Val Gly Val Pro Gly Val Gly Val
        35                  40                  45

Pro Gly Val Gly Val Pro Gly Val Gly Val Pro Gly Lys Gly Val Pro
    50                  55                  60

Gly Val Gly Val Pro Gly Val Gly Val Pro Gly Val Gly Val Pro Gly
65                  70                  75                  80

Ala Gly Ala Gly Ser Gly Ala Gly Ala Gly Ser Gly Ala Gly Ala Gly
                85                  90                  95

Ser Gly Val Gly Val Pro Gly Val Gly Val Pro Gly Val Gly Val Pro
            100                 105                 110

Gly Val Gly Val Pro Gly Lys Gly Val Pro Gly Val Gly Val Pro Gly
        115                 120                 125

Val Gly Val Pro Gly Val Gly Val Pro Gly Ala Gly Ala Gly Ser Gly
130                 135                 140

Ala Gly Ala Gly Ser Gly Ala Gly Ala Gly Ser Gly Val Gly Val Pro
145                 150                 155                 160

Gly Val Gly Val Pro Gly Val Gly Val Pro Gly Val Gly Val Pro Gly
                165                 170                 175

Lys Gly Val Pro Gly Val Gly Val Pro Gly Val Gly Val Pro Gly Val
            180                 185                 190

Gly Val Pro Gly Ala Gly Ala Gly Ser Gly Ala Gly Ala Gly Ser Gly
        195                 200                 205

Ala Gly Ala Gly Ser Gly Val Gly Val Pro Gly Val Gly Val Pro Gly
    210                 215                 220

Val Gly Val Pro Gly Val Gly Val Pro Gly Lys Gly Val Pro Gly Val
225                 230                 235                 240

Gly Val Pro Gly Val Gly Val Pro Gly Val Gly Val Pro Gly Ala Gly
                245                 250                 255

Ala Gly Ser Gly Ala Gly Ala Gly Ser Gly Ala Gly Ala Gly Ser Gly
            260                 265                 270

Val Gly Val Pro Gly Val Gly Val Pro Gly Val Gly Val Pro Gly Val
        275                 280                 285

Gly Val Pro Gly Lys Gly Val Pro Gly Val Gly Val Pro Gly Val Gly
    290                 295                 300

Val Pro Gly Val Gly Val Pro Gly Ala Gly Ala Gly Ser Gly Ala Gly
305                 310                 315                 320

Ala Gly Ser Gly Ala Gly Ala Gly Ser Gly Val Gly Val Pro Gly Val
                325                 330                 335

Gly Val Pro Gly Val Gly Val Pro Gly Val Gly Val Pro Gly Lys Gly
            340                 345                 350

Val Pro Gly Val Gly Val Pro Gly Val Gly Val Pro Gly Val Gly Val
        355                 360                 365

Pro Gly Ala Gly Ala Gly Ser Gly Ala Gly Ala Gly Ser Gly Ala Gly
    370                 375                 380

Ala Gly Ser Gly Val Gly Val Pro Gly Val Gly Val Pro Gly Val Gly
385                 390                 395                 400
```

```
Val Pro Gly Val Gly Val Pro Gly Lys Gly Val Pro Gly Val Gly Val
                405                 410                 415
Pro Gly Val Gly Val Pro Gly Val Gly Val Pro Gly Ala Gly Ala Gly
            420                 425                 430
Ser Gly Ala Gly Ala Gly Ser Gly Ala Gly Ala Gly Ser Gly Val Gly
            435                 440                 445
Val Pro Gly Val Gly Val Pro Gly Val Gly Val Pro Gly Val Gly Val
        450                 455                 460
Pro Gly Lys Gly Val Pro Gly Val Gly Val Pro Gly Val Gly Val Pro
465                 470                 475                 480
Gly Val Gly Val Pro Gly Ala Gly Ala Gly Ser Gly Ala Gly Ala Gly
            485                 490                 495
Ser Gly Ala Gly Ala Gly Ser Gly Val Gly Val Pro Gly Val Gly Val
            500                 505                 510
Pro Gly Val Gly Val Pro Gly Val Gly Val Pro Gly Lys Gly Val Pro
            515                 520                 525
Gly Val Gly Val Pro Gly Val Gly Val Pro Gly Val Gly Val Pro Gly
        530                 535                 540
Ala Gly Ala Gly Ser Gly Ala Gly Ala Gly Ser Gly Ala Gly Ala Gly
545                 550                 555                 560
Ser Gly Val Gly Val Pro Gly Val Gly Val Pro Gly Val Gly Val Pro
                565                 570                 575
Gly Val Gly Val Pro Gly Lys Gly Val Pro Gly Val Gly Val Pro Gly
            580                 585                 590
Val Gly Val Pro Gly Val Gly Val Pro Gly Ala Gly Ala Gly Ser Gly
            595                 600                 605
Ala Gly Ala Gly Ser Gly Ala Gly Ala Gly Ser Gly Val Gly Val Pro
610                 615                 620
Gly Val Gly Val Pro Gly Val Gly Val Pro Gly Val Gly Val Pro Gly
625                 630                 635                 640
Lys Gly Val Pro Gly Val Gly Val Pro Gly Val Gly Val Pro Gly Val
                645                 650                 655
Gly Val Pro Gly Ala Gly Ala Gly Ser Gly Ala Gly Ala Gly Ser Gly
                660                 665                 670
Ala Gly Ala Gly Ser Gly Val Gly Val Pro Gly Val Gly Val Pro Gly
            675                 680                 685
Val Gly Val Pro Gly Val Gly Val Pro Gly Lys Gly Val Pro Gly Val
            690                 695                 700
Gly Val Pro Gly Val Gly Val Pro Gly Val Gly Val Pro Gly Ala Gly
705                 710                 715                 720
Ala Gly Ser Gly Ala Gly Ala Gly Ser Gly Ala Gly Ala Met Asp Pro
                725                 730                 735
Gly Arg Tyr Gln Asp Leu Arg Ser His His His His
                740                 745                 750
```

(2) INFORMATION FOR SEQ ID NO:26:

(i) SEQUENCE CHARACTERISTICS:
        (A) LENGTH: 936 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:26:

-continued

```
Val Pro Gly Val Gly Val Pro Gly Val Gly Pro Gly Val Gly Val
 1               5                  10                  15
Pro Gly Val Gly Val Pro Gly Val Gly Val Pro Gly Val Gly Val Pro
            20                  25                  30
Gly Val Gly Val Pro Gly Val Gly Gly Ala Gly Ala Gly Ser Gly Ala
        35                  40                  45
Gly Ala Gly Ser Val Pro Gly Val Gly Val Pro Gly Val Gly Val Pro
 50                  55                  60
Gly Val Gly Val Pro Gly Val Gly Val Pro Gly Val Gly Val Pro Gly
 65                  70                  75                  80
Val Gly Val Pro Gly Val Gly Val Pro Gly Val Gly Gly Ala Gly Ala
                85                  90                  95
Gly Ser Gly Ala Gly Ala Gly Ser Val Pro Gly Val Gly Val Pro Gly
            100                 105                 110
Val Gly Val Pro Gly Val Gly Val Pro Gly Val Gly Val Pro Gly Val
            115                 120                 125
Gly Val Pro Gly Val Gly Val Pro Gly Val Gly Val Pro Gly Val Gly
        130                 135                 140
Gly Ala Gly Ala Gly Ser Gly Ala Gly Ala Gly Ser Val Pro Gly Val
145                 150                 155                 160
Gly Val Pro Gly Val Gly Val Pro Gly Val Gly Val Pro Gly Val Gly
            165                 170                 175
Val Pro Gly Val Gly Val Pro Gly Val Gly Val Pro Gly Val Gly Val
            180                 185                 190
Pro Gly Val Gly Val Gly Ala Gly Ala Gly Ser Gly Ala Gly Ala Gly Ser
            195                 200                 205
Val Pro Gly Val Gly Val Pro Gly Val Gly Val Pro Gly Val Gly Val
            210                 215                 220
Pro Gly Val Gly Val Pro Gly Val Gly Val Pro Gly Val Gly Val Pro
225                 230                 235                 240
Gly Val Gly Val Pro Gly Val Gly Gly Ala Gly Ala Gly Ser Gly Ala
            245                 250                 255
Gly Ala Gly Ser Val Pro Gly Val Gly Val Pro Gly Val Gly Val Pro
            260                 265                 270
Gly Val Gly Val Pro Gly Val Gly Val Pro Gly Val Gly Val Pro Gly
            275                 280                 285
Val Gly Val Pro Gly Val Gly Val Pro Gly Val Gly Gly Ala Gly Ala
            290                 295                 300
Gly Ser Gly Ala Gly Ala Gly Ser Val Pro Gly Val Gly Val Pro Gly
305                 310                 315                 320
Val Gly Val Pro Gly Val Gly Val Pro Gly Val Gly Val Pro Gly Val
            325                 330                 335
Gly Val Pro Gly Val Gly Val Pro Gly Val Gly Val Pro Gly Val Gly
        340                 345                 350
Gly Ala Gly Ala Gly Ser Gly Ala Gly Ala Gly Ser Val Pro Gly Val
        355                 360                 365
Gly Val Pro Gly Val Gly Val Pro Gly Val Gly Val Pro Gly Val Gly
        370                 375                 380
Val Pro Gly Val Gly Val Pro Gly Val Gly Val Pro Gly Val Gly Val
385                 390                 395                 400
Pro Gly Val Gly Gly Ala Gly Ala Gly Ser Gly Ala Gly Ala Gly Ser
            405                 410                 415
```

-continued

```
Val Pro Gly Val Gly Val Pro Gly Val Gly Pro Val Gly Val
            420                 425                 430

Pro Gly Val Gly Val Pro Gly Val Gly Val Pro Gly Val Gly Val Pro
            435                 440                 445

Gly Val Gly Val Pro Gly Val Gly Ala Gly Ala Gly Ser Gly Ala
450                 455                 460

Gly Ala Gly Ser Val Pro Gly Val Gly Val Pro Gly Val Gly Val Pro
465                 470                 475                 480

Gly Val Gly Val Pro Gly Val Gly Val Pro Gly Val Gly Val Pro Gly
            485                 490                 495

Val Gly Val Pro Gly Val Gly Val Pro Gly Val Gly Ala Gly Ala
            500                 505                 510

Gly Ser Gly Ala Gly Ala Gly Ser Val Pro Gly Val Gly Val Pro Gly
            515                 520                 525

Val Gly Val Pro Gly Val Gly Val Pro Gly Val Gly Val Pro Gly Val
            530                 535                 540

Gly Val Pro Gly Val Gly Val Pro Gly Val Gly Val Pro Gly Val Gly
545                 550                 555                 560

Gly Ala Gly Ala Gly Ser Gly Ala Gly Ala Gly Ser Val Pro Gly Val
            565                 570                 575

Gly Val Pro Gly Val Gly Val Pro Gly Val Gly Val Pro Gly Val Gly
            580                 585                 590

Val Pro Gly Val Gly Val Pro Gly Val Gly Val Pro Gly Val Gly Val
            595                 600                 605

Pro Gly Val Gly Gly Ala Gly Ala Gly Ser Gly Ala Gly Ala Gly Ser
            610                 615                 620

Val Pro Gly Val Gly Val Pro Gly Val Gly Val Pro Gly Val Gly Val
625                 630                 635                 640

Pro Gly Val Gly Val Pro Gly Val Gly Val Pro Gly Val Gly Val Pro
            645                 650                 655

Gly Val Gly Val Pro Gly Val Gly Ala Gly Ala Gly Ser Gly Ala
            660                 665                 670

Gly Ala Gly Ser Val Pro Gly Val Gly Val Pro Gly Val Gly Val Pro
            675                 680                 685

Gly Val Gly Val Pro Gly Val Gly Val Pro Gly Val Gly Val Pro Gly
            690                 695                 700

Val Gly Val Pro Gly Val Gly Val Pro Gly Val Gly Ala Gly Ala
705                 710                 715                 720

Gly Ser Gly Ala Gly Ala Gly Ser Val Pro Gly Val Gly Val Pro Gly
            725                 730                 735

Val Gly Val Pro Gly Val Gly Val Pro Gly Val Gly Val Pro Gly Val
            740                 745                 750

Gly Val Pro Gly Val Gly Val Pro Gly Val Gly Val Pro Gly Val Gly
            755                 760                 765

Gly Ala Gly Ala Gly Ser Gly Ala Gly Ala Gly Ser Val Pro Gly Val
770                 775                 780

Gly Val Pro Gly Val Gly Val Pro Gly Val Gly Val Pro Gly Val Gly
785                 790                 795                 800

Val Pro Gly Val Gly Val Pro Gly Val Gly Val Pro Gly Val Gly Val
            805                 810                 815

Pro Gly Val Gly Gly Ala Gly Ala Gly Ser Gly Ala Gly Ala Gly Ser
            820                 825                 830

Val Pro Gly Val Gly Val Pro Gly Val Gly Val Pro Gly Val Gly Val
```

-continued

```
                835                 840                 845
Pro Gly Val Gly Val Pro Gly Val Gly Val Pro Gly Val Gly Val Pro
            850                 855                 860

Gly Val Gly Val Pro Gly Val Gly Gly Ala Gly Ala Gly Ser Gly Ala
865                 870                 875                 880

Gly Ala Gly Ser Val Pro Gly Val Gly Val Pro Gly Val Gly Val Pro
                885                 890                 895

Gly Val Gly Val Pro Gly Val Gly Val Pro Gly Val Gly Val Pro Gly
            900                 905                 910

Val Gly Val Pro Gly Val Gly Val Pro Gly Val Gly Ala Gly Ala
        915                 920                 925

Gly Ser Gly Ala Gly Ala Gly Ser
930                 935
```

(2) INFORMATION FOR SEQ ID NO:27:

(i) SEQUENCE CHARACTERISTICS:
        (A) LENGTH: 832 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:27:

```
Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Val Pro Gly Val Gly Val Pro Gly Val Gly Val Pro Gly Val Gly Val
65                  70                  75                  80

Pro Gly Val Gly Val Pro Gly Val Gly Val Pro Gly Val Gly Val Pro
            85                  90                  95

Gly Val Gly Val Pro Gly Val Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125

Val Pro Gly Val Gly Val Pro Gly Val Gly Val Pro Gly Val Gly Val
130                 135                 140

Pro Gly Val Gly Val Pro Gly Val Gly Val Pro Gly Val Gly Val Pro
145                 150                 155                 160

Gly Val Gly Val Pro Gly Val Gly Ala Gly Ala Gly Ser Gly Ala
                165                 170                 175

Gly Ala Gly Ser Gly Ala Gly Ala Gly Ser Gly Ala Gly Ala Gly Ser
            180                 185                 190

Val Pro Gly Val Gly Val Pro Gly Val Gly Val Pro Gly Val Gly Val
        195                 200                 205

Pro Gly Val Gly Val Pro Gly Val Gly Val Pro Gly Val Gly Val Pro
    210                 215                 220

Gly Val Gly Val Pro Gly Val Gly Ala Gly Ala Gly Ser Gly Ala
225                 230                 235                 240

Gly Ala Gly Ser Gly Ala Gly Ala Gly Ser Gly Ala Gly Ala Gly Ser
```

-continued

```
                245                 250                 255
Val Pro Gly Val Gly Val Pro Gly Val Gly Val Pro Gly Val Gly Val
                260                 265                 270
Pro Gly Val Gly Val Pro Gly Val Gly Val Pro Gly Val Gly Val Pro
            275                 280                 285
Gly Val Gly Val Pro Gly Val Gly Ala Gly Ala Gly Ser Gly Ala
        290                 295                 300
Gly Ala Gly Ser Gly Ala Gly Ala Gly Ser Gly Ala Gly Ala Gly Ser
305                 310                 315                 320
Val Pro Gly Val Gly Val Pro Gly Val Gly Val Pro Gly Val Gly Val
                325                 330                 335
Pro Gly Val Gly Val Pro Gly Val Gly Val Pro Gly Val Gly Val Pro
            340                 345                 350
Gly Val Gly Val Pro Gly Val Gly Ala Gly Ala Gly Ser Gly Ala
        355                 360                 365
Gly Ala Gly Ser Gly Ala Gly Ala Gly Ser Gly Ala Gly Ala Gly Ser
        370                 375                 380
Val Pro Gly Val Gly Val Pro Gly Val Gly Val Pro Gly Val Gly Val
385                 390                 395                 400
Pro Gly Val Gly Val Pro Gly Val Gly Val Pro Gly Val Gly Val Pro
            405                 410                 415
Gly Val Gly Val Pro Gly Val Gly Ala Gly Ala Gly Ser Gly Ala
            420                 425                 430
Gly Ala Gly Ser Gly Ala Gly Ala Gly Ser Gly Ala Gly Ala Gly Ser
        435                 440                 445
Val Pro Gly Val Gly Val Pro Gly Val Gly Val Pro Gly Val Gly Val
    450                 455                 460
Pro Gly Val Gly Val Pro Gly Val Gly Val Pro Gly Val Gly Val Pro
465                 470                 475                 480
Gly Val Gly Val Pro Gly Val Gly Ala Gly Ala Gly Ser Gly Ala
            485                 490                 495
Gly Ala Gly Ser Gly Ala Gly Ala Gly Ser Gly Ala Gly Ala Gly Ser
            500                 505                 510
Val Pro Gly Val Gly Val Pro Gly Val Gly Val Pro Gly Val Gly Val
        515                 520                 525
Pro Gly Val Gly Val Pro Gly Val Gly Val Pro Gly Val Gly Val Pro
    530                 535                 540
Gly Val Gly Val Pro Gly Val Gly Ala Gly Ala Gly Ser Gly Ala
545                 550                 555                 560
Gly Ala Gly Ser Gly Ala Gly Ala Gly Ser Gly Ala Gly Ala Gly Ser
            565                 570                 575
Val Pro Gly Val Gly Val Pro Gly Val Gly Val Pro Gly Val Gly Val
            580                 585                 590
Pro Gly Val Gly Val Pro Gly Val Gly Val Pro Gly Val Gly Val Pro
        595                 600                 605
Gly Val Gly Val Pro Gly Val Gly Ala Gly Ala Gly Ser Gly Ala
    610                 615                 620
Gly Ala Gly Ser Gly Ala Gly Ala Gly Ser Gly Ala Gly Ala Gly Ser
625                 630                 635                 640
Val Pro Gly Val Gly Val Pro Gly Val Gly Val Pro Gly Val Gly Val
            645                 650                 655
Pro Gly Val Gly Val Pro Gly Val Gly Val Pro Gly Val Gly Val Pro
        660                 665                 670
```

```
Gly Val Gly Val Pro Gly Val Gly Ala Gly Ala Gly Ser Gly Ala
            675                 680                 685

Gly Ala Gly Ser Gly Ala Gly Ala Gly Ser Gly Ala Gly Ala Gly Ser
    690                 695                 700

Val Pro Gly Val Gly Val Pro Gly Val Gly Val Pro Gly Val Gly Val
705                 710                 715                 720

Pro Gly Val Gly Val Pro Gly Val Gly Val Pro Gly Val Gly Val Pro
                725                 730                 735

Gly Val Gly Val Pro Gly Val Gly Ala Gly Ala Gly Ser Gly Ala
            740                 745                 750

Gly Ala Gly Ser Gly Ala Gly Ala Gly Ser Gly Ala Gly Ala Gly Ser
    755                 760                 765

Val Pro Gly Val Gly Val Pro Gly Val Gly Val Pro Gly Val Gly Val
    770                 775                 780

Pro Gly Val Gly Val Pro Gly Val Gly Val Pro Gly Val Gly Val Pro
785                 790                 795                 800

Gly Val Gly Val Pro Gly Val Gly Ala Gly Ala Gly Ser Gly Ala
            805                 810                 815

Gly Ala Gly Ser Gly Ala Gly Ala Gly Ser Gly Ala Gly Ala Gly Ser
    820                 825                 830

(2) INFORMATION FOR SEQ ID NO:28:

(i) SEQUENCE CHARACTERISTICS:
        (A) LENGTH: 988 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:28:

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Gly Ala Gly Ala Gly Ser Gly Ala
            35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser Val Pro Gly Val
65                  70                  75                  80

Gly Val Pro Gly Val Gly Val Pro Gly Val Gly Val Pro Gly Val Gly
            85                  90                  95

Val Pro Gly Val Gly Val Pro Gly Val Gly Val Pro Gly Val Gly Val
            100                 105                 110

Pro Gly Val Gly Gly Ala Gly Ala Gly Ser Gly Ala Gly Ala Gly Ser
        115                 120                 125

Gly Ala Gly Ala Gly Ser Gly Ala Gly Ala Gly Ser Gly Ala Gly Ala
    130                 135                 140

Gly Ser Gly Ala Gly Ala Gly Ser Val Pro Gly Val Gly Val Pro Gly
145                 150                 155                 160

Val Gly Val Pro Gly Val Gly Val Pro Gly Val Gly Val Pro Gly Val
            165                 170                 175

Gly Val Pro Gly Val Gly Val Pro Gly Val Gly Val Pro Gly Val Gly
            180                 185                 190
```

-continued

```
Gly Ala Gly Ala Gly Ser Gly Ala Gly Ala Gly Ser Gly Ala Gly Ala
            195                 200                 205
Gly Ser Gly Ala Gly Ala Gly Ser Gly Ala Gly Ala Gly Ser Gly Ala
        210                 215                 220
Gly Ala Gly Ser Val Pro Gly Val Gly Val Pro Gly Val Gly Val Pro
225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Ala Gly Ala
            260                 265                 270
Gly Ser Gly Ala Gly Ala Gly Ser Gly Ala Gly Ala Gly Ser Gly Ala
        275                 280                 285
Gly Ala Gly Ser Gly Ala Gly Ala Gly Ser Gly Ala Gly Ala Gly Ser
        290                 295                 300
Val Pro Gly Val Gly Val Pro Gly Val Gly Val Pro Gly Val Gly Val
305                 310                 315                 320
Pro Gly Val Gly Val Pro Gly Val Gly Val Pro Gly Val Gly Val Pro
                325                 330                 335
Gly Val Gly Val Pro Gly Val Gly Ala Gly Ala Gly Ser Gly Ala
            340                 345                 350
Gly Ala Gly Ser Gly Ala Gly Ala Gly Ser Gly Ala Gly Ala Gly Ser
        355                 360                 365
Gly Ala Gly Ala Gly Ser Gly Ala Gly Ala Gly Ser Val Pro Gly Val
        370                 375                 380
Gly Val Pro Gly Val Gly Val Pro Gly Val Gly Val Pro Gly Val Gly
385                 390                 395                 400
Val Pro Gly Val Gly Val Pro Gly Val Gly Val Pro Gly Val Gly Val
                405                 410                 415
Pro Gly Val Gly Gly Ala Gly Ala Gly Ser Gly Ala Gly Ala Gly Ser
                420                 425                 430
Gly Ala Gly Ala Gly Ser Gly Ala Gly Ala Gly Ser Gly Ala Gly Ala
        435                 440                 445
Gly Ser Gly Ala Gly Ala Gly Ser Val Pro Gly Val Gly Val Pro Gly
    450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Val Gly
                485                 490                 495
Gly Ala Gly Ala Gly Ser Gly Ala Gly Ala Gly Ser Gly Ala Gly Ala
            500                 505                 510
Gly Ser Gly Ala Gly Ala Gly Ser Gly Ala Gly Ala Gly Ser Gly Ala
        515                 520                 525
Gly Ala Gly Ser Val Pro Gly Val Gly Val Pro Gly Val Gly Val Pro
        530                 535                 540
Gly Val Gly Val Pro Gly Val Gly Val Pro Gly Val Gly Val Pro Gly
545                 550                 555                 560
Val Gly Val Pro Gly Val Gly Val Pro Gly Val Gly Gly Ala Gly Ala
                565                 570                 575
Gly Ser Gly Ala Gly Ala Gly Ser Gly Ala Gly Ala Gly Ser Gly Ala
        580                 585                 590
Gly Ala Gly Ser Gly Ala Gly Ala Gly Ser Gly Ala Gly Ala Gly Ser
        595                 600                 605
```

-continued

```
Val Pro Gly Val Gly Val Pro Gly Val Gly Val Pro Gly Val Gly Val
    610                 615                 620
Pro Gly Val Gly Val Pro Gly Val Gly Val Pro Gly Val Gly Val Pro
625                 630                 635                 640
Gly Val Gly Val Pro Gly Val Gly Gly Ala Gly Ala Gly Ser Gly Ala
                645                 650                 655
Gly Ala Gly Ser Gly Ala Gly Ala Gly Ser Gly Ala Gly Ala Gly Ser
            660                 665                 670
Gly Ala Gly Ala Gly Ser Gly Ala Gly Ala Gly Ser Val Pro Gly Val
        675                 680                 685
Gly Val Pro Gly Val Gly Val Pro Gly Val Gly Val Pro Gly Val Gly
    690                 695                 700
Val Pro Gly Val Gly Val Pro Gly Val Gly Val Pro Gly Val Gly Val
705                 710                 715                 720
Pro Gly Val Gly Gly Ala Gly Ala Gly Ser Gly Ala Gly Ala Gly Ser
                725                 730                 735
Gly Ala Gly Ala Gly Ser Gly Ala Gly Ala Gly Ser Gly Ala Gly Ala
            740                 745                 750
Gly Ser Gly Ala Gly Ala Gly Ser Val Pro Gly Val Gly Val Pro Gly
        755                 760                 765
Val Gly Val Pro Gly Val Gly Val Pro Gly Val Gly Val Pro Gly Val
    770                 775                 780
Gly Val Pro Gly Val Gly Val Pro Gly Val Gly Val Pro Gly Val Gly
785                 790                 795                 800
Gly Ala Gly Ala Gly Ser Gly Ala Gly Ala Gly Ser Gly Ala Gly Ala
                805                 810                 815
Gly Ser Gly Ala Gly Ser Gly Ala Gly Ala Gly Ser Gly Ala
            820                 825                 830
Gly Ala Gly Ser Val Pro Gly Val Gly Val Pro Gly Val Gly Val Pro
        835                 840                 845
Gly Val Gly Val Pro Gly Val Gly Val Pro Gly Val Gly Val Pro Gly
    850                 855                 860
Val Gly Val Pro Gly Val Gly Val Pro Gly Val Gly Gly Ala Gly Ala
865                 870                 875                 880
Gly Ser Gly Ala Gly Ala Gly Ser Gly Ala Gly Ala Gly Ser Gly Ala
                885                 890                 895
Gly Ala Gly Ser Gly Ala Gly Ala Gly Ser Gly Ala Gly Ala Gly Ser
            900                 905                 910
Val Pro Gly Val Gly Val Pro Gly Val Gly Val Pro Gly Val Gly Val
        915                 920                 925
Pro Gly Val Gly Val Pro Gly Val Gly Val Pro Gly Val Gly Val Pro
    930                 935                 940
Gly Val Gly Val Pro Gly Val Gly Gly Ala Gly Ala Gly Ser Gly Ala
945                 950                 955                 960
Gly Ala Gly Ser Gly Ala Gly Ala Gly Ser Gly Ala Gly Ala Gly Ser
                965                 970                 975
Gly Ala Gly Ala Gly Ser Gly Ala Gly Ala Gly Ser
            980                 985

(2) INFORMATION FOR SEQ ID NO:29:

(i) SEQUENCE CHARACTERISTICS:
        (A) LENGTH: 1056 amino acids
        (B) TYPE: amino acid
        (C) STRANDEDNESS: unknown
```

-continued (D) TOPOLOGY: unknown (ii) MOLECULE TYPE: protein (xi) SEQUENCE DESCRIPTION: SEQ ID NO:29:

```
Val Pro Gly Val Gly Val Pro Gly Val Gly Val Pro Gly Val Gly Val
 1               5                  10                  15

Pro Gly Val Gly Val Pro Gly Val Gly Val Pro Gly Val Gly Val Pro
             20                  25                  30

Gly Val Gly Val Pro Gly Val Gly Ala Gly Ala Gly Ser Gly Ala
         35                  40                  45

Gly Ala Gly Ser Gly Ala Gly Ala Gly Ser Gly Ala Gly Ala Gly Ser
         50                  55                  60

Gly Ala Gly Ala Gly Ser Gly Ala Gly Ala Gly Ser Gly Ala Gly Ala
65                  70                  75                  80

Gly Ser Gly Ala Gly Ala Gly Ser Val Pro Gly Val Gly Val Pro Gly
             85                  90                  95

Val Gly Val Pro Gly Val Gly Val Pro Gly Val Gly Val Pro Gly Val
                100                 105                 110

Gly Val Pro Gly Val Gly Val Pro Gly Val Gly Val Pro Gly Val Gly
             115                 120                 125

Gly Ala Gly Ala Gly Ser Gly Ala Gly Ala Gly Ser Gly Ala Gly Ala
             130                 135                 140

Gly Ser Gly Ala Gly Ala Gly Ser Gly Ala Gly Ala Gly Ser Gly Ala
145                 150                 155                 160

Gly Ala Gly Ser Gly Ala Gly Ala Gly Ser Gly Ala Gly Ala Gly Ser
                165                 170                 175

Val Pro Gly Val Gly Val Pro Gly Val Gly Val Pro Gly Val Gly Val
                180                 185                 190

Pro Gly Val Gly Val Pro Gly Val Gly Val Pro Gly Val Gly Val Pro
             195                 200                 205

Gly Val Gly Val Pro Gly Val Gly Ala Gly Ala Gly Ser Gly Ala
         210                 215                 220

Gly Ala Gly Ser Gly Ala Gly Ala Gly Ser Gly Ala Gly Ala Gly Ser
225                 230                 235                 240

Gly Ala Gly Ala Gly Ser Gly Ala Gly Ala Gly Ser Gly Ala Gly Ala
                245                 250                 255

Gly Ser Gly Ala Gly Ala Gly Ser Val Pro Gly Val Gly Val Pro Gly
             260                 265                 270

Val Gly Val Pro Gly Val Gly Val Pro Gly Val Gly Val Pro Gly Val
             275                 280                 285

Gly Val Pro Gly Val Gly Val Pro Gly Val Gly Val Pro Gly Val Gly
             290                 295                 300

Gly Ala Gly Ala Gly Ser Gly Ala Gly Ala Gly Ser Gly Ala Gly Ala
305                 310                 315                 320

Gly Ser Gly Ala Gly Ala Gly Ser Gly Ala Gly Ala Gly Ser Gly Ala
                325                 330                 335

Gly Ala Gly Ser Gly Ala Gly Ala Gly Ser Gly Ala Gly Ala Gly Ser
             340                 345                 350

Val Pro Gly Val Gly Val Pro Gly Val Gly Val Pro Gly Val Gly Val
             355                 360                 365

Pro Gly Val Gly Val Pro Gly Val Gly Val Pro Gly Val Gly Val Pro
             370                 375                 380

Gly Val Gly Val Pro Gly Val Gly Gly Ala Gly Ala Gly Ser Gly Ala
```

-continued

```
            385                 390                 395                 400
Gly Ala Gly Ser Gly Ala Gly Ala Gly Ser Gly Ala Gly Ala Gly Ser
                    405                 410                 415
Gly Ala Gly Ala Gly Ser Gly Ala Gly Ala Gly Ser Gly Ala Gly Ala
                    420                 425                 430
Gly Ser Gly Ala Gly Ala Gly Ser Val Pro Gly Val Gly Val Pro Gly
                    435                 440                 445
Val Gly Val Pro Gly Val Gly Val Pro Gly Val Gly Val Pro Gly Val
        450                 455                 460
Gly Val Pro Gly Val Gly Val Pro Gly Val Gly Val Pro Gly Val Gly
465                 470                 475                 480
Gly Ala Gly Ala Gly Ser Gly Ala Gly Ala Gly Ser Gly Ala Gly Ala
                    485                 490                 495
Gly Ser Gly Ala Gly Ala Gly Ser Gly Ala Gly Ala Gly Ser Gly Ala
                    500                 505                 510
Gly Ala Gly Ser Gly Ala Gly Ala Gly Ser Gly Ala Gly Ala Gly Ser
                    515                 520                 525
Val Pro Gly Val Gly Val Pro Gly Val Gly Val Pro Gly Val Gly Val
        530                 535                 540
Pro Gly Val Gly Val Pro Gly Val Gly Val Pro Gly Val Gly Val Pro
545                 550                 555                 560
Gly Val Gly Val Pro Gly Val Gly Ala Gly Ala Gly Ser Gly Ala
                    565                 570                 575
Gly Ala Gly Ser Gly Ala Gly Ala Gly Ser Gly Ala Gly Ala Gly Ser
                    580                 585                 590
Gly Ala Gly Ala Gly Ser Gly Ala Gly Ala Gly Ser Gly Ala Gly Ala
                    595                 600                 605
Gly Ser Gly Ala Gly Ala Gly Ser Val Pro Gly Val Gly Val Pro Gly
                    610                 615                 620
Val Gly Val Pro Gly Val Gly Val Pro Gly Val Gly Val Pro Gly Val
625                 630                 635                 640
Gly Val Pro Gly Val Gly Val Pro Gly Val Gly Val Pro Gly Val Gly
                    645                 650                 655
Gly Ala Gly Ala Gly Ser Gly Ala Gly Ala Gly Ser Gly Ala Gly Ala
                    660                 665                 670
Gly Ser Gly Ala Gly Ala Gly Ser Gly Ala Gly Ala Gly Ser Gly Ala
                    675                 680                 685
Gly Ala Gly Ser Gly Ala Gly Ala Gly Ser Gly Ala Gly Ala Gly Ser
                    690                 695                 700
Val Pro Gly Val Gly Val Pro Gly Val Gly Val Pro Gly Val Gly Val
705                 710                 715                 720
Pro Gly Val Gly Val Pro Gly Val Gly Val Pro Gly Val Gly Val Pro
                    725                 730                 735
Gly Val Gly Val Pro Gly Val Gly Ala Gly Ala Gly Ser Gly Ala
                    740                 745                 750
Gly Ala Gly Ser Gly Ala Gly Ala Gly Ser Gly Ala Gly Ala Gly Ser
                    755                 760                 765
Gly Ala Gly Ala Gly Ser Gly Ala Gly Ala Gly Ser Gly Ala Gly Ala
                    770                 775                 780
Gly Ser Gly Ala Gly Ala Gly Ser Val Pro Gly Val Gly Val Pro Gly
785                 790                 795                 800
Val Gly Val Pro Gly Val Gly Val Pro Gly Val Gly Val Pro Gly Val
                    805                 810                 815
```

```
Gly Val Pro Gly Val Gly Val Pro Gly Val Gly Val Pro Gly Val Gly
            820                 825                 830
Gly Ala Gly Ala Gly Ser Gly Ala Gly Ala Gly Ser Gly Ala Gly Ala
            835                 840                 845
Gly Ser Gly Ala Gly Ala Gly Ser Gly Ala Gly Ala Gly Ser Gly Ala
            850                 855                 860
Gly Ala Gly Ser Gly Ala Gly Ala Gly Ser Gly Ala Gly Ala Gly Ser
865                 870                 875                 880
Val Pro Gly Val Gly Val Pro Gly Val Gly Val Pro Gly Val Gly Val
            885                 890                 895
Pro Gly Val Gly Val Pro Gly Val Gly Val Pro Gly Val Gly Val Pro
            900                 905                 910
Gly Val Gly Val Pro Gly Val Gly Ala Gly Ala Gly Ser Gly Ala
            915                 920                 925
Gly Ala Gly Ser Gly Ala Gly Ala Gly Ser Gly Ala Gly Ala Gly Ser
            930                 935                 940
Gly Ala Gly Ala Gly Ser Gly Ala Gly Ala Gly Ser Gly Ala Gly Ala
945                 950                 955                 960
Gly Ser Gly Ala Gly Ala Gly Ser Val Pro Gly Val Gly Val Pro Gly
            965                 970                 975
Val Gly Val Pro Gly Val Gly Val Pro Gly Val Gly Val Pro Gly Val
            980                 985                 990
Gly Val Pro Gly Val Gly Val Pro Gly Val Gly Val Pro Gly Val Gly
            995                 1000                1005
Gly Ala Gly Ala Gly Ser Gly Ala Gly Ala Gly Ser Gly Ala Gly Ala
            1010                1015                1020
Gly Ser Gly Ala Gly Ala Gly Ser Gly Ala Gly Ala Gly Ser Gly Ala
1025                1030                1035                1040
Gly Ala Gly Ser Gly Ala Gly Ala Gly Ser Gly Ala Gly Ala Gly Ser
                  1045                1050                1055

(2) INFORMATION FOR SEQ ID NO:30:

(i) SEQUENCE CHARACTERISTICS:
        (A) LENGTH: 972 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:30:

Val Pro Gly Val Gly Val Pro Gly Val Gly Val Pro Gly Val Gly Val
1               5                   10                  15
Pro Gly Val Gly Val Pro Gly Val Gly Val Pro Gly Val Gly Val Pro
            20                  25                  30
Gly Val Gly Val Pro Gly Val Gly Val Pro Gly Val Gly Val Pro Gly
            35                  40                  45
Val Gly Val Pro Gly Val Gly Val Pro Gly Val Gly Ala Gly Ala
            50                  55                  60
Gly Ser Gly Ala Gly Ala Gly Ser Gly Ala Gly Ala Gly Ser Gly Ala
65                  70                  75                  80
Gly Ala Gly Ser Gly Ala Gly Ala Gly Ser Gly Ala Gly Ala Gly Ser
                85                  90                  95
Gly Ala Gly Ala Gly Ser Gly Ala Gly Ala Gly Ser Val Pro Gly Val
            100                 105                 110
```

-continued

```
Gly Val Pro Gly Val Gly Val Pro Gly Val Gly Val Pro Gly Val Gly
            115                 120                 125
Val Pro Gly Val Gly Val Pro Gly Val Gly Val Pro Gly Val Gly Val
130                 135                 140
Pro Gly Val Gly Val Pro Gly Val Gly Val Pro Gly Val Gly Val Pro
145                 150                 155                 160
Gly Val Gly Val Pro Gly Val Gly Gly Ala Gly Ala Gly Ser Gly Ala
                165                 170                 175
Gly Ala Gly Ser Gly Ala Gly Ala Gly Ser Gly Ala Gly Ala Gly Ser
            180                 185                 190
Gly Ala Gly Ala Gly Ser Gly Ala Gly Ala Gly Ser Gly Ala Gly Ala
            195                 200                 205
Gly Ser Gly Ala Gly Ala Gly Ser Val Pro Gly Val Gly Val Pro Gly
            210                 215                 220
Val Gly Val Pro Gly Val Gly Val Pro Gly Val Gly Val Pro Gly Val
225                 230                 235                 240
Gly Val Pro Gly Val Gly Val Pro Gly Val Gly Val Pro Gly Val Gly
            245                 250                 255
Val Pro Gly Val Gly Val Pro Gly Val Gly Val Pro Gly Val Gly Val
            260                 265                 270
Pro Gly Val Gly Gly Ala Gly Ala Gly Ser Gly Ala Gly Ala Gly Ser
            275                 280                 285
Gly Ala Gly Ala Gly Ser Gly Ala Gly Ala Gly Ser Gly Ala Gly Ala
            290                 295                 300
Gly Ser Gly Ala Gly Ala Gly Ser Gly Ala Gly Ala Gly Ser Gly Ala
305                 310                 315                 320
Gly Ala Gly Ser Val Pro Gly Val Gly Val Pro Gly Val Gly Val Pro
                325                 330                 335
Gly Val Gly Val Pro Gly Val Gly Val Pro Gly Val Gly Val Pro Gly
            340                 345                 350
Val Gly Val Pro Gly Val Gly Val Pro Gly Val Gly Val Pro Gly Val
            355                 360                 365
Gly Val Pro Gly Val Gly Val Pro Gly Val Gly Val Pro Gly Val Gly
            370                 375                 380
Gly Ala Gly Ala Gly Ser Gly Ala Gly Ala Gly Ser Gly Ala Gly Ala
385                 390                 395                 400
Gly Ser Gly Ala Gly Ala Gly Ser Gly Ala Gly Ala Gly Ser Gly Ala
                405                 410                 415
Gly Ala Gly Ser Gly Ala Gly Ala Gly Ser Gly Ala Gly Ala Gly Ser
            420                 425                 430
Val Pro Gly Val Gly Val Pro Gly Val Gly Val Pro Gly Val Gly Val
            435                 440                 445
Pro Gly Val Gly Val Pro Gly Val Gly Val Pro Gly Val Gly Val Pro
450                 455                 460
Gly Val Gly Val Pro Gly Val Gly Val Pro Gly Val Gly Val Pro Gly
465                 470                 475                 480
Val Gly Val Pro Gly Val Gly Val Pro Gly Val Gly Gly Ala Gly Ala
                485                 490                 495
Gly Ser Gly Ala Gly Ala Gly Ser Gly Ala Gly Ala Gly Ser Gly Ala
            500                 505                 510
Gly Ala Gly Ser Gly Ala Gly Ala Gly Ser Gly Ala Gly Ala Gly Ser
            515                 520                 525
```

```
Gly Ala Gly Ala Gly Ser Gly Ala Gly Ala Ser Val Pro Gly Val
        530                 535                 540
Gly Val Pro Gly Val Gly Val Pro Gly Val Gly Val Pro Gly Val Gly
545                 550                 555                 560
Val Pro Gly Val Gly Val Pro Gly Val Gly Val Pro Gly Val Gly Val
                565                 570                 575
Pro Gly Val Gly Val Pro Gly Val Gly Val Pro Gly Val Gly Val Pro
            580                 585                 590
Gly Val Gly Val Pro Gly Val Gly Ala Gly Ala Gly Ser Gly Ala
        595                 600                 605
Gly Ala Gly Ser Gly Ala Gly Ala Ser Gly Ala Gly Ala Gly Ser
        610                 615                 620
Gly Ala Gly Ala Gly Ser Gly Ala Gly Ala Ser Gly Ala Gly Ala
625                 630                 635                 640
Gly Ser Gly Ala Gly Ala Gly Ser Val Pro Gly Val Gly Val Pro Gly
                645                 650                 655
Val Gly Val Pro Gly Val Gly Val Pro Gly Val Gly Val Pro Gly Val
            660                 665                 670
Gly Val Pro Gly Val Gly Val Pro Gly Val Gly Val Pro Gly Val Gly
        675                 680                 685
Val Pro Gly Val Gly Val Pro Gly Val Gly Val Pro Gly Val Gly Val
690                 695                 700
Pro Gly Val Gly Gly Ala Gly Ala Gly Ser Gly Ala Gly Ala Gly Ser
705                 710                 715                 720
Gly Ala Gly Ala Gly Ser Gly Ala Gly Ala Gly Ser Gly Ala Gly Ala
                725                 730                 735
Gly Ser Gly Ala Gly Ala Gly Ser Gly Ala Gly Ala Gly Ser Gly Ala
            740                 745                 750
Gly Ala Gly Ser Val Pro Gly Val Gly Val Pro Gly Val Gly Val Pro
        755                 760                 765
Gly Val Gly Val Pro Gly Val Gly Val Pro Gly Val Gly Val Pro Gly
770                 775                 780
Val Gly Val Pro Gly Val Gly Val Pro Gly Val Gly Val Pro Gly Val
785                 790                 795                 800
Gly Val Pro Gly Val Gly Val Pro Gly Val Gly Val Pro Gly Val Gly
                805                 810                 815
Gly Ala Gly Ala Gly Ser Gly Ala Gly Ala Ser Gly Ala Gly Ala
            820                 825                 830
Gly Ser Gly Ala Gly Ala Gly Ser Gly Ala Gly Ala Ser Gly Ala
        835                 840                 845
Gly Ala Gly Ser Gly Ala Gly Ala Ser Gly Ala Gly Ala Gly Ser
850                 855                 860
Val Pro Gly Val Gly Val Pro Gly Val Gly Val Pro Gly Val Gly Val
865                 870                 875                 880
Pro Gly Val Gly Val Pro Gly Val Gly Val Pro Gly Val Gly Val Pro
                885                 890                 895
Gly Val Gly Val Pro Gly Val Gly Val Pro Gly Val Gly Val Pro Gly
            900                 905                 910
Val Gly Val Pro Gly Val Gly Val Pro Gly Val Gly Gly Ala Gly Ala
        915                 920                 925
Gly Ser Gly Ala Gly Ala Gly Ser Gly Ala Gly Ala Gly Ser Gly Ala
        930                 935                 940
Gly Ala Gly Ser Gly Ala Gly Ala Gly Ser Gly Ala Gly Ala Gly Ser
```

```
                                 945                 950                 955                 960

Gly Ala Gly Ala Gly Ser Gly Ala Gly Ala Gly Ser
                        965                 970

(2) INFORMATION FOR SEQ ID NO:31:

(i) SEQUENCE CHARACTERISTICS:
        (A) LENGTH: 1024 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:31:

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Gly Ala Gly Ala Gly Ser Gly Ala Gly Ala Gly Ser Gly Ala Gly Ala
    210                 215                 220

Gly Ser Gly Ala Gly Ala Gly Ser Gly Ala Gly Ala Gly Ser Gly Ala
225                 230                 235                 240

Gly Ala Gly Ser Gly Ala Gly Ala Gly Ser Gly Ala Gly Ala Gly Ser
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Val Gly Val Pro Gly Val Gly Val Pro Gly Val Gly Val Pro Gly
    290                 295                 300

Val Gly Val Pro Gly Val Gly Val Pro Gly Val Gly Val Pro Gly Val
305                 310                 315                 320

Gly Val Pro Gly Val Gly Val Pro Gly Val Gly Val Pro Gly Val Gly
```

-continued

```
                  325                 330                 335
Gly Ala Gly Ala Gly Ser Gly Ala Gly Ala Gly Ser Gly Ala Gly Ala
                340                 345                 350
Gly Ser Gly Ala Gly Ala Gly Ser Gly Ala Gly Ala Gly Ser Gly Ala
                355                 360                 365
Gly Ala Gly Ser Gly Ala Gly Ala Gly Ser Gly Ala Gly Ala Gly Ser
                370                 375                 380
Val Pro Gly Val Gly Val Pro Gly Val Gly Val Pro Gly Val Gly Val
385                 390                 395                 400
Pro Gly Val Gly Val Pro Gly Val Gly Val Pro Gly Val Gly Val Pro
                405                 410                 415
Gly Val Gly Val Pro Gly Val Gly Val Pro Gly Val Gly Val Pro Gly
                420                 425                 430
Val Gly Val Pro Gly Val Gly Val Pro Gly Val Gly Val Pro Gly Val
                435                 440                 445
Gly Val Pro Gly Val Gly Val Pro Gly Val Gly Val Pro Gly Val Gly
                450                 455                 460
Gly Ala Gly Ala Gly Ser Gly Ala Gly Ala Gly Ser Gly Ala Gly Ala
465                 470                 475                 480
Gly Ser Gly Ala Gly Ala Gly Ser Gly Ala Gly Ala Gly Ser Gly Ala
                485                 490                 495
Gly Ala Gly Ser Gly Ala Gly Ala Gly Ser Gly Ala Gly Ala Gly Ser
                500                 505                 510
Val Pro Gly Val Gly Val Pro Gly Val Gly Val Pro Gly Val Gly Val
                515                 520                 525
Pro Gly Val Gly Val Pro Gly Val Gly Val Pro Gly Val Gly Val Pro
                530                 535                 540
Gly Val Gly Val Pro Gly Val Gly Val Pro Gly Val Gly Val Pro Gly
545                 550                 555                 560
Val Gly Val Pro Gly Val Gly Val Pro Gly Val Gly Val Pro Gly Val
                565                 570                 575
Gly Val Pro Gly Val Gly Val Pro Gly Val Gly Val Pro Gly Val Gly
                580                 585                 590
Gly Ala Gly Ala Gly Ser Gly Ala Gly Ala Gly Ser Gly Ala Gly Ala
                595                 600                 605
Gly Ser Gly Ala Gly Ala Gly Ser Gly Ala Gly Ala Gly Ser Gly Ala
                610                 615                 620
Gly Ala Gly Ser Gly Ala Gly Ala Gly Ser Gly Ala Gly Ala Gly Ser
625                 630                 635                 640
Val Pro Gly Val Gly Val Pro Gly Val Gly Val Pro Gly Val Gly Val
                645                 650                 655
Pro Gly Val Gly Val Pro Gly Val Gly Val Pro Gly Val Gly Val Pro
                660                 665                 670
Gly Val Gly Val Pro Gly Val Gly Val Pro Gly Val Gly Val Pro Gly
                675                 680                 685
Val Gly Val Pro Gly Val Gly Val Pro Gly Val Gly Val Pro Gly Val
                690                 695                 700
Gly Val Pro Gly Val Gly Val Pro Gly Val Gly Val Pro Gly Val Gly
705                 710                 715                 720
Gly Ala Gly Ala Gly Ser Gly Ala Gly Ala Gly Ser Gly Ala Gly Ala
                725                 730                 735
Gly Ser Gly Ala Gly Ala Gly Ser Gly Ala Gly Ala Gly Ser Gly Ala
                740                 745                 750
```

-continued

```
Gly Ala Gly Ser Gly Ala Gly Ala Gly Ser Gly Ala Gly Ser
            755                 760                 765

Val Pro Gly Val Gly Val Pro Gly Val Gly Val Pro Gly Val Gly Val
    770                 775                 780

Pro Gly Val Gly Val Pro Gly Val Gly Val Pro Gly Val Gly Val Pro
785                 790                 795                 800

Gly Val Gly Val Pro Gly Val Gly Val Pro Gly Val Gly Val Pro Gly
                805                 810                 815

Val Gly Val Pro Gly Val Gly Val Pro Gly Val Gly Val Pro Gly Val
            820                 825                 830

Gly Val Pro Gly Val Gly Val Pro Gly Val Gly Val Pro Gly Val Gly
        835                 840                 845

Gly Ala Gly Ala Gly Ser Gly Ala Gly Ala Gly Ser Gly Ala Gly Ala
    850                 855                 860

Gly Ser Gly Ala Gly Ala Gly Ser Gly Ala Gly Ala Gly Ser Gly Ala
865                 870                 875                 880

Gly Ala Gly Ser Gly Ala Gly Ala Gly Ser Gly Ala Gly Ala Gly Ser
                885                 890                 895

Val Pro Gly Val Gly Val Pro Gly Val Gly Val Pro Gly Val Gly Val
            900                 905                 910

Pro Gly Val Gly Val Pro Gly Val Gly Val Pro Gly Val Gly Val Pro
        915                 920                 925

Gly Val Gly Val Pro Gly Val Gly Val Pro Gly Val Gly Val Pro Gly
    930                 935                 940

Val Gly Val Pro Gly Val Gly Val Pro Gly Val Gly Val Pro Gly Val
945                 950                 955                 960

Gly Val Pro Gly Val Gly Val Pro Gly Val Gly Val Pro Gly Val Gly
                965                 970                 975

Gly Ala Gly Ala Gly Ser Gly Ala Gly Ala Gly Ser Gly Ala Gly Ala
            980                 985                 990

Gly Ser Gly Ala Gly Ala Gly Ser Gly Ala Gly Ala Gly Ser Gly Ala
        995                1000                1005

Gly Ala Gly Ser Gly Ala Gly Ala Gly Ser Gly Ala Gly Ala Gly Ser
   1010                1015                1020
```

(2) INFORMATION FOR SEQ ID NO:32:

(i) SEQUENCE CHARACTERISTICS:
        (A) LENGTH: 1040 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:32:

```
Val Pro Gly Val Gly Val Pro Gly Val Gly Val Pro Gly Val Gly Val
1               5                  10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80
```

-continued

```
Val Pro Gly Val Gly Val Pro Gly Val Gly Val Pro Gly Val Gly Val
                 85                  90                  95
Pro Gly Val Gly Val Pro Gly Val Gly Val Pro Gly Val Gly Val Pro
            100                 105                 110
Gly Val Gly Val Pro Gly Val Gly Val Pro Gly Val Gly Val Pro Gly
        115                 120                 125
Val Gly Val Pro Gly Val Gly Val Pro Gly Val Gly Val Pro Gly Val
    130                 135                 140
Gly Val Pro Gly Val Gly Val Pro Gly Val Gly Val Pro Gly Val Gly
145                 150                 155                 160
Gly Ala Gly Ala Gly Ser Gly Ala Gly Ala Gly Ser Gly Ala Gly Ala
                165                 170                 175
Gly Ser Gly Ala Gly Ala Gly Ser Gly Ala Gly Ala Gly Ser Gly Ala
            180                 185                 190
Gly Ala Gly Ser Gly Ala Gly Ala Gly Ser Gly Ala Gly Ala Gly Ser
        195                 200                 205
Val Pro Gly Val Gly Val Pro Gly Val Gly Val Pro Gly Val Gly Val
    210                 215                 220
Pro Gly Val Gly Val Pro Gly Val Gly Val Pro Gly Val Gly Val Pro
225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Val Pro Gly Val
            260                 265                 270
Gly Val Pro Gly Val Gly Val Pro Gly Val Gly Val Pro Gly Val Gly
        275                 280                 285
Val Pro Gly Val Gly Val Pro Gly Val Gly Val Pro Gly Val Gly Val
    290                 295                 300
Pro Gly Val Gly Val Pro Gly Val Gly Val Pro Gly Val Gly Val Pro
305                 310                 315                 320
Gly Val Gly Val Pro Gly Val Gly Val Pro Gly Val Gly Val Pro Gly
                325                 330                 335
Val Gly Val Pro Gly Val Gly Val Pro Gly Val Gly Val Pro Gly Val
            340                 345                 350
Gly Val Pro Gly Val Gly Val Pro Gly Val Gly Val Pro Gly Val Gly
        355                 360                 365
Gly Ala Gly Ala Gly Ser Gly Ala Gly Ala Gly Ser Gly Ala Gly Ala
    370                 375                 380
Gly Ser Gly Ala Gly Ala Gly Ser Gly Ala Gly Ala Gly Ser Gly Ala
385                 390                 395                 400
Gly Ala Gly Ser Gly Ala Gly Ala Gly Ser Gly Ala Gly Ala Gly Ser
                405                 410                 415
Val Pro Gly Val Gly Val Pro Gly Val Gly Val Pro Gly Val Gly Val
            420                 425                 430
Pro Gly Val Gly Val Pro Gly Val Gly Val Pro Gly Val Gly Val Pro
        435                 440                 445
Gly Val Gly Val Pro Gly Val Gly Val Pro Gly Val Gly Val Pro Gly
    450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Val Gly
                485                 490                 495
```

```
Val Pro Gly Val Gly Val Pro Gly Val Gly Pro Gly Val Gly Val
            500                 505                 510
Pro Gly Val Gly Val Pro Gly Val Gly Val Pro Gly Val Gly Val Pro
            515                 520                 525
Gly Val Gly Val Pro Gly Val Gly Val Pro Gly Val Gly Val Pro Gly
            530                 535                 540
Val Gly Val Pro Gly Val Gly Val Pro Gly Val Gly Val Pro Gly Val
545                 550                 555                 560
Gly Val Pro Gly Val Gly Val Pro Gly Val Gly Val Pro Gly Val Gly
            565                 570                 575
Gly Ala Gly Ala Gly Ser Gly Ala Gly Ala Gly Ser Gly Ala Gly Ala
            580                 585                 590
Gly Ser Gly Ala Gly Ala Gly Ser Gly Ala Gly Ala Gly Ser Gly Ala
            595                 600                 605
Gly Ala Gly Ser Gly Ala Gly Ala Gly Ser Gly Ala Gly Ala Gly Ser
            610                 615                 620
Val Pro Gly Val Gly Val Pro Gly Val Gly Val Pro Gly Val Gly Val
625                 630                 635                 640
Pro Gly Val Gly Val Pro Gly Val Gly Val Pro Gly Val Gly Val Pro
            645                 650                 655
Gly Val Gly Val Pro Gly Val Gly Val Pro Gly Val Gly Val Pro Gly
            660                 665                 670
Val Gly Val Pro Gly Val Gly Val Pro Gly Val Gly Val Pro Gly Val
            675                 680                 685
Gly Val Pro Gly Val Gly Val Pro Gly Val Gly Val Pro Gly Val Gly
            690                 695                 700
Val Pro Gly Val Gly Val Pro Gly Val Gly Val Pro Gly Val Gly Val
705                 710                 715                 720
Pro Gly Val Gly Val Pro Gly Val Gly Val Pro Gly Val Gly Val Pro
            725                 730                 735
Gly Val Gly Val Pro Gly Val Gly Val Pro Gly Val Gly Val Pro Gly
            740                 745                 750
Val Gly Val Pro Gly Val Gly Val Pro Gly Val Gly Val Pro Gly Val
            755                 760                 765
Gly Val Pro Gly Val Gly Val Pro Gly Val Gly Val Pro Gly Val Gly
            770                 775                 780
Gly Ala Gly Ala Gly Ser Gly Ala Gly Ala Gly Ser Gly Ala Gly Ala
785                 790                 795                 800
Gly Ser Gly Ala Gly Ala Gly Ser Gly Ala Gly Ala Gly Ser Gly Ala
            805                 810                 815
Gly Ala Gly Ser Gly Ala Gly Ala Gly Ser Gly Ala Gly Ala Gly Ser
            820                 825                 830
Val Pro Gly Val Gly Val Pro Gly Val Gly Val Pro Gly Val Gly Val
            835                 840                 845
Pro Gly Val Gly Val Pro Gly Val Gly Val Pro Gly Val Gly Val Pro
            850                 855                 860
Gly Val Gly Val Pro Gly Val Gly Val Pro Gly Val Gly Val Pro Gly
865                 870                 875                 880
Val Gly Val Pro Gly Val Gly Val Pro Gly Val Gly Val Pro Gly Val
            885                 890                 895
Gly Val Pro Gly Val Gly Val Pro Gly Val Gly Val Pro Gly Val Gly
            900                 905                 910
Val Pro Gly Val Gly Val Pro Gly Val Gly Val Pro Gly Val Gly Val
```

-continued

```
              915                 920                 925
Pro Gly Val Gly Val Pro Gly Val Gly Val Pro Gly Val Gly Val Pro
    930                 935                 940
Gly Val Gly Val Pro Gly Val Gly Val Pro Gly Val Gly Val Pro Gly
945                 950                 955                 960
Val Gly Val Pro Gly Val Gly Val Pro Gly Val Gly Val Pro Gly Val
                965                 970                 975
Gly Val Pro Gly Val Gly Val Pro Gly Val Gly Val Pro Gly Val Gly
            980                 985                 990
Gly Ala Gly Ala Gly Ser Gly Ala Gly Ser Gly Ala Gly Ala
        995                 1000                1005
Gly Ser Gly Ala Gly Ala Gly Ser Gly Ala Gly Ala Gly Ser Gly Ala
    1010                1015                1020
Gly Ala Gly Ser Gly Ala Gly Ala Gly Ser Gly Ala Gly Ala Gly Ser
1025                1030                1035                1040
```

(2) INFORMATION FOR SEQ ID NO:33:

(i) SEQUENCE CHARACTERISTICS:
        (A) LENGTH: 1169 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:33:

```
Gly Ala Gly Ala Gly Ser Gly Ala Gly Ala Gly Ser Gly Ala Gly Ala
1               5                   10                  15
Gly Ser Gly Ala Gly Ala Gly Ser Gly Ala Gly Ala Gly Ser Gly Ala
            20                  25                  30
Gly Ala Gly Ser Gly Ala Gly Ala Gly Ser Gly Ala Gly Ala Gly Ser
        35                  40                  45
Gly Ala Gly Ala Gly Ser Gly Ala Gly Ala Gly Ser Gly Ala Gly Ala
    50                  55                  60
Gly Ser Gly Ala Gly Ala Gly Ser Gly Ala Ala Val Thr Gly Arg Gly
65                  70                  75                  80
Asp Ser Pro Ala Ser Ala Ala Gly Tyr Gly Ala Gly Ala Gly Ser Gly
                85                  90                  95
Ala Gly Ala Gly Ser Gly Ala Gly Ala Gly Ser Gly Ala Gly Ala Gly
            100                 105                 110
Ser Gly Ala Gly Ala Gly Ser Gly Val Gly Val Gly Pro Gly Val Gly
        115                 120                 125
Val Gly Pro Gly Val Gly Val Gly Pro Gly Val Gly Val Gly Pro Gly
    130                 135                 140
Val Gly Val Gly Pro Gly Val Gly Val Gly Pro Gly Val Gly Val Gly
145                 150                 155                 160
Pro Gly Val Gly Val Gly Pro Gly Ala Gly Ala Gly Ser Gly Ala Gly
                165                 170                 175
Ala Gly Ser Gly Ala Gly Ala Gly Ser Gly Ala Gly Ala Gly Ser Gly
            180                 185                 190
Ala Gly Ala Gly Ser Gly Ala Gly Ala Gly Ser Gly Ala Gly Ala Gly
        195                 200                 205
Ser Gly Ala Gly Ala Gly Ser Gly Ala Gly Ala Gly Ser Gly Ala Gly
    210                 215                 220
Ala Gly Ser Gly Ala Gly Ala Gly Ser Gly Ala Gly Ala Gly Ser Gly
```

-continued

```
              225                 230                 235                 240
        Ala Ala Val Thr Gly Arg Gly Asp Ser Pro Ala Ser Ala Ala Gly Tyr
                        245                 250                 255
        Gly Ala Gly Ala Gly Ser Gly Ala Gly Ala Gly Ser Gly Ala Gly Ala
                        260                 265                 270
        Gly Ser Gly Ala Gly Ala Gly Ser Gly Ala Ala Gly Ser Gly Val
                    275                 280                 285
        Gly Val Gly Pro Gly Val Gly Val Gly Pro Gly Val Gly Val Gly Pro
                290                 295                 300
        Gly Val Gly Val Gly Pro Gly Val Val Gly Pro Gly Val Gly Val
        305                 310                 315                 320
        Gly Pro Gly Val Gly Val Gly Pro Gly Val Val Gly Pro Gly Ala
                        325                 330                 335
        Gly Ala Gly Ser Gly Ala Gly Ala Gly Ser Gly Ala Gly Ala Gly Ser
                        340                 345                 350
        Gly Ala Gly Ala Gly Ser Gly Ala Ala Gly Ser Gly Ala Gly Ala
                        355                 360                 365
        Gly Ser Gly Ala Gly Ala Gly Ser Gly Ala Gly Ala Gly Ser Gly Ala
                    370                 375                 380
        Gly Ala Gly Ser Gly Ala Gly Ala Gly Ser Gly Ala Gly Ala Gly Ser
        385                 390                 395                 400
        Gly Ala Gly Ala Gly Ser Gly Ala Ala Val Thr Gly Arg Gly Asp Ser
                        405                 410                 415
        Pro Ala Ser Ala Ala Gly Tyr Gly Ala Gly Ala Gly Ser Gly Ala Gly
                        420                 425                 430
        Ala Gly Ser Gly Ala Gly Ala Gly Ser Gly Ala Gly Ala Gly Ser Gly
                        435                 440                 445
        Ala Gly Ala Gly Ser Gly Val Gly Val Gly Pro Gly Val Gly Val Gly
                    450                 455                 460
        Pro Gly Val Gly Val Gly Pro Gly Val Gly Val Gly Pro Gly Val Gly
        465                 470                 475                 480
        Val Gly Pro Gly Val Gly Val Gly Pro Gly Val Gly Val Gly Pro Gly
                        485                 490                 495
        Val Gly Val Gly Pro Gly Ala Gly Ala Gly Ser Gly Ala Gly Ala Gly
                        500                 505                 510
        Ser Gly Ala Gly Ala Gly Ser Gly Ala Gly Ala Gly Ser Gly Ala Gly
                        515                 520                 525
        Ala Gly Ser Gly Ala Gly Ala Gly Ser Gly Ala Gly Ala Gly Ser Gly
                    530                 535                 540
        Ala Gly Ala Gly Ser Gly Ala Gly Ala Gly Ser Gly Ala Gly Ala Gly
        545                 550                 555                 560
        Ser Gly Ala Gly Ala Gly Ser Gly Ala Gly Ala Gly Ser Gly Ala Ala
                        565                 570                 575
        Val Thr Gly Arg Gly Asp Ser Pro Ala Ser Ala Ala Gly Tyr Gly Ala
                        580                 585                 590
        Gly Ala Gly Ser Gly Ala Gly Ala Gly Ser Gly Ala Gly Ala Gly Ser
                        595                 600                 605
        Gly Ala Gly Ala Gly Ser Gly Ala Gly Ala Gly Ser Gly Val Gly Val
                    610                 615                 620
        Gly Pro Gly Val Gly Val Gly Pro Gly Val Gly Val Gly Pro Gly Val
        625                 630                 635                 640
        Gly Val Gly Pro Gly Val Gly Val Gly Pro Gly Val Gly Val Gly Pro
                        645                 650                 655
```

-continued

```
Gly Val Gly Val Gly Pro Gly Val Gly Val Pro Gly Ala Gly Ala
            660                 665                 670
Gly Ser Gly Ala Gly Ala Gly Ser Gly Ala Gly Ala Gly Ser Gly Ala
            675                 680                 685
Gly Ala Gly Ser Gly Ala Gly Ala Gly Ser Gly Ala Gly Ala Gly Ser
            690                 695                 700
Gly Ala Gly Ala Gly Ser Gly Ala Gly Ala Gly Ser Gly Ala Gly Ala
705                 710                 715                 720
Gly Ser Gly Ala Gly Ala Gly Ser Gly Ala Gly Ala Gly Ser Gly Ala
            725                 730                 735
Gly Ala Gly Ser Gly Ala Ala Val Thr Gly Arg Gly Asp Ser Pro Ala
            740                 745                 750
Ser Ala Ala Gly Tyr Gly Ala Gly Ala Gly Ser Gly Ala Gly Ala Gly
            755                 760                 765
Ser Gly Ala Gly Ala Gly Ser Gly Ala Gly Ala Gly Ser Gly Ala Gly
            770                 775                 780
Ala Gly Ser Gly Val Gly Val Gly Pro Gly Val Gly Val Gly Pro Gly
785                 790                 795                 800
Val Gly Val Gly Pro Gly Val Gly Val Gly Pro Gly Val Gly Val Gly
            805                 810                 815
Pro Gly Val Gly Val Gly Pro Gly Val Gly Val Gly Pro Gly Val Gly
            820                 825                 830
Val Gly Pro Gly Ala Gly Ala Gly Ser Gly Ala Gly Ala Gly Ser Gly
            835                 840                 845
Ala Gly Ala Gly Ser Gly Ala Gly Ala Gly Ser Gly Ala Gly Ala Gly
            850                 855                 860
Ser Gly Ala Gly Ala Gly Ser Gly Ala Gly Ala Gly Ser Gly Ala Gly
865                 870                 875                 880
Ala Gly Ser Gly Ala Gly Ala Gly Ser Gly Ala Gly Ala Gly Ser Gly
            885                 890                 895
Ala Gly Ala Gly Ser Gly Ala Gly Ala Gly Ser Gly Ala Ala Val Thr
            900                 905                 910
Gly Arg Gly Asp Ser Pro Ala Ser Ala Ala Gly Tyr Gly Ala Gly Ala
            915                 920                 925
Gly Ser Gly Ala Gly Ala Gly Ser Gly Ala Gly Ala Gly Ser Gly Ala
            930                 935                 940
Gly Ala Gly Ser Gly Ala Gly Ala Gly Ser Gly Val Gly Val Gly Pro
945                 950                 955                 960
Gly Val Gly Val Gly Pro Gly Val Gly Val Gly Pro Gly Val Gly Val
            965                 970                 975
Gly Pro Gly Val Gly Val Gly Pro Gly Val Gly Val Gly Pro Gly Val
            980                 985                 990
Gly Val Gly Pro Gly Val Gly Val Gly Pro Gly Ala Gly Ala Gly Ser
            995                 1000                1005
Gly Ala Gly Ala Gly Ser Gly Ala Gly Ala Gly Ser Gly Ala Gly Ala
            1010                1015                1020
Gly Ser Gly Ala Gly Ala Gly Ser Gly Ala Gly Ala Gly Ser Gly Ala
1025                1030                1035                1040
Gly Ala Gly Ser Gly Ala Gly Ala Gly Ser Gly Ala Gly Ala Gly Ser
            1045                1050                1055
Gly Ala Gly Ala Gly Ser Gly Ala Gly Ala Gly Ser Gly Ala Gly Ala
            1060                1065                1070
```

-continued

```
Gly Ser Gly Ala Ala Val Thr Gly Arg Gly Asp Ser Pro Ala Ser Ala
            1075                1080                1085

Ala Gly Tyr Gly Ala Gly Ala Gly Ser Gly Ala Gly Ala Gly Ser Gly
        1090                1095                1100

Ala Gly Ala Gly Ser Gly Ala Gly Ala Gly Ser Gly Ala Gly Ala Gly
1105                1110                1115                1120

Ser Gly Val Gly Val Gly Pro Gly Val Gly Val Pro Gly Val Gly Val
            1125                1130                1135

Val Gly Pro Gly Val Gly Val Gly Pro Gly Val Gly Val Gly Pro Gly
            1140                1145                1150

Val Gly Val Gly Pro Gly Val Gly Val Gly Pro Gly Val Gly Val Gly
        1155                1160                1165

Pro
```

(2) INFORMATION FOR SEQ ID NO:34:

(i) SEQUENCE CHARACTERISTICS:
        (A) LENGTH: 312 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:34:

```
Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Val Gly Val Pro
            20                  25                  30

Gly Lys Gly Val Pro Gly Val Gly Val Pro Gly Val Gly Val Pro Gly
        35                  40                  45

Val Gly Val Pro Gly Ala Gly Ala Gly Ser Gly Ala Gly Ala Gly Ser
    50                  55                  60

Gly Val Gly Val Pro Gly Val Gly Val Pro Gly Val Gly Val Pro Gly
65                  70                  75                  80

Val Gly Val Pro Gly Lys Gly Val Pro Gly Val Gly Val Pro Gly Val
            85                  90                  95

Gly Val Pro Gly Val Gly Val Pro Gly Ala Gly Ala Gly Ser Gly Ala
            100                 105                 110

Gly Ala Gly Ser Gly Val Gly Val Pro Gly Val Gly Val Pro Gly Val
        115                 120                 125

Gly Val Pro Gly Val Gly Val Pro Gly Lys Gly Val Pro Gly Val Gly
    130                 135                 140

Val Pro Gly Val Gly Val Pro Gly Val Gly Val Pro Gly Ala Gly Ala
145                 150                 155                 160

Gly Ser Gly Ala Gly Ala Gly Ser Gly Val Gly Val Pro Gly Val Gly
            165                 170                 175

Val Pro Gly Val Gly Val Pro Gly Val Gly Val Pro Gly Lys Gly Val
            180                 185                 190

Pro Gly Val Gly Val Pro Gly Val Gly Val Pro Gly Val Gly Val Pro
        195                 200                 205

Gly Ala Gly Ala Gly Ser Gly Ala Gly Ala Gly Ser Gly Val Gly Val
    210                 215                 220

Pro Gly Val Gly Val Pro Gly Val Gly Val Pro Gly Val Gly Val Pro
225                 230                 235                 240

Gly Lys Gly Val Pro Gly Val Gly Val Pro Gly Val Gly Val Pro Gly
```

```
                    245                 250                 255
Val Gly Val Pro Gly Ala Gly Ala Gly Ser Gly Ala Gly Ala Gly Ser
                260                 265                 270
Gly Val Gly Val Pro Gly Val Gly Val Pro Gly Val Gly Val Pro Gly
                275                 280                 285
Val Gly Val Pro Gly Lys Gly Val Pro Gly Val Gly Val Pro Gly Val
                290                 295                 300
Gly Val Pro Gly Val Gly Val Pro
305                 310
```

(2) INFORMATION FOR SEQ ID NO:35:

(i) SEQUENCE CHARACTERISTICS:
        (A) LENGTH: 768 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:35:

```
Gly Val Gly Val Pro Gly Val Gly Val Pro Gly Val Gly Val Pro Gly
1               5                   10                  15
Val Gly Val Pro Gly Lys Gly Val Pro Gly Val Gly Val Pro Gly Val
                20                  25                  30
Gly Val Pro Gly Val Gly Val Pro Gly Ala Gly Ala Gly Ser Gly Ala
                35                  40                  45
Gly Ala Gly Ser Gly Ala Gly Ala Gly Ser Gly Ala Gly Ala Gly Ser
                50                  55                  60
Gly Val Gly Val Pro Gly Val Gly Val Pro Gly Val Gly Val Pro Gly
65                  70                  75                  80
Val Gly Val Pro Gly Lys Gly Val Pro Gly Val Gly Val Pro Gly Val
                85                  90                  95
Gly Val Pro Gly Val Gly Val Pro Gly Ala Gly Ala Gly Ser Gly Ala
                100                 105                 110
Gly Ala Gly Ser Gly Ala Gly Ala Gly Ser Gly Ala Gly Ala Gly Ser
                115                 120                 125
Gly Val Gly Val Pro Gly Val Gly Val Pro Gly Val Gly Val Pro Gly
                130                 135                 140
Val Gly Val Pro Gly Lys Gly Val Pro Gly Val Gly Val Pro Gly Val
145                 150                 155                 160
Gly Val Pro Gly Val Gly Val Pro Gly Ala Gly Ala Gly Ser Gly Ala
                165                 170                 175
Gly Ala Gly Ser Gly Ala Gly Ala Gly Ser Gly Ala Gly Ala Gly Ser
                180                 185                 190
Gly Val Gly Val Pro Gly Val Gly Val Pro Gly Val Gly Val Pro Gly
                195                 200                 205
Val Gly Val Pro Gly Lys Gly Val Pro Gly Val Gly Val Pro Gly Val
                210                 215                 220
Gly Val Pro Gly Val Gly Val Pro Gly Ala Gly Ala Gly Ser Gly Ala
225                 230                 235                 240
Gly Ala Gly Ser Gly Ala Gly Ala Gly Ser Gly Ala Gly Ala Gly Ser
                245                 250                 255
Gly Val Gly Val Pro Gly Val Gly Val Pro Gly Val Gly Val Pro Gly
                260                 265                 270
Val Gly Val Pro Gly Lys Gly Val Pro Gly Val Gly Val Pro Gly Val
```

-continued

```
                275                 280                 285
Gly Val Pro Gly Val Gly Val Pro Gly Ala Gly Ala Gly Ser Gly Ala
            290                 295                 300
Gly Ala Gly Ser Gly Ala Gly Ala Gly Ser Gly Ala Gly Ala Gly Ser
305                 310                 315                 320
Gly Val Gly Val Pro Gly Val Gly Val Pro Gly Val Gly Val Pro Gly
                325                 330                 335
Val Gly Val Pro Gly Lys Gly Val Pro Gly Val Gly Val Pro Gly Val
            340                 345                 350
Gly Val Pro Gly Val Gly Val Pro Gly Ala Gly Ala Gly Ser Gly Ala
            355                 360                 365
Gly Ala Gly Ser Gly Ala Gly Ala Gly Ser Gly Ala Gly Ala Gly Ser
            370                 375                 380
Gly Val Gly Val Pro Gly Val Gly Val Pro Gly Val Gly Val Pro Gly
385                 390                 395                 400
Val Gly Val Pro Gly Lys Gly Val Pro Gly Val Gly Val Pro Gly Val
                405                 410                 415
Gly Val Pro Gly Val Gly Val Pro Gly Ala Gly Ala Gly Ser Gly Ala
            420                 425                 430
Gly Ala Gly Ser Gly Ala Gly Ala Gly Ser Gly Ala Gly Ala Gly Ser
            435                 440                 445
Gly Val Gly Val Pro Gly Val Gly Val Pro Gly Val Gly Val Pro Gly
            450                 455                 460
Val Gly Val Pro Gly Lys Gly Val Pro Gly Val Gly Val Pro Gly Val
465                 470                 475                 480
Gly Val Pro Gly Val Gly Val Pro Gly Ala Gly Ala Gly Ser Gly Ala
                485                 490                 495
Gly Ala Gly Ser Gly Ala Gly Ala Gly Ser Gly Ala Gly Ala Gly Ser
            500                 505                 510
Gly Val Gly Val Pro Gly Val Gly Val Pro Gly Val Gly Val Pro Gly
            515                 520                 525
Val Gly Val Pro Gly Lys Gly Val Pro Gly Val Gly Val Pro Gly Val
            530                 535                 540
Gly Val Pro Gly Val Gly Val Pro Gly Ala Gly Ala Gly Ser Gly Ala
545                 550                 555                 560
Gly Ala Gly Ser Gly Ala Gly Ala Gly Ser Gly Ala Gly Ala Gly Ser
                565                 570                 575
Gly Val Gly Val Pro Gly Val Gly Val Pro Gly Val Gly Val Pro Gly
            580                 585                 590
Val Gly Val Pro Gly Lys Gly Val Pro Gly Val Gly Val Pro Gly Val
            595                 600                 605
Gly Val Pro Gly Val Gly Val Pro Gly Ala Gly Ala Gly Ser Gly Ala
            610                 615                 620
Gly Ala Gly Ser Gly Ala Gly Ala Gly Ser Gly Ala Gly Ala Gly Ser
625                 630                 635                 640
Gly Val Gly Val Pro Gly Val Gly Val Pro Gly Val Gly Val Pro Gly
                645                 650                 655
Val Gly Val Pro Gly Lys Gly Val Pro Gly Val Gly Val Pro Gly Val
            660                 665                 670
Gly Val Pro Gly Val Gly Val Pro Gly Ala Gly Ala Gly Ser Gly Ala
            675                 680                 685
Gly Ala Gly Ser Gly Ala Gly Ala Gly Ser Gly Ala Gly Ala Gly Ser
            690                 695                 700
```

-continued

Gly Val Gly Val Pro Gly Val Gly Val Pro Gly Val Gly Val Pro Gly
705                 710                 715                 720

Val Gly Val Pro Gly Lys Gly Val Pro Gly Val Gly Val Pro Gly Val
                725                 730                 735

Gly Val Pro Gly Val Gly Val Pro Gly Ala Gly Ala Gly Ser Gly Ala
            740                 745                 750

Gly Ala Gly Ser Gly Ala Gly Ala Gly Ser Gly Ala Gly Ala Gly Ser
        755                 760                 765

(2) INFORMATION FOR SEQ ID NO:36:

(i) SEQUENCE CHARACTERISTICS:
        (A) LENGTH: 696 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:36:

Gly Ala Gly Ala Gly Ser Gly Val Gly Val Pro Gly Val Gly Val Pro
1               5                   10                  15

Gly Val Gly Val Pro Gly Val Gly Val Pro Gly Lys Gly Val Pro Gly
            20                  25                  30

Val Gly Val Pro Gly Val Gly Val Pro Gly Val Gly Val Pro Gly Ala
        35                  40                  45

Gly Ala Gly Ser Gly Ala Gly Ala Gly Ser Gly Ala Gly Ala Gly Ser
    50                  55                  60

Gly Val Gly Val Pro Gly Val Gly Val Pro Gly Val Gly Val Pro Gly
65                  70                  75                  80

Val Gly Val Pro Gly Lys Gly Val Pro Gly Val Gly Val Pro Gly Val
                85                  90                  95

Gly Val Pro Gly Val Gly Val Pro Gly Ala Gly Ala Gly Ser Gly Ala
            100                 105                 110

Gly Ala Gly Ser Gly Ala Gly Ala Gly Ser Gly Val Gly Val Pro Gly
        115                 120                 125

Val Gly Val Pro Gly Val Gly Val Pro Gly Val Gly Val Pro Gly Lys
    130                 135                 140

Gly Val Pro Gly Val Gly Val Pro Gly Val Gly Val Pro Gly Val Gly
145                 150                 155                 160

Val Pro Gly Ala Gly Ala Gly Ser Gly Ala Gly Ala Gly Ser Gly Ala
                165                 170                 175

Gly Ala Gly Ser Gly Val Gly Val Pro Gly Val Gly Val Pro Gly Val
            180                 185                 190

Gly Val Pro Gly Val Gly Val Pro Gly Lys Gly Val Pro Gly Val Gly
        195                 200                 205

Val Pro Gly Val Gly Val Pro Gly Val Gly Val Pro Gly Ala Gly Ala
    210                 215                 220

Gly Ser Gly Ala Gly Ala Gly Ser Gly Ala Gly Ala Gly Ser Gly Val
225                 230                 235                 240

Gly Val Pro Gly Val Gly Val Pro Gly Val Gly Val Pro Gly Val Gly
                245                 250                 255

Val Pro Gly Lys Gly Val Pro Gly Val Gly Val Pro Gly Val Gly Val
            260                 265                 270

Pro Gly Val Gly Val Pro Gly Ala Gly Ala Gly Ser Gly Ala Gly Ala
        275                 280                 285

-continued

```
Gly Ser Gly Ala Gly Ala Gly Ser Gly Val Gly Val Pro Gly Val Gly
        290                 295                 300
Val Pro Gly Val Gly Val Pro Gly Val Gly Val Pro Gly Lys Gly Val
305                 310                 315                 320
Pro Gly Val Gly Val Pro Gly Val Gly Val Pro Gly Val Gly Val Pro
                325                 330                 335
Gly Ala Gly Ala Gly Ser Gly Ala Gly Ala Gly Ser Gly Ala Gly Ala
                340                 345                 350
Gly Ser Gly Val Gly Val Pro Gly Val Gly Val Pro Gly Val Gly Val
                355                 360                 365
Pro Gly Val Gly Val Pro Gly Lys Gly Val Pro Gly Val Gly Val Pro
        370                 375                 380
Gly Val Gly Val Pro Gly Val Gly Val Pro Gly Ala Gly Ala Gly Ser
385                 390                 395                 400
Gly Ala Gly Ala Gly Ser Gly Ala Gly Ala Gly Ser Gly Val Gly Val
                405                 410                 415
Pro Gly Val Gly Val Pro Gly Val Gly Val Pro Gly Val Gly Val Pro
                420                 425                 430
Gly Lys Gly Val Pro Gly Val Gly Val Pro Gly Val Gly Val Pro Gly
        435                 440                 445
Val Gly Val Pro Gly Ala Gly Ala Gly Ser Gly Ala Gly Ala Gly Ser
450                 455                 460
Gly Ala Gly Ala Gly Ser Gly Val Gly Val Pro Gly Val Gly Val Pro
465                 470                 475                 480
Gly Val Gly Val Pro Gly Val Gly Val Pro Gly Lys Gly Val Pro Gly
                485                 490                 495
Val Gly Val Pro Gly Val Gly Val Pro Gly Val Gly Val Pro Gly Ala
                500                 505                 510
Gly Ala Gly Ser Gly Ala Gly Ala Gly Ser Gly Ala Gly Ala Gly Ser
        515                 520                 525
Gly Val Gly Val Pro Gly Val Gly Val Pro Gly Val Gly Val Pro Gly
        530                 535                 540
Val Gly Val Pro Gly Lys Gly Val Pro Gly Val Gly Val Pro Gly Val
545                 550                 555                 560
Gly Val Pro Gly Val Gly Val Pro Gly Ala Gly Ala Gly Ser Gly Ala
                565                 570                 575
Gly Ala Gly Ser Gly Ala Gly Ala Gly Ser Gly Val Gly Val Pro Gly
                580                 585                 590
Val Gly Val Pro Gly Val Gly Val Pro Gly Val Gly Val Pro Gly Lys
        595                 600                 605
Gly Val Pro Gly Val Gly Val Pro Gly Val Gly Val Pro Gly Val Gly
        610                 615                 620
Val Pro Gly Ala Gly Ala Gly Ser Gly Ala Gly Ala Gly Ser Gly Ala
625                 630                 635                 640
Gly Ala Gly Ser Gly Val Gly Val Pro Gly Val Gly Val Pro Gly Val
                645                 650                 655
Gly Val Pro Gly Val Gly Val Pro Gly Lys Gly Val Pro Gly Val Gly
                660                 665                 670
Val Pro Gly Val Gly Val Pro Gly Val Gly Val Pro Gly Ala Gly Ala
        675                 680                 685
Gly Ser Gly Ala Gly Ala Gly Ser
        690                 695
```

SYNTHETIC PROTEINS FOR IN VIVO DRUG DELIVERY AND TISSUE AUGMENTATION

CROSS-REFERENCE TO RELATED APPLICATIONS

This application is a continuation-in-part of U.S. application Ser. No. 08/212,237, filed Mar. 11, 1994, now U.S. Pat. No. 5,606,019.

FIELD OF THE INVENTION

The field of this invention is the production and use of bioresorbable polypeptide polymers. More specifically, the present invention is directed to the use of bioresorbable polypeptide polymers for the controlled release of biologically active compounds in vivo and for altering the physical dimensions of a body tissue.

BACKGROUND OF THE INVENTION

The rate at which an implanted material resorbs or biodegrades within the body can be a major factor in determining its utility as a biomaterial. So called inert materials, such as metals, ceramics and plastics have been shown to be useful for permanent implants. However, in applications in which a device serves as an aid to healing or as a temporary aid in surgical repair, a resorbable material has the advantage of not having to be removed, once healing has occurred. Resorbable sutures and staples, bone pins and screws, wound dressings, and injectable drug delivery systems or depots are examples of such devices. However, there are very few materials available today which have the physical, chemical and biological properties necessary for the fabrication of medical devices, which must degrade and resorb in the body without detrimental consequences.

Various synthetic organic polymers have found use, such as polylactides, polyglycolides, polyanhydrides and polyorthoesters, which degrade in the body by hydrolysis. Collagen, glycosaminoglycans and hyaluronic acid are examples of natural implantable materials which resorb at least partially by enzymatic degradation. However, the rates of resorption are limited to the nature of the particular material and modifications can change the rate of resorption, but at the same time may adversely affect the desired properties of the product.

Illustrative of efforts to vary resorption characteristics by compositional changes are synthetic resorbable sutures composed of copolymers of lactide and glycolide. By varying the ratio of lactic acid to glycolic acid, the rate of resorption may be varied. Unfortunately, rapidly resorbing compositions tend to be soft and weak. Slow resorbing compositions are stiff and string. However, the hydrolytic resorption of these sutures produces acid buffered by the tissue medium, where erosion occurs at the polymer surface. In addition, hydrolysis may occur internally, where the resulting acid catalyzes and accelerates the degradation of the polymer. Thus, internal pockets of degradation can lead to rapid and catastrophic failure of mechanical properties.

There is, therefore, a need for products which can be used in the production of implantable devices. Such products should have the desired mechanical properties of tensile strength, elasticity, formability, and the like, provide for controlled resorption, and be physiologically acceptable. Moreover, such products should allow for ease of administration for a variety of in vivo indications including drug delivery and tissue augmentation.

Relevant Literature

U.S. Pat. No. 5,243,038 describes the preparation of high molecular weight, protein polymers and copolymers comprising long segments of small repeating units. Bioactive Polymeric Systems, Gebelein, C. G. and Carraher, C. E., eds., Plenum Press, New York, 1985; Contemporary Biomaterials, Boretos, John W. and Eden, Murray, eds., Noyes Publications, New Jersey, 1984; and Concise Guide to Biomedical Polymers: Their Design, Fabrication and Molding, Boretos, John W., Thomas pub., Illinois, 1973, describe compositions, characteristics, and applications of biomaterials.

SUMMARY OF THE INVENTION

In one aspect, the present invention is directed to a method for delivering a biologically active substance to a localized site in vivo, wherein the method comprises:

administering a composition to the localized site, said composition comprising (i) a protein polymer of at least 15 kD which comprises alternating blocks of at least 2 units each of (a) an amino acid sequence of from about 3 to 30 amino acids which promotes protein crystallization and (b) an amino acid sequence element selected from the group consisting of an elastin-like element, a collagen-like element or a keratin-like element and (ii) a biologically active substance; wherein said composition acquires a non-liquid form under physiological conditions and wherein said biologically active substance is delivered from said non-liquid form to said localized site. In preferred embodiments of the described method, the amino acid sequence which promotes protein crystallization is GAGAGS (SEQ ID NO:1) or SGAGAG (SEQ ID NO:2) and/or the amino acid sequence element (b) above is the amino acid sequence VPGG (SEQ ID NO:3), APGVGV (SEQ ID NO:4), GXGVP (SEQ ID NO:5) or VPGXG (SEQ ID NO:6) where the amino acid X is valine, lysine, histidine, glutamic acid, arginine, aspartic acid, serine, tryptophan, tyrosine, phenylalanine, leucine, glutamine, asparagine, cysteine or methionine, more preferably valine or lysine.

The method may provide for delivery of a biologically active substance over an extended period of time. Biologically active substances which find use herein are formulated into compositions comprising the protein polymer of interest and include, for example, proteins, nucleic acids, antitumor agents, analgesics, antibiotics, anti-inflammatory compounds (both steroidal and non-steroidal), hormones, vaccines, labeled substances, and the like. The use of additional components in the compositions which, for example, affect the rate at which the polymer composition polymerizes into a non-liquid form is also provided.

In another aspect, the present invention provides compositions which are useful in the above described method.

In yet another aspect, the present invention provides a method for altering the physical dimensions of a body tissue in a mammal, wherein the method comprises:

introducing into or onto said body tissue a composition comprising a protein polymer of at least 15 kD which comprises alternating blocks of at least 2 units each of (a) an amino acid sequence of from about 3 to 30 amino acids which promotes protein crystallization and (b) an amino acid sequence element selected from the group consisting of an elastin-like element, a collagen-like element or a keratin-like element;

wherein said composition acquires a non-liquid form under physiological conditions.

In preferred embodiments of the described method, the amino acid sequence which promotes protein crystallization is GAGAGS (SEQ ID NO:1) or SGAGAG (SEQ ID NO:2) and/or the amino acid sequence element (b) above is the amino acid sequence VPGG (SEQ ID NO:3), APGVGV (SEQ ID NO:4), GXGVP (SEQ ID NO:5) or VPGXG (SEQ ID NO:6) where the amino acid X is valine, lysine, histidine, glutamic acid, arginine, aspartic acid, serine, tryptophan, tyrosine, phenylalanine, leucine, glutamine, asparagine, cysteine or methionine. more preferably valine or lysine.

Other aspects will be readily apparent to the skilled artisan upon a reading of the present specification.

DESCRIPTION OF SPECIFIC EMBODIMENTS

Figure 1:
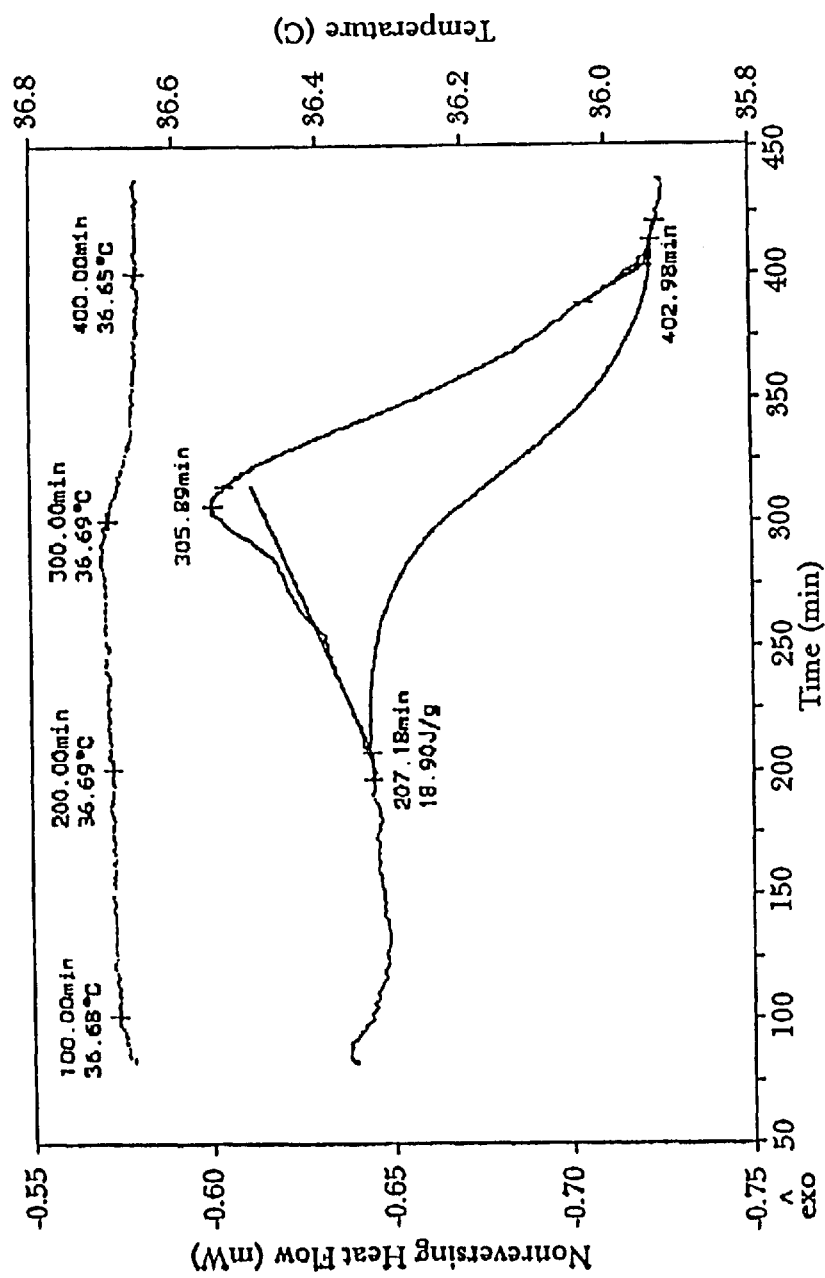
FIG. 1. Modulated Differential Scanning Calorimetry of 33% (w/w) SELP8K Solution at 37° C. The amplitude and period of the sinusoidal heating function was 1.0° C. and 60 seconds, respectively. Upper trace corresponds to MDSC cell temperature shown on the right-side ordinate axis. Lower curve corresponds to the absolute magnitude of the non-reversing heat flow (left-side ordinate axis) and shows integration of crystallization exotherm using a heat capacity-corrected baseline. This integration includes the mass of both the polymer and the 1×PBS, 20.4780 mg.

Compositions and methods are provided for delivering a biologically active substance of interest to a localized site in vivo, wherein the methods employ compositions comprising recombinant novel repetitive protein polymers which have alternating blocks of amino acid sequences which (1) promote protein crystallization or (2) are selected from either elastin-like, collagen-like or keratin-like amino acid sequence elements. Preferably, the alternating blocks are amino acid seqeunce units which are identical or similar to those found in natural silks and elastins; these latter polymers being referred to herein as "SELPs" in that they are comprised of silk-like and elastin-like amino acid sequence blocks. Also provided herein are methods for altering the physical dimensions of a body tissue which comprise employing the above described novel protein polymers. By protein polymer is meant a polypeptide chain comprised of amino acids which are arranged in a sequential manner within a block or set of blocks that are repeated in tandem producing a high molecular weight repetitive protein. Particularly, the units employed in the preferred SELP protein polymers described herein have the "silk-like" amino acid sequences GAGAGS (SEQ ID NO:1) or SGAGAG (SEQ ID NO:2) and the "elastin-like" amino acid sequences VPGG (SEQ ID NO:3), APGVGV (SEQ ID NO:4), VPGVG (SEQ ID NO:7) or GVGVP (SEQ ID NO:8), although some variations are permitted as will be described below, such as the particular order of the amino acids in the sequence and conservative substitutions, such as, but not limited to, replacing serine with threonine and glycine with alanine.

High molecular weight protein polymers are constructed from "monomer" segments which appear in a repetitive fashion in the polymer. Each monomer segment is comprised from alternating blocks of the above described amino acid sequence units. As such, a protein polymer as defined herein may generally be illustrated by the following formulas:

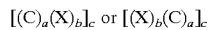

$$[(C)_a(X)_b]_c \text{ or } [(X)_b(C)_a]_c$$

where "X" represents an amino acid sequence element selected from the group consisting of an elastin-like, collagen-like or keratin-like unit and "b" represents the number of such units present in the monomer segment, "C" represents an amino acid sequence unit of from about 3 to 30 amino acid which promotes protein crystallization and "a" represents the number of such units present in the monomer segment and "c" represents the number of monomer units which are repeated in the protein polymer.

The protein polymers employed in the present invention will be at least about 15 kDa and generally not more than about 250 kDa, usually not more than about 175 kDa, more usually not more than about 125 kDa, preferably ranging from about 15 to 100 kDa and more preferably from about 50 to 90 kDa in size. In order to achieve repetitive protein polymers within these molecular weight ranges, the number of repetitive monomer segments incorporated into the polymer will provide for the desired molecular weight. In this regard, the number of monomer segments in the polymer can vary widely, depending upon the size of each individual monomer. Thus, the number of monomers may vary generally from about 2 to 100, usually from about 2 to 40, more usually ranging from about 6 to 20 and preferably from about 8 to 13.

Based upon the method of preparation, there may also be non-repetitive amino acid units at the N- and C-termini of the protein polymer. Usually, the terminal sequences will contribute fewer than ten number percent of the total amino acids, more usually fewer than five number percent of the total amino acids present in the polymer. Generally, the terminal amino acid sequences will range from about 0–125 amino acids, more usually from about 0–60 amino acids, where the total number of amino acids will generally not exceed about 100 amino acids, more usually not exceed about 50 amino acids.

For special applications, the protein polymers may also be modified by introducing intervening amino acid sequences between one or more monomer segments or the alternating block units which make up the monomer segment or by otherwise modifying one or more amino acid residues present in the polymer. Intervening sequences may include from about 1 to 60, usually about 3 to 40 amino acids, and may provide for a wide variety of properties including promotion of polymer chain interactions mediated by such things as hydrogen bonding, salt bridges and/or hydrophobic interactions. For example, by including amino acids which have chemically reactive sidechains, one may provide sites for linking a variety of chemically or physiologically active compounds, for cross-linking, for covalently bonding compounds which may change the rate of resorption, tensile properties, rate of release of an incorporated biologically active compound, or the like. Thus, amino acids such as cysteine, aspartic acid, glutamic acid, lysine and arginine may be incorporated in these intervening sequences. Alternatively, intervening sequences may provide for sequences that have physiological activity, such as cell binding, specific protein binding, enzyme substrates, specific receptor binding, and the like. In addition, one or more amino acid residues in the polymer may be modified, either chemically or otherwise, to provide for novel characteristics, such as novel polymerization rates, novel tensile strengths, novel rates of resorption in vivo, and the like. For example, hydroxyalkylation at various amino acid sites in the polymer may provide for such novel characteristics. In this manner, the useful properties of the basic protein may be greatly varied in accordance with the intended use, being tailored for specific applications.

For the protein polymers employed herein, the ratio of the average number of amino acid sequences elements selected from the group consisting of elastin-like, collagen-like and silk-like units to the average number of amino acid sequences which promote protein crystallization per monomer segment will be in the range of about 0.5, usually about 1 to 5. For the most part, there will be at least two protein crystallization units per monomer segment and not more than about 16, usually not more than about 12, preferably ranging from about 2 to 8 and more preferably from about 4 to 8. For the elastin-like, collagen-like or keratin-like amino acid sequence elements, there will usually be at least two per monomer segment, more usually at least about four, generally ranging from about 6 to 32, more usually from about 6 to 18 and preferably from about 6 to 16. Monomer segments are generally composed of multiple protein crystallization units followed by multiple elastin-like, collagen-like or keratin-like units or vice versa (as shown in the above formulas), however, insertion of one or more of one unit type within a run of multiple units of the other unit type may also be employed. The protein polymers which find use in the invention will generally range from about 15–80% of amino acids provided by the protein crystallization units.

For the most part, the "elastin-like" units employed herein have the amino acid sequence VPGG, APGVGV, GXGVP or VPGXG, where X is valine, lysine, histidine, glutamic acid, arginine, aspartic acid, serine, tryptophan, tyrosine, phenylalanine, leucine, glutamine, asparagine, cysteine or methionine, usually valine or lysine, preferably valine.

"Collagen-like" units contain the tandemly repeated amino acid triad GXO, where G is glycine and X and O are any amino acid except that X and O are selected such that the proline content in the triads of the polymer is less than about 45 number % (see U.S. patent application Ser. No. 08/642,255, filed May 2, 1996). A single "collagen-like unit" may comprise at least about 2 and not more than about 100 tandemly repeated triads, more usually not more than about 75, frequently not more than about 50, more frequently not more than about 25. Preferably, amino acids X and O are selected from the group consisting of alanine, isoleucine, valine, leucine, serine, threonine, asparagine, glutamine, lysine, arginine, aspartic acid, glutamic acid, histidine or proline.

"Keratin-like" units as defined herein have the so-called "heptad" repeat unit consisting of a seven amino acid long stretch with two positons separated by two amino acids, usually positions three and six, occupied consistently with hydrophobic, aliphatic or aromatic residues, e.g., AKLKLAE or AKLELAE (see U.S. Pat. No. 5,514,581, issued May 7, 1996).

Amino acid sequence units which promote protein crystallization are sequences from about 3 to 30 amino acids in length which, for the most part, possess relatively simple amino acids with relatively low molecular weight side chains including, for example, glycine, alanine, serine, threonine, cysteine and valine. Because these "protein crystallization units" possess, for the most part, relatively small molecular weight amino acids, they are capable of forming extended chain conformations such as β-sheets or β-strands that allow chains of the polypeptide to come into close proximity where hydrogen bonding may occur. These units allow the formation of ordered structures. Different protein crystallization units as such are known in the art and will find use in the present invention (e.g., Fossey et al., *Biopolymers* 31(13):1529–1542 (1991)). Preferably, these protein crystallization units are "silk-like" units which generally possess the amino acid sequence GAGAGS (SEQ ID NO:1) or SGAGAG (SEQ ID NO:2).

The amino acid sequence units and elements employed herein can also be modified by conservative substitution of amino acids at various positions in their sequences. For example, extensive examples of modified elastin-like blocks have been reported (Temperature of the inverse temperature transition for poly[(VPGVG)n(VPGXG)m](SEQ ID NOS:7 and 8), Urry et al., *Biopolymers* 32:1243–1250 (1992)). Substitutions of amino acids can impart changes in the chemical nature of the protein within which these blocks reside. For example, the replacement of the first valine in GVGVP (SEQ ID NO:8) with a more hydrophobic amino acid such as phenylalanine will decrease the lower critical solution temperature at which the elastin-like protein polymer is soluble. Replacing this valine with a more hydrophilic amino acid such as lysine will increase the lower critical solution temperature of the polymer solution. While these modified elastin-like blocks may affect certain chemical or physical properties, they can be readily chosen so as not to destroy the ability of protein polymers containing crystallizable silk-like blocks to aquire a non-liquid form, i.e., by gellation, solidification, and the like.

In the protein polymers which find use herein, by varying the ratio of the elastin-like, collagen-like or keratin-like elements and protein crystallization units, the length of the monomer segments comprising each of the units, the molecular weight, any intervening sequences, modifications to the individual repeating units, and the like, one can vary the tensile properties of the product only moderately, such as elasticity, stiffness, hardness, ease of processing, flexibility, the rate of resorption after in vivo administration and the rate at which a liquid composition of the SELP polymer acquires a non-liquid form. For example, faster resorption can be achieved by reducing the number of repeating silk-like units in the monomer segment below about 8 units or increasing the number of elastin-like units per monomer segment to greater than 8, individually or in combination. Faster gellation or crystallization of a liquid composition comprising the protein polymer can be obtained by increasing the concentration of the polymer in the liquid or increasing the relative number of protein crystallization units in the protein.

The protein polymers described herein may be prepared in accordance with the manner described in U.S. Pat. No. 5,243,038 and/or in PCT/US96/15306, both of which are expressly incorporated herein by reference. For example, one procedure involves synthesizing small segments of single stranded DNA of from about 15 to 150 nucleotides to provide a plurality of fragments which have cohesive ends, which may be ligated together to form a segment or a plurality of segments. The first dsDNA fragment is cloned to ensure the appropriate sequence, followed by the addition of successive fragments, which are in turn cloned and characterized, to ensure that the integrity of the sequence is retained. The fragments are joined together to form a monomer segment which, as described above, then becomes the major repeating building block of the polymer gene.

Alternatively, long single strands may be prepared, cloned and characterized, generally being of at least 100 nucleotides and up to about 300 nucleotides, where the two single strands are hybridized, cloned and characterized and may then serve as the monomer segment. The monomers may then be multimerized, having complementary termini, particularly cohesive ends, so that the SELP polymer will have two or more monomers present. The multimers may then be cloned in an appropriate vector and characterized to determine the number of monomers and the desired size polymer selected. Expression can be achieved in an expression host using transcriptional regulatory regions functional in the expression host. The expression host can be prokaryotic or eukaryotic, particularly bacterial, e.g. *E. coli, B. subtilis,* etc.; yeast, e.g. Saccharomyces, Neurospora, etc.; insect cells, plant cells, mammalian cells, and the like. If desired, a signal sequence may be provided for secretion of the polymer. A wide variety of signal sequences are known and have been used extensively for secreting proteins which are not normally secreted by the expression host.

After completion of expression, where the protein is retained in the host, the cells are disrupted and the product extracted from the lysate. Where the product is secreted, the product may be isolated from the supernatant. In either case, various techniques for purifying the products may be employed, depending upon whether the products are soluble or insoluble in the medium. Where insoluble, impurities may be extracted from the polymer, leaving the polymer intact. Where soluble, the polymer may be purified in accordance with conventional ways, such as extraction, chromatography, or the like.

The protein polymers described herein are useful for a variety of purposes. For example, one embodiment of the present invention is directed to use of the herein described protein polymers in methods for delivering biologically active substances to localized sites in vivo. Such methods take advantage of the fact that protein polymer compositions can by prepared in combination with a biologically active substance of interest in a liquid formulation which is capable of irreversibly acquiring a non-liquid form under physiological conditions (e.g., at normal body temperature after administration in vivo). Because the compositions acquire a non-liquid form in vivo, they are useful for releasing a biologically active substance incorporated therein to a localized site. Release of the biologically active substance from the non-liquid form appear to be a result of Fickian diffusion of the substance from the non-liquid form. By "non-liquid form" is meant a form which is recognized by those skilled in the art as a gel, a solid or other form which substantially lacks the properties of flow.

The transition from a liquid form to a non-liquid form occurs without the need for chemical crosslinking via chemical reaction or irradiation. In this way, no chemical changes to the protein polymer composition or to any biologically active substance contained in a composition thereof will occur. The rate of gelation, solidification or crystallization may be influenced by such things as the number of protein crystallization units in the polymer (the greater the relative number of protein crystallization units, the greater the rate of acquiring a non-liquid form in vivo), the concentration of the polymer (the greater the concentration of the protein polymer in the liquid composition, the greater the rate of acquiring a non-liquid form in vivo), temperature (the greater the temperature, the greater the rate of acquiring a non-liquid form in vivo) and other solution conditions. Generally, liquid protein polymer compositions will exhibit sufficient working time as a liquid to allow them to be loaded into a syringe and injected or otherwise introduced into the body. For the most part, compositions which acquire a non-liquid form in from about 30 seconds to about 500 minutes are preferred, more usually from about 1 minute to about 250 minutes, more usually from about 5 minutes to about 125 minutes. The rate of release of biologically active substances from the non-liquid form may depend on the molecular weight of the substance, its solubility in the polymer matrix, its charge, the composition of the polymer, including the relative number of protein crystallization units present therein and the conditions under which release takes place.

As such, using the present disclosure for guidance, polymer compositions may be routinely selected to provide for varying rates of release (i.e., quick release or sustained release over an extended period of time) of virtually any biologically active substance in vivo. Generally, polymer compositions which find use in the present invention have from about 5% (w/w) to about 50% (w/w) of the composition being protein polymer, usually from about 10% (w/w) to about 50% (w/w), more usually about 20% (w/w) to about 35% (w/w), preferably about 20% (w/w).

Because the transition from the liquid form to a non-liquid form is believed to be mediated by hydrogen bonding occurring between protein crystallization units present in the protein polymers, compounds which inhibit hydrogen bonding may be employed to decrease the rate at which the liquid form acquires a non-liquid form. Such compounds include, for example, urea, guanidine hydrochloride, dimethyl formamide, colloidal gold sol, aqueous lithium bromide and formic acid. The concentrations of such compounds which find use can be readily determined by the skilled artisan.

Moreover, additives which increase the rate at which the liquid composition acquires a non-liquid form may also find use in the present invention. Such "nucleating agents" or "accelerators" include, for example, pre-gelled protein polymers such as the SELP or SLP protein polymers described herein, preferably SLP3 or SLP4, aqueous solvents including, for example, ethanol, and the like. The construction and expression of protein polymers SLP3 and SLP4 are described in U.S. Pat. No. 5,243,038, issued Sep. 7, 1993 and have the following amino acid sequences.

SLP3
    DPVVLQRRDWENPGVTQLNRLAAHPP-
        FASDPMGAGS
    [(GAGAGS)$_9$ GAAGY]$_{18}$
    GAGAGSGAGAGSGAGAMDPGRYQL-
        SAGRYHYQLVWCQK (SEQ ID NO:9)
SLP4
    MDPVVLQRRDWENPGVTQLNRLAAHPP-
        FASDPMGAGS
    [(GAGAGS)$_6$]$_{27}$ (GAGAGS)$_4$
    GAGAMDPGRYQLSAGRYHYQLVWCQK (SEQ ID
        NO:10)

The concentrations of such compounds which find use can be readily determined by the skilled artisan.

Protein polymer compositions which find use for delivering biologically active substances to a localized site in vivo and for altering the physical dimensions of a body tissue as described below generally comprise alternating blocks of at least two repeated units each of elastin-like, collagen-like or keratin-like units and protein crystallization amino acid units per monomer.

By "biologically active substance" is meant any substance, agent or chemical which is capable of being released from a non-liquid form of a protein polymer-containing composition and which performs some desired function in vivo. Biologically active substances which find use in the present invention include, for example, such things as oligopeptides, proteins, immunoglobulins, growth factors, hormones, analgesics, antibiotics, vaccines, anti-inflammatory compounds (both steroidal and non-steroidal), nucleic acids including oligonucleotides, DNA, RNA, expression vectors, and the like, labeled compounds, chemical compounds, including anti-tumor and chemotherapeutic agents, liposomes, live cells, cellular organelles and sub-fractions of cells, and the like. For the most part, when proteins are employed as biologically active substances, those proteins will generally range in size from about 350 Da to about 500 kDa and will include oligopeptides from about 350 Da to about 10,000 Da, usually from about 1 kDa to 500 kDa and more usually from about 10 kDa to about 400 kDa. When nucleic acids are employed as biologically active substances, those nucleic acids will generally be from about 10 to 22,000 bases in length, usually from about 60 to 22,000 bases in length and preferably from about 150 to 10,000 bases in length.

When administered in vivo, the biologically active substance may exhibit a variety of therapeutic or diagnostic functions. For example, the biologically active substance may be labeled with a radioactive, fluorescein or other detectable marker and may be employed for both diagnostic and therapeutic purposes. Labels which find use in the present invention include, for example, contrast agents, radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{11}$C, or the like, fluorescently labeled compounds, etc. Methodology for attaching labels to different biologically active substances are well known in the art.

The protein polymer-containing compositions may also be used in combination with other materials, such as natural collagen, fibrinogen, and other natural proteins, hyaluronic acid, dextran, or other polysaccharides, or polyethylene oxide, polyhydroxyalkanoates, or other polyesters, to produce blended materials to provide a larger range of physical and biological properties, for applications, such as wound dressings or membranes for the prevention of surgical adhesions. For example, the protein polymer SELP3 combined with sodium hyaluronate, in equal proportions by weight, may be used to prepare a film, which compared to pure hyaluronate gels, exhibits greater mechanical toughness and a decreased resorption rate.

The present invention is also directed to the use of protein polymer-containing compositions for altering the physical dimensions of a body tissue in a mammal. For example, because of the ability of the herein described protein polymers and compositions thereof to dissolve in a biocompatible liquid which may irreversibly acquire a non-liquid form under normal physiological conditions, a liquid composition comprising one or more different protein polymers may be administered to virtually any site of interest in the body where it irreversibly acquires a non-liquid form for altering the physical dimensions of a body tissue including, for example, to fill a void, to augment an external physical feature or to otherwise alter the size and/or shape of a body tissue. Use of the above described protein polymer-containing compositions for altering the physical dimensions of a body tissue is advantageous in that the herein described polymers are biocompatible, display little or no adverse immunological reactivity, cause little or no undue tissue reaction and ultimately resorb harmlessly into the body. Their degradation products are for the most part simple amino acids which, as basic nutrients, can be reutilized.

The presently described protein polymers have good mechanical properties to form a wide variety of products. The protein polymers may be drawn, molded, cast, spun, extruded, or the like, in accordance with known ways for forming structures such as films, formed objects, fibers, or unformed structures, such as amorphous masses, and the like. Also, gels may be formed which may be shaped in a variety of ways, depending upon the particular application. The compositions can be sterilized by conventional ways to provide sterile products.

The subject protein polymer-containing compositions can be used to provide a wide variety of devices, such as membranes, sutures, staples, bone pins, screws, wound dressings, and the like, where the products may be formed prior to introduction into the body or in situ. The compositions as formed are found to provide the necessary mechanical properties for the particular applications, the resorption times can be controlled so as to ensure mechanical maintenance during the time required for structure integrity, and at the same time ensuring that the device or material need not be manually removed, since the material undergoes resorption.

The SELP polymers described herein can be formulated into liquid compositions by dissolving a polymer or a mixture thereof in a liquid which is preferably biocompatible. As such, protein polymer-containing solutions may be prepared in, for example, water, saline, phosphate buffered saline or other isotonic aqueous solution with or without other additives which may include, for example, mannitol, glucose, alcohol, vegetable oil, and the like.

The above described compositions may be administered or introduced to virtually any in vivo site by a number of means. Examples of administration techniques include, for example, injection by syringe into a site of interest, use of trocar or catheter, surgical implantation, placement into open wounds or other cavities, and the like.

The following examples are offered by way of illustration and not by limitation.

EXPERIMENTAL

A. Materials and Methods

*E. coli* strain EC3 harboring plasmids encoding each polymer employed herein were prepared in accordance with the methods described in U.S. Pat. No. 5,243,038 and PCT/US96/15306 (each of which is expressly incorporated herein by reference) with the following additions.

(1) Large Scale Plasmid Preparation

Large scale plasmid preparations from bacterial strains were obtained from overnight cultures using Qiagen Plasmid Kits (Qiagen-tips) and following the purification procedure recommended by the supplier. Phosphatase treatment of DNA was performed by resuspending ethanol precipitated DNA from a restriction enzyme digest in 20 mM Tris-HCl pH 8.0, 10 mM $MgCl_2$ to a final DNA concentration of 20 µg/ml. Shrimp alkaline phosphatase (SAP) was added at 2 U/µg of DNA and the mixture was incubated at 37° C. for one hr, heat inactivated for 20 min at 65° C. and then passed through a Probind filter (Millipore) and subsequently a Bio-Spin column. The DNA was then ethanol precipitated and resuspended in suitable buffer.

(2) Restriction Endonuclease Digestion

Restriction endonuclease (REN) digestion often employed the restriction endonuclease buffer supplied by the enzyme manufacturer. Whenever possible, the concentration of DNA was kept below 1 µg/25 µl. Incubation was at 37° C. for 1–4 hrs for most restriction endonucleases except for BalI, BanI and NaeI digestions which were incubated overnight.

(3) Agarose DNA Ligation

Agarose DNA ligation was performed as follows. The agarose sample was melted at 65° C., the temperature was then lowered to 37° C. and ligation buffer (5×=100 mM Tris-HCl, pH 7.5, 50 mM $MgCl_2$, 50 mM DTT, 1 mM ATP) was added; the tube was then placed at room temperature and ligase was added (1000 units T4 DNA ligase (NEB)), the reaction volume was usually 50 µl. The reaction was incubated at 15° C. for 16–18 hrs.

(4) DNA Purification with Filters and Columns

DNA purification employed various filters and columns. For use of the Ultrafree®-Probind filter unit ("Probind", Millipore), the DNA containing solution was applied to the filter unit and spun at 12,000 RPM for 30 seconds in a Sorvall Microspin 24S. For use of the Microcon-30 filter (Amicon), the DNA containing solution was washed by applying to the filter and exchanging twice with $H_2O$ by spinning at 12,000 RPM for 6 min in a microfuge. Finally, for use of the Bio-Spin 6 column ("Bio-Spin", BioRad), salts and glycerol were removed from the DNA solution by applying to the column, previously equilibrated in TEAB (triethyl ammonium bicarbonate pH 7.0), and spinning in a Sorvall RC5B centrifuge using an HB4 rotor at 2,500 RPM for 4 min.

Purification of DNA using Ultrafree®-MC Filter Unit was performed as follows. This procedure can be used for agarose slices up to 400 µl in size. After agarose gel electrophoresis, the DNA is visualized by ethidium bromide staining and the agarose block containing the DNA band of interest is excised. The agarose is then frozen at −20° C. for 1 hr; then quickly thawed at 37° C. for 5 min. The agarose is then thoroughly macerated. The pieces are then transferred into the sample cup of the filter unit and spun at 5,000×g in a standard microfuge for 20 min. The agarose is then resuspended in 200 µl of Tris-EDTA, or other buffer, and incubated at room temperature for 30 min to allow for elution of additional DNA from the gel. The mixture is then centrifuged for an additional 20 min at 10,000 RPM. The DNA is, at this point, in the filtrate tube separated from the agarose fragments and ready for subsequent DNA manipulations.

(5) Protein Expression Analysis

An overnight culture which had been grown at 30° C. was used to inoculate 50 ml of the LB media contained in a 250 ml flask. Kanamycin was added at a final concentration of 50 µg/ml and the culture was incubated with agitation (200 RPM) at 30° C. When the culture reached an $OD_{600}$ of 0.8, 40 ml were transferred to a new flask prewarmed at 42° C. and incubated at the same temperature for approximately 2 hrs. The cultures (30° C. and 42° C.) were chilled on ice and $OD_{600}$ was taken. Cells were collected by centrifugation and then divided in 1.0 $OD_{600}$ aliquots and used to perform western analysis using the appropriate antibodies. All SELP protein polymer molecular weights as specified herein were deduced from the gene sequence using the computer program DNA Strider for Apple Macintosh personal computer.

(6) Immunoblotting of Protein Gels

An alternative to the $^{125}$I-Protein A detection method described in U.S. Pat. No. 5,243,038 was also used. This method relied on a chemiluminescent signal activated by horseradish peroxidase (HRP). The chemiluminescent reagents are readily available from several suppliers such as Amersham and DuPont NEN. The western blot was prepared and blocked with BLOTTO. A number of methods were used to introduce the HRP reporter enzyme including, for example, a hapten/anti-hapten-HRP, a biotinylated antibody/streptavidin-HRP, a secondary reporter such as a goat or mouse anti-rabbit IgG-biotinylated/streptavidin-HRP, or a goat or mouse-anti rabbit IgG-HRP. These reagents were bought from different sources such as BioRad or Amersham and occasionally biotinylated antibodies were prepared in our laboratory using Biotin NHS from Vector Laboratories, Burlingame, Calif. (Cat. #SP-1200) following the procedure accompanying the product. The following is an example of a procedure used to detect the expression of protein polymers.

The blot was placed in 15 ml of BLOTTO solution containing biotinylated goat anti-rabbit IgG (BioRad) diluted in BLOTTO (1:7500) and gently agitated for 2 hrs at room temperature. The filter was then washed for 30 min with 3 changes of TSA (50 mM Tris-HCl pH 7.4, 0.9% NaCl, 0.2% sodium azide). The blot was then incubated for 20 min at room temperature with gentle rotation, in 20 ml of TBS (100 mM Tris Base, 150 mM NaCl, pH 7.5) HRP-Streptavidin (Amersham) diluted 1:1000 in TBS with 0.1% Tween 20. The blot was then washed three times for 5 min each in TBS with 0.3% Tween 20 and then three times for 5 min each in TBS with 0.1% Tween 20. The blot was then incubated for 1 min with gentle agitation in 12 ml of development solutions #1 an #2 (Amersham) equally mixed. The blot was removed from the development solution and autoradiographed.

(7) Amino Acid Analysis

As an alternative to the method described in U.S. Pat. No. 5,243,038, a modified Waters' Pico-Tag method was also used. Protein samples were hydrolyzed with 6 N constant boiling HCl at 110° C. for 24 hrs in vacuo. After reaction with PITC, amino acid derivatives were detected at 254 nm by HPLC reverse phase chromatography using ABI 140 B Dual Syringe Solvent Delivery System with Supelco C18 column (15 um, 2.1 mm×25 cm) and analyzed by Waters' Maxima 820 Data Acquisition System. The eluate A buffer is 0.14 M sodium acetate and eluate B buffer is 60% acetonitrile. Reference to these procedures is found in User's Manuals of Waters' Pico-Tag Method (1989 Millipore Corporation WM02, Rev. 1) and ABI 140 B Dual Syringe Solvent Delivery System (1992 Applied Biosystems, Inc. Part No. 1000-0567, Rev. C).

(8) In Vitro DNA Synthesis

In addition to the methods described in U.S. Pat. No. 5,243,038, for DNA synthesis of oligonucleotides longer then 100 bases, the synthesis cycle was changed from the protocol recommended by Applied Biosystems for the 381A DNA synthesizer. All the reagents used were fresh. All the reagents were supplied by Applied Biosystems except for the acetonitrile (Burdick and Jackson Cat#017-4 with water content less then 0.001%) and the 2000 Å pore size column (Glen Research). Due to the length of the oligo, interrupt pauses had to be inserted during the synthesis to allow changing the reagent bottles that emptied during synthesis. This interrupt pause was done at the cycle entry step and the pause was kept as short as possible. The washes after detritylation by TCA, through the beginning of each synthesis cycle, were increased from about 2× to 3× over the recommended time. The time allocated for the capping was also increased to limit truncated failure sequences. After the synthesis, the deprotection was done at 55° C. for 6 hrs. After desalting, the synthesized DNA was amplified using PCR.

(9) Dideoxy DNA Sequencing of Double Stranded Plasmid DNA

Plasmid DNA was prepared as described previously (Preparation of plasmid DNA from *E. coli*, Small Scale, Maniatis et al.) and sequenced by the primer extension method (Sanger et al., *Proc. Natl. Acad. Sci. USA* 74:5463–5467 (1977) and Biggin et al., *Proc. Natl. Acad. Sci. USA* 80:3963–3965 (1983)) using $^{35}$S-deoxyadenosine 5'-(alpha-thio)triphosphate (New England Nuclear) as label. Primers were synthesized using a DNA synthesizer as described previously. The sequencing reactions were done using Sequenase (United States Biochemicals) and the conditions were as recommended by the supplier. All sequences were run on 6 or 8% polyacrylamide gels containing 8 M urea (Sanger et al., *FEBS Letters* 87:107–110 (1978)). Storage and analysis of data utilized software from DNA Inspection lie, DNAid, MacVector DNA Strider or MacDNAsis for Apple Macintosh personal computer.

(10) PCR amplification:

The PCR reaction was performed in a 100 μl volume in a Perkin Elmer thin-walled Gene Amp™ reaction tube. Approximately 1 μl of each primer DNA (corresponding to a 0.1 μM final concentration) was added to 1×PCR buffer (supplied by Perkin Elmer as 10× solution), 200 μM of each dNT, 5U AmpliTaq, and several concentrations of the target DNA. Amplification was performed in a Perkin Elmer DNA Thermal cycler model 480 for 30 cycles with the following step cycles of 12 min each: 95° C., 62° C., and 72° C. Aliquots from the different reactions were analyzed by Agarose Gel Electrophoresis using 1.5% Low Melting Point agarose in 0.5×TA buffer. The reaction mixtures that gave the desired band were pooled and spun through an Ultrafree-Probind filter unit (Millipore) at 12,000 rpm for 30 seconds in a Sorvall Microspin 24S to remove the AmpliTaq enzyme. The buffer was then exchanged with $H_2O$ two times, using a Microcon-30 filter (Amicon) by spinning at 12,000 RPM for 6 min in a microfuge. Salts and glycerol were removed from the amplified dsDNA using a Bio-Spin 6 column (from BioRad) equilibrated in TEAB, in a Sorvall RC5B centrifuge using an HB4 rotor at 2,500 RPM for 4 min. The DNA was then concentrated in vacuo.

(11) Fermentation Conditions

In addition to the method disclosed in U.S. Pat. No. 5,243,038, medium A as shown in Table 1 was also employed as the fermentor medium. The starting volume in the case of 10 liter fermentation, is no less than 3 L, and in the case of an 80 liter fermentation, is no less than 30 liters.

If the fermentor starting volume is less than the final volume desired, then when the carbon source concentration reaches 1%, a concentrated solution (5×) of medium A is added to the fermentor in order to keep the carbon source concentration approximately 1%.

Other fermentors used for the expression of protein polymers were usually a 15 l MBR, 10 l working volume, or a 100 l New Brunswick Scientific, NBS Fermacell, model F-130 fermentor, 80 l working volume. The choice of the fermentor and its size is not critical. Any media used for the growth of *E. coli* can be used. The nitrogen source ranged from NZAmine to inorganic salts and the carbon source generally used was glycerol or glucose. All fermentations were done with the appropriate selection conditions imposed by the plasmid requirements (e.g. kanamycin, ampicillin, etc.).

The fermentation method used to express protein polymers in *E. coli* was the fed-batch method. The fed-batch method exploits the stage of cell growth where the organisms make a transition from exponential to stationary phase. This transition is often the result of either depletion of an essential nutrient or accumulation of a metabolic byproduct. When the transition is the result of nutrient depletion, the addition of nutrients to the system causes cell division to continue. One or more essential nutrients can incrementally be added to the fermentation vessel during the run, with the net volume increasing during the fermentation process. The result is a controlled growth rate where biomass and expression levels can be optimized. When the cell number in the culture has reached or is approaching a maximum, protein polymer production is induced by providing an appropriate physical or chemical signal, depending upon the expression system used. Production will then continue until the accumulated product reaches maximum levels (Fiestchko and Ritch, *Chem. Eng. Commun.* 45:229–240 (1986) and Seo and Bailey, *Biotechnol. Bioeng.* 28:1590–1594 (1986)).

TABLE 1

Fermentation Media Composition

| Medium A Constituent | g/l |
| --- | --- |
| (NH₄)SO₄ | 5.6 |
| K₂HPO₄ | 6.7 |
| MgSO₄.7H₂O | 7.8 |
| NaH₂PO₄.H₂O | 3.8 |
| EDTA | 0.98 |
| Trace Elements | 1 ml |
| Yeast Extract or NZ Amine | 50 |
| Glucose or glycerol | 20 |
| Kanamycin or ampicillin | $5 \times 10^{-3}$ |

B. Example 1

Specific SELP Gene Design, Construction and Expression

SELP polymers having at least one modified elastin-like unit in the repeating monomer having an amino acid sequence GKGVP (SEQ ID NO:11) have the designation "K" placed after the polymer number.

(1) SELPOK

The design, construction and expression of the SELPOK polymer is described in WO 96/34618, which is expressly incorporated herein by reference.

(2) SELP5

(a) Gene Construction

Plasmid pPSY1393 (U.S. Pat. No. 5,243,038) was digested with AvaI REN and the 60 bp fragment containing the ELP gene monomer was purified using agarose gel electrophoresis followed by NACS column purification and ligated in agarose with pSY1255 (U.S. Pat. No. 5,243,038) previously digested with AvaI REN. The products of the ligation mixture were transformed into *E. coli* strain HB101. Plasmid DNA from transformants was purified and analyzed by digestion using EcoRV and NruI RENs. Clones matching the correct restriction pattern were further analyzed by treatment with BanII with and without BanI RENs. Plasmid pPT0257 containing 3 repeats of the ELP gene fragment was used for subsequent constructions.

Plasmid DNA pSY1398 (U.S. Pat. No. 5,243,038) was treated with BanI REN. The digestion fragments were purified using agarose gel electrophoresis followed by NACS column purification. The DNA fragment containing the SLP4 gene monomer was ligated, using Hexamine Cobalt Chloride (HCC), with pPT0134 (U.S. Pat. No. 5,496,712) previously digested with FokI REN, then treated with phenol/chloroform followed by chloroform and then ethanol precipitated. The products of the ligation mixture were transformed into *E. coli* strain HB101. Plasmid DNA from transformants was purified and analyzed by digestion using NruI and XmnI RENs. Plasmid pPT0255 containing the SLP4 DNA gene fragment was used for subsequent constructions.

Plasmid DNA pPT0257 was treated with BanII REN. The digestion fragments were purified using low melting point agarose gel electrophoresis. The DNA fragment containing the SELP gene monomer was ligated, using agarose ligation conditions, with pPT0255 previously digested with BanII REN. The products of the ligation mixture were transformed into *E. coli* strain HB101. Plasmid DNA from transformants was purified and analyzed by digestion using NruI and EcoRV RENs. Plasmid pPT0260 containing the SELP5 DNA gene monomer (see Table 2) was used for subsequent polymerization.

TABLE 2

Nucleotide and Amino Acid Sequence of SELP5 Gene Monomer

| | | | | | | | | | | | | | | | | |
| --- | --- | --- | --- | --- | --- | --- | --- | --- | --- | --- | --- | --- | --- | --- | --- | --- |
| GGT | GCC | GGC | AGC | GGT | GCA | GGA | GCC | GGT | TCT | GGA | GCT | GGC | GCG | GGC | TCT | (SEQ ID NO.12) |
| G | A | G | S | G | A | G | A | G | S | G | A | G | A | G | S | (SEQ ID NO:13) |
| GGA | GTA | GGT | GTG | CCA | GGT | GTA | GGA | GTT | CCG | GGT | GTA | GGC | GTT | CCG | GGA | |
| G | V | G | V | P | G | V | G | V | P | G | V | G | V | P | G | |
| GTT | GGT | GTA | CCT | GGA | GTG | GGT | GTT | CCA | GGC | GTA | GGT | GTG | CCC | GGG | GTA | |
| V | G | V | P | G | V | G | V | P | G | V | G | V | P | G | V | |
| GGC | GTT | CCG | GGA | GTA | GGG | GTG | CCA | GGT | GTA | GGA | GTT | CCG | GGT | GTA | GGC | |
| G | V | P | G | V | G | V | P | G | V | G | V | P | G | V | G | |
| GTT | CCC | GGG | GTA | GGC | GTT | CCG | GGA | GTA | GGG | GTG | CCA | GGT | GTA | GGA | GTT | |
| V | P | G | V | G | V | P | G | V | G | V | P | G | V | G | V | |
| CCG | GGT | GTA | GGC | GTT | CCC | GGG | GTA | GGA | GTA | CCA | GGG | GTA | GGC | GTC | CCT | |
| P | G | V | G | V | P | G | V | G | V | P | G | V | G | V | P | |
| GGA | GCG | GGT | GCT | GGT | AGC | GGC | GCA | GGC | GCG | GGC | TCT | GGC | GCG | GGC | GCA | |
| G | A | G | A | G | S | G | A | G | A | G | S | G | A | G | A | |
| GGA | TCC | GGC | GCA | GGC | GCT | GGC | TCA | GGT | GCT | GGA | GCA | GGA | AGC | GGA | GCG | |
| G | S | G | A | G | A | G | S | G | A | G | A | G | S | G | A | |

(b) Polymer Gene Construction

Plasmid DNA from pPT0260 was digested with FokI REN and the digestion fragments were separated by agarose gel electrophoresis. The SELP5 gene monomer, 384 bp, was excised and purified by NACS column purification. The purified fragment was ligated, using HCC, with plasmid pSY1262 which has been described previously (U.S. Pat. No. 5,243,038). Plasmid DNA pSY1262 was digested with BanI REN, then treated with calf intestinal phosphatase (CIP) followed by phenol/chloroform and chloroform extractions and finally ethanol precipitated as previously described.

The products of this ligation reaction were transformed into E. coli strain HB101. Transformants were selected for resistance to kanamycin. Plasmid DNA from individual transformants was purified and analyzed for increase size due to SELP5 multiple DNA insertions. Several clones were obtained. Three clones were used for expression analysis. pPT0263, pPT0264, and pPT0265 contained polymer gene inserts of approximately 3.0, 2.6, and 2.2kb, respectively.

(c) Expression Analysis

E. coli strain HB101 containing plasmids pPT0263, pPT0264, and pPT0265 were grown as described. The proteins produced by these cells were analyzed by SDS-PAGE for detection of bands immunoreactive with anti-SLP or anti-ELP antibodies. Each clone produced a strong reactive band with observed apparent molecular weights of approximately 105, 90 and 70 Kd.

Amino Acid Sequence of SELP5 pPT0263

Amino Acids: 953 MW: 74,808 Dalton

MDPVVLQRRDWENPGVTQLNRLAAHPPFASDPM GAGS (GAGAGS)$_2$

[(GVGVP)$_{16}$ (GAGAGS)$_8$]$_6$ (GVGVP)$_{16}$ (GAGAGS)$_5$ GAGA

MDPGRYQLSAGRYHYQLVWCQK (SEQ ID NO:14)

(3) SELP8

(a) Gene Construction

Plasmid pSY1378 (U.S. Pat. No. 5,243,038) was digested with BanI REN and a fragment of the SLP4 gene was purified using agarose gel electrophoresis followed by NACS column purification. The DNA was ethanol precipitated in 2.5 M ammonium acetate and ligated with pPT0134 previously digested with FokI REN, extracted with phenol/chloroform and ethanol precipitated. The products of the ligation mixture were transformed into E. coli strain HB101. Plasmid DNA from transformants was purified and analyzed by digestion using NruI and XmnI RENs. Plasmid pPT0255 contained the desired restriction pattern and was used for subsequent constructions.

Plasmid DNA pPT0255 was treated with Cfr10I REN followed by RNAse. The digestion fragments were separated by agarose gel electrophoresis, the DNA was excised and self-ligated. The products of the ligation mixture were transformed into E. coli strain HB101. Plasmid DNA from transformants was purified and analyzed by digestion using NaeI and StuI RENs. Plasmid pPT0267 containing the desired deletion was used for subsequent constructions.

The following two oligonucleotide strands were synthesized and purified as described in Materials and Methods:

5'-CTGGAGCGGGAGCCTGCATGTACATCCGAGT-3' (SEQ ID NO:15)

3'-CGAGACCTCGCCCACGGACGTACATGTAG GCTCA-5' (SEQ ID NO:16)

The two oligonucleotide strands were annealed and ligated with the DNA of plasmid pPT0267 which has been previously digested with BanII and ScaI RENs, and purified by agarose gel electrophoresis followed by NACS column purification. The products of this ligation reaction were transformed into E. coli strain HB101. Plasmid DNA from transformants was purified and digested with DraI. Plasmid DNA from two clones that gave the correct digestion pattern was sequenced. One plasmid DNA, designated pPT0287, was found to be correct and chosen for further constructions.

Plasmid DNA pSY1298 (U.S. Pat. No. 5,243,038) was digested with BanII REN, and the SELP0 gene fragment was purified by agarose gel electrophoresis followed by NACS column purification and then ligated to pPT0287 digested with BanII REN. The enzyme was removed using phenol/chloroform extraction and the DNA was concentrated by ethanol precipitation. The products of the ligation mixture were transformed into E. coli strain HB101. Plasmid DNA from transformants was purified and analyzed by digestion using DraI REN. Plasmid DNA from the clones showing the correct restriction pattern was further digested with BanII, AhaII and StuI RENs. Plasmid pPT0289, contained the desired SELP8 monomer sequence (see Table 3).

TABLE 3

Nucleotide and Amino Acid Sequence of SELP8 Gene Monomer

BanI                                              BanII

GGT GCC GGT TCT GGA GCT GGC GCG GGC TCT GGA GTA GGT GTG CCA GGT   (SEQ ID NO:17)

G   A   G   S   G   A   G   A   G   S   G   V   G   V   P   G     (SEQ ID NO:18)

GTA GGA GTT CCG GGT GTA GGC GTT CCG GGA GTT GGT GTA CCT GGA GTG

V   G   V   P   G   V   G   V   P   G   V   G   V   P   G   V

SmaI

GGT GTT CCA GGC GTA GGT GTG CCC GGG GTA GGA GTA CCA GGG GTA GGC

G   V   P   G   V   G   V   P   G   V   G   V   P   G   V   G

BanII

GTC CCT GGA GCG GGT GCT GGT AGC GGC GCA GGC GCG GGC TCT GGA GCG

V   P   G   A   G   A   G   S   G   A   G   A   G   S   G   A (b) Polymer Gene Construction Plasmid DNA from pPT0289 was digested with BanI REN and the digestion fragments were separated by agarose gel electrophoresis. The SELP8 gene fragment, 192 bp, was excised and purified by NACS column. The purified fragment was ligated with plasmid pSY1262 that was digested with BanI REN. The DNA was then treated with SAP and then passed through a Millipore Probind filter by microfuging for 30 min at 12,000 rpm and ethanol precipitated.

The product of this ligation reaction was transformed into *E. coli* strain HB101. Transformants were selected for resistance to kanamycin. Plasmid DNA from individual transformants was purified and analyzed for increased size due to SELP8 multiple DNA insertions. Several clones were obtained. Three clones were used for expression analysis, pPT0301, pPT0302, and pPT0303 containing 4.4, 4.0 and 2.5 kb polymer gene inserts, respectively.

(c) Expression Analysis

*E. coli* strain HB101 containing plasmid pPT0303 was grown as described above. The proteins produced by these cells were analyzed by SDS-PAGE for detection of reactivity to SLP antibodies as described in Materials and Methods. A strong reactive band was observed with an apparent molecular weight of approximately 75 kD. The expected amino acid sequence of the SELP8 polymer gene product encoded by pPT0303 as deduced from the gene sequence is shown below:

Amino Acid Sequence of SELP8 pPT0303

Amino Acids: 889 MW: 69,977 daltons

MDPVVLQRRDWENPGVTQLNRLAAHPPFASDPM
GAGSGAGAGS
[(GVGVP)$_8$ (GAGAGS)$_4$]$_{12}$
(GVGVP)$_8$ (GAGAGS)$_2$
GAGAMDPGRYQLSAGRYHYQLVWCQK (SEQ ID NO:19)

(4) SELP8K

The design, construction and expression of the SELP8K polymer is described in WO 95/23611, which is expressly incorporated herein by reference.

(5) SELP9K (a) Gene Construction

A 93 base oligonucleotide strand coding for a portion of the gene monomer (Table 4) was synthesized using an Applied Biosystems DNA synthesizer model 381A and a 2000 Å synthesis column supplied by Glen Research. During the synthesis, the required interrupt-pause steps, for reagent bottle changes, were minimized. After the synthesis, the 93 base oligonucleotide strand was deprotected and cleaved from the column support by treatment with ammonium hydroxide at 55° C. for 6 hrs.

TABLE 4

Synthetic DNA Used in Construction of SELP9K Monomer (SEQ ID NO:20)
5' ATGGCAGCGAAAGGGGACCGGTGCCGGCGC

AGGTAGCGGAGCCGGTGCGGGCTCAAAAAG

GGCTCTGGTGCCTTTCCGCTAAAGTCCTGCCGT 3'

Two additional strands were synthesized and used as primers for PCR amplification. The synthesis and purification of these DNA primers was performed as described in Materials and Methods. The sequences of the two primers are:

5'-AAGAAGGAGATATCATATGGCAGCGAAAGG
GGACC-3' (SEQ ID NO:21)

5'-CGCAGATCTTTAAATTACGGCAGGACTTTA
GCGGAAA-3' (SEQ ID NO:22)

PCR amplification and the reaction product purification were conducted as described in Materials and Methods.

The DNA was resuspended and digested with BanI REN. The digested DNA was separated by low-melting agarose gel and ligated with pPT0285 (U.S. Pat. No. 5,496,712) which has been previously digested with BanI REN and purified by agarose gel electrophoresis followed by NACS column purification. The products of this ligation reaction were transformed into *E. coli* strain HB101. Plasmid DNA from transformants was purified and digested with BanII REN. Plasmid DNA from two clones that gave the correct digestion pattern was sequenced. One plasmid DNA, designated pPT0358, was found to be correct and chosen for further constructions.

Plasmid pPT0340 was digested with BanII REN, and the 156 bp fragment containing the SELP0K gene monomer was purified using agarose gel electrophoresis followed by an Ultrafree MC spinfilter and removal of salt on a Biospin column. The fragment was ligated with pPT0358 previously digested with BanII REN and the larger fragment was purified by agarose gel electrophoresis followed by purification on an Ultrafree MC spinfilter and a Biospin column. The products of the ligation mixture were transformed into *E. coli* strain HB101. Plasmid DNA from transformants was purified and analyzed by digestion using BanI REN. Plasmid pPT0360 containing a dimer of the SELP0K gene fragment was used for subsequent constructions.

Plasmid DNA pPT0360 was treated with BanI REN. The SELP0K dimer gene fragment was purified using agarose gel electrophoresis followed by an Ultrafree MC spinfilter and desalted on a Biospin column. The fragment was ligated with pPT0134 previously digested with FokI REN, passed through a Millipore Probind filter by microfuging for 3 min at 12,000 rpm, treated with SAP, passed through another Millipore Probind filter and desalted on a Biospin column. The products of the ligation mixture were transformed into *E. coli* strain HB101. Plasmid DNA from transformants was purified and analyzed by digestion using DraI REN. Plasmid pPT0363 containing the desired DNA fragment was used for subsequent constructions.

Plasmid DNA pPT0363 was treated with EcoNI REN. The digestion was passed through a Millipore Probind filter by microfuging for 3 min at 12,000 rpm, desalted on a Biospin and self-ligated. The products of the ligation mixture were transformed into *E. coli* strain HB101. Plasmid DNA from transformants was purified and analyzed by digestion using DraI REN. Plasmid pPT0365 containing the desired deletion was treated with BsrFI REN. The digestion was passed through a Millipore Probind filter by microfuging for 3 min at 12,000 rpm, desalted on a Biospin column and self-ligated. The products of the ligation mixture were transformed into *E. coli* strain HB101. Plasmid DNA from transformants was purified and analyzed by digestion using Asp700 and NgoMI RENs. Plasmid pPT0366 containing the desired SELP9K gene monomer (Table 5) was used for the polymer gene construction.

TABLE 5

Nucleotide and Amino Acid Sequence of SELP9K Gene Monomer

| | | | | | | | | | | | | | | | | |
|---|---|---|---|---|---|---|---|---|---|---|---|---|---|---|---|---|
| GGT | GCC | GGT | GCG | GGC | TCT | GGT | GTT | GGA | GTG | CCA | GGT | GTC | GGT | GTT | CCG | (SEQ ID NO:23) |
| G | A | G | A | G | S | G | V | G | V | P | G | V | G | V | P | (SEQ ID NO:24) |
| GGT | GTA | GGC | GTT | CCG | GGA | GTT | GGT | GTA | CCT | GGA | AAA | GGT | GTT | CCG | GGG | |
| G | V | G | V | P | G | V | G | V | P | G | K | G | V | P | G | |
| GTA | GGT | GTG | CCG | GGC | GTT | GGA | GTA | CCA | GGT | GTA | GGC | GTC | CCG | GGA | GCG | |
| V | G | V | P | G | V | G | V | P | G | V | G | V | P | G | A | |
| GGT | GCT | GGT | AGC | GGC | GCA | GGC | GCG | GGC | TCT | GGT | GCA | | | | | |
| G | A | G | S | G | A | G | A | G | S | G | A | | | | | |

(b) Polymer Gene Construction

Plasmid DNA from pPT0366 was digested with FokI REN and then passed through a Millipore Probind filter by microfuging for 3 min at 12,000 rpm. The digestion fragments were separated by agarose gel electrophoresis. The SELP9K gene fragment, 174 bp, was excised and purified by Ultrafree-MC 0.45 micron spin filter (Millipore) and followed by Bio-Spin 6 column (BioRad) equilibrated with DI water, in a Sorvall RC5B centrifuge using an HB4 rotor at 2,500 RPM for 4 min. The purified fragment was ligated with plasmid pPT0317 previously digested with BanI REN, then passed through a Millipore Probind filter and followed by a Bio-Spin 6 column. The DNA was then treated with SAP and passed through a Millipore Probind filter and a Bio-Spin 6 column.

The product of this ligation reaction was transformed into E. coli strain MM 294 (CGSC 6315) RecA. Transformants were selected for resistance to kanamycin. Plasmid DNA from individual transformants was purified and analyzed for increased size due to SELP9K multiple DNA insertion. Several clones were obtained. Four clones were used for expression analysis. pPT0377 was shown to contain a 2.08 kb polymer gene insert.

(c) Expression Analysis

E. coli strain MM 294 containing plasmid pPT0377 was grown as described in Materials and Methods. The proteins produced by these cells were analyzed by SDS-PAGE for immunoreactivity with anti-ELP antibodies. A strong reactive band was observed with an apparent molecular weight of 62 Kd.

Amino Acid Sequence of SELP9K pPT0377

Amino Acids: 749 MW: 60,066 daltons

MDPVVLQRRDWENPGVTQLNRLAAHPPFASDPM
[GAGAGS (GVGVP)$_4$GKGVP (GVGVP)$_3$ (GAGAGS)$_2$]$_{12}$
GAGAMDPGRYQDLRSHHHHHH (SEQ ID NO:25)

C. Example 2

Polymer Production

E. coli strain EC3 containing the respective plasmid encoding each polymer shown in Table 6 below was prepared in accordance with the methods described in U.S. Pat. No. 5,243,038. Each strain was then fermented using a fed-batch method. These polymer samples were used for the production of SELP polymer films, sponges and fibrous meshes as described below (see Examples 3, 4 and 5).

Biomass for each polymer was harvested from the fermentation broth by centrifugation in a Sorval RC3B using a H6000A rotor at 5,000 rpm for 30 min at 10° C. to yield a packed cell paste. 500 grams of cell paste was resuspended in 2 liters of 50 mM Tris buffer (pH =8.0). The cell slurry was homogenized using a Manton Gaulin cell disrupter at 7,000–8,000 psi with three complete passes of the liquid. The cell homogenate was passed through a chilled heat exchanger to maintain the temperature at 15° C. or less. Pancreatic DNAse was added to the homogenate to a final concentration of 1 µg/ml and stirred at room temperature for 2 hrs. The homogenate was centrifuged in a Sorval RC3B centrifuge using a H6000A rotor at 5,000 rpm for 1 hr at 10° C.

For SELP0, 3, 7 and 8 preparations, the supernatant was placed into 12–14,000 molecular weight cut-off dialysis bags and dialyzed against 2 changes of 100× volume of 20 mM sodium acetate buffer (pH=4.7) for 24 hrs. The contents of the bags were transferred to centrifuge bottles and centrifuged in a Sorval RC3B centrifuge using a H6000A rotor at 5,000 rpm for 1 hr at 10° C. The supernatant was removed to a large beaker and the pH adjusted to 8.0 by addition of 30% ammonium hydroxide. Saturated ammonium sulfate was then added to reach a final concentration of 20% for SELP0, 25% for SELP3 and 8 and 33% for SELP7. The solution was stirred at room temperature for 1 hr. The solution was centrifuged in a Sorval RC3B using a H6000A rotor at 5,000 rpm for 30 min at 10° C. The pellet was resuspended in 2 liters of deionized water, placed in dialysis bags and dialyzed against 3 changes of deionized water of 100× volume over 48 hrs. The contents of the bags were shell frozen and lyophilized to dryness.

For preparations of SELP4 and 5, the centrifuged homogenate supernatant was directly precipitated with ammonium sulfate at a concentration of 25%. The solution was then centrifuged in a Sorval RC3B using a H6000A rotor at 5,000 rpm for 1 hr at 10° C. The pellet was resuspended in 5 liters of 4M LiBr and stirred at 4° C. for 16 hrs. The solution was centrifuged in a Sorval RC3B centrifuge using a H6000A rotor at 5,000 rpm at 10° C. for 1 hr. The pH of the supernatant was adjusted to pH 3.7 by slow addition of 1M acetic acid at 4° C. The solution was centrifuged in a Sorval RC3B using a H6000A rotor at 5,000 rpm at 10° C. for 1 hr. The supernatant pH was adjusted to 8.0 by addition of ammonium hydroxide and then dialyzed against 3 changes of 100× volume deionized water over 48 hrs. The solution was removed from dialysis and centrifuged in a Sorval RC3B using a H6000A rotor at 5,000 rpm at 10° C.

for 1 hr. Saturated ammonium sulfate was added to the supernatant to reach 25% of saturation and stirred for 1 hr. The solution was centrifuged in a Sorval RC3B using a H6000A rotor at 5,000 rpm at 10° C. for 1 hr. The pellet was dissolved in 4.5M LiBr, placed in dialysis bags and dialyzed against 3 changes of 100× volume of deionized water. The contents of the bags were shell frozen and lyophilized to dryness.

All reagent solutions used in the following procedures were depyrogenated prior to use by filtration through a 10,000 nominal molecular weight cut-off hollow fiber cartridge (AG Technologies). All glassware and utensils used were sterilized and depyrogenated by heating at 180° C. for 4 hrs. 4–5 grams of all SELP dried polymers were dissolved in 1.2 liters of 10M urea. 20 mls of 2M Tris pH 8.0 and 780 mls of milli-Q water were added. The solution was sonicated to promote full dissolution of the protein. 500 grams of Whatman DE52 ion exchange resin was prepared by pre-cycling through acid and base treatment as recommended by manufacturer prior to and in between each usage. The resin was finally equilibrated with 6M urea, 20 mM Tris pH 8.0 in a beaker with gentle stirring. The resin was filtered in a buchner funnel until excessive liquid was removed. The cake of resin was placed in a beaker and the protein solution was added. The slurry was stirred gently for 1 hr. The slurry was filtered in a Buchner funnel and the liquid was collected in a cleaned vacuum flask. 500 grams of fresh precycled and equilibrated resin was added to a depyrogenated vacuum beaker and the filtered solution was added. The slurry was stirred gently for 1 hr and filtered again. The filtered solution was once more combined with 500 grams of freshly pre-cycled and equilibrated resin, stirred for 1 hr, and filtered. The final filtered solution was placed in 6,000 molecular weight cut-off dialysis bags which had been soaked in 0.5N NaOH for at least 24 hrs. The solution was dialyzed against 3 changes of 100× volume of deionized water. The dialyzed solution was removed from the bags, placed in depyrogenated lyophilization flasks and lyophilized to dryness. Employing the above procedure, the following polymers were prepared.

TABLE 6

Protein Polymers

| Polymer (MW) | Polymer Block Sequence[1] | Domain Abbr.[2] | E/S[3] | % S[4] |
|---|---|---|---|---|
| SELP0 (80,502) | [(VPGVG)$_8$(GAGAGS)$_2$]$_{18}$ SEQ ID NO: 26 | E8S2 | 4.0 | 21.9 |
| SELP8 (69,934) | [(VPGVG)$_8$(GAGAGS)$_4$]$_{13}$ SEQ ID NO: 27 | E8S4 | 2.0 | 35.3 |
| SELP7 (80,338) | [(VPGVG)$_8$(GAGAGS)$_6$]$_{13}$ SEQ ID NO: 28 | E8S6 | 1.33 | 45.0 |
| SELP3 (84,267) | [(VPGVG)$_8$(GAGAGS)$_8$]$_{12}$ SEQ ID NO: 29 | E8S8 | 1.0 | 51.9 |
| SELP4 (79,574) | [(VPGVG)$_{12}$(GAGAGS)$_8$]$_9$ SEQ ID NO: 30 | E12S8 | 1.5 | 42.2 |
| SELP5 (84,557) | [(VPGVG)$_{16}$(GAGAGS)$_8$]$_8$ SEQ ID NO: 31 | E16S8 | 2.0 | 35.7 |

[1]The first and last block domain of each polymer is split within the silk blocks such that both parts sum to a whole domain. All polymers also contain an additional head and tail sequence which constitutes approximately 6% of the total amino acids.
[2]Designates the number of consecutive blocks per repeating domain (E = elastin-like block, S = silk-like block)
[3]Ratio of blocks per polymer.
[4]% of total amino acids in polymer contributed by silk-like blocks.

Other polymers which were prepared include:

[(VPGVG)$_{32}$ (GAGAGS)$_8$]$_5$ (SEQ ID SEQ:32), referred to as SELP6; and

{(GAGAGS)$_{12}$ GAAVTGRGDSPASAAGY (GAGAGS)$_5$ (GVGVGP)$_8$]$_7$(SEQ ID No:33), referred to as SELPF.

Additional polymer samples including:

[(GAGAGS)$_2$ (GVGVP)$_4$ GKGVP (GVGVP)$_3$]$_6$ (SEQ ID NO:34), referred to as SELP0K;

[(GVGVP)$_4$ GKGVP (GVGVP)$_3$ (GAGAGS)$_4$]$_{12}$ (SEQ ID NO:35), referred to as SELP8K; and

[GAGAGS (GVGVP)$_4$ GKGVP (GVGVP)$_3$ (GAGAGS)$_2$]$_{12}$ (SEQ ID NO:36), referred to as SELP9K, were prepared according to the following methods. These polymer samples were used for the production of SELP gels as described below in Examples 6, 7, 8, 9 and 10. These protein polymer samples were produced from fermented biomass conducted under a glucose fedbatch fermentation process with minimal salts medium as described in Materials and Methods. SELP8, SELP8K, SELP9K and SELP5 polymers were produced using *E. coli* strains pPT0303, pPT0345, pPT0377 and pPT0263, respectively. SELP8, SELP8K and SELP5 were fermented using an NBS Fermacell, model F-130 fermentor (New Brunswick Scientific, Inc.) and SELP9K was fermented using an MBR LAB 15L GLAS STAHL NR264 fermentor (MBR Bioreactor AG). The biomass obtained from each fermentation run was separated from the medium by centrifugation, labeled, and stored frozen at −20° C. prior to purification.

SELP8 Batch 96083

The SELP8 batch 96083 was produced by combining two SELP8 preparations, 96071 and 96073, during the final steps of purification. Each preparation started with 1500 grams of frozen biomass that was resuspended in 10 liters of 20 mM Tris pH 8.0 with 10 mM EDTA. The suspension was mixed with a polytron mixer (Janke & Kunkel, Kika-werk, Ultra Turrex model T45-S4) until homogeneous. The suspension was passed three times through a Gaulin Model 15 M homogenizer at 8000 psi and the temperature was maintained below 15° C. throughout the lysis by means of a heat exchanger. After the first pass, 200 mls of 0.2 M phenylmethylsulfonyl fluoride (PMSF) in isopropanol was added. The lysate was centrifuged for 30 min at 8000 rpm at 4° C. in a Sorvall RC5B. The supernatant (8.3 liters) was decanted and then placed in Spectrapore dialysis bags (MWCO= 12–14 kdco) and dialyzed for 3 days at 4° C. against three changes of 100 liters of 20 mM sodium acetate, pH 4.7. The dialysate was centrifuged in a DuPont/Sorvall RC5B centrifuge for 1 hr at 8000 rpm at 10° C. 1300 mls of saturated ammonium sulfate was added dropwise to the supernant (5.2 liters) at room temperature while stirring. This mixture was allowed to stir for 1 hr, then it was centrifuged for 30 min at 8000 rpm at 10° C. in the RC5B. The pellet was redissolved in 500 mls of milli-Q water and dialyzed in Spectrapore dialysis bags (MWCO=12–14 kdco) against three changes of 100 liters of Milli-Q water over three days.

This polymer solution was then applied to a Poros HQ50 (Perspective) anion exchange column prepared as follows. Each step using the column, including the application and elution of the polymer solution, was done at 40 psi. An Amicon VA-180 column containing 4.0 liters of Poros HQ50 resin was depyrogenated by flushing 15 liters of 1.0 M NaOH/1.0 M NaCl through the column and downstream apparatus. The column was left in contact with this solution overnight. Tris buffer and DI water, used to equilibrate the column, were filtered through an AG/T hollow fiber ultra-filtration module (10,000 MWCO) which had previously been soaked in 0.5 N NaOH overnight and thoroughly flushed with DI water. Glass sample collection vessels were baked in a dry heat oven at 180° C. for a minimum of 4 hrs. After depyrogenation, the column was then flushed with 15 liters of ultrafiltered DI water, followed by 15 liters of ultrafiltered 200 mM Tris-HCl, pH 8.0, followed by 10 liters of ultrafiltered 20 mM Tris-HCl, pH 8.0.

The polymer solution was diluted to 4 liters and to a final concentration of 20 mM Tris-HCL, pH 8.0, using ultrafiltered 200 mM Tris-HCl, pH 8.0. The sample was then allowed to flow through the column. The eluate was monitored for absorbance at 280 using an Isco UA-5 absorbance detector with a 280–310 nm filter. After the sample was applied, the column was flushed with ultrafiltered 20 mM Tris-HCl, pH 8.0. The fractions containing protein were collected and dialyzed in Spectrapore dialysis bags (6–8 kdco) which had previously been soaked overnight in 0.5 N NaOH and then rinsed thoroughly with ultrafiltered DI water. The product was dialyzed against three changes of 100 liters of DI water. The final dialysate obtained was lyophilized in thermally depyrogenated lyophilization flasks.

The yields of both batches were combined and repassed over the Poros HQ50 column as described above. The final dialyzed product was lyophilized and stored in a thermally depyrogenated container at −20° C.

SELP9K batch 96084

1572 grams of frozen biomass was resuspended in 6 liters of DI water. When completely thawed the suspension was mixed with a polytron mixer (Janke & Kunkel, Kika-werk, Ultra Turrex model T45-S4) and the cells were lysed using a Gaulin Model 15M homogenizer (three passes at 8000 psig). The temperature of the homogenate was maintained below 8° C. by means of a heat exchanger. The resultant cell lysate was mixed with an equal volume of polyethyleneimine (PEI) solution (0.04% w/v, pH 8.0, Amresco High Purity Grade, MW 50,000) and mixed for 15 min. The PEI mixture was centrifuged in a DuPont/Sorvall RC3B centrifuge for 30 min at 5000 rpm, 8° C. The supernatant was filtered through Whatman #4 filter paper in a Buchner funnel and saturated ammonium sulfate solution was slowly added to a final concentration of 25% of saturation. The precipitated fraction was allowed to settle to the bottom of the container while stored at 4° C. overnight. The supernatant was carefully decanted and the precipitate was resolubilized in 2.0 liters of DI water and dialyzed in Spectrapore dialysis bags (MWCO=12–14 kdco) against two changes of 200 liters of cold DI water. The resultant dialysate was centrifuged in a DuPont/Sorvall RC5B centrifuge, GS2 rotor, at 8000 rpm, 8° C. for 60 min. The recovered supernatant was filtered through a Whatman #4 filter paper in a Buchner funnel. The filtrate was diluted to a total protein concentration (as determined by Lowry protein assay) of 1.0 mg/ml and saturated ammonium sulfate solution was added to a final concentration of 20% of saturation. The precipitate was collected after settling as described above and resolubilized in 1.0 liter of cold DI water. The polymer solution was passed through a Gelman Spiralcap 0.2 μm filter cartridge. The solution was diafiltered against Milli-Q water using a Millipore Pellicon filtration apparatus containing a 0.5 square meter BIOMAX filter cassette (30K MWCO) until a conductivity of <20 μS/cm was obtained. The final volume was 2 liters.

The sample was brought up to 4 liters with 400 mls of 200 mM Tris pH 8.0 and 1.6 liters of milli-Q water. This was passed through a Poros HQ50 anion exchange column as described above. The flow through and column wash fractions were dialyzed in Spectrapore dialysis bags (6–8 kdco) which had previously been soaked overnight in 0.5 N NaOH and then rinsed thoroughly with ultrafiltered DI water. The product was dialyzed against three changes of 180 liters of DI water. The final dialysate obtained was lyophilized in baked lyophilization flasks and stored in thermally depyrogenated containers at −20° C.

SELP8K batch 96072

Three kilograms of frozen biomass were resuspended to 12 liters with DI water. When completely thawed and well mixed, cell lysis was accomplished by passing it through a Gaulin Model 15M homogenizer (three passes at 8000 psig). The solution temperature was maintained below 8° C. by means of a heat exchanger. The resultant cell lysate was mixed with an equal volume of polyethyleneimine (PEI) solution (0.04% w/v, pH 5.0)(Amresco High Purity Grade, MW 50,000) and mixed for 15 min. The PEI mixture was centrifuged in a RC3B centrifuge for 30 min at 5000 rpm, 8° C. The supernatant was collected and saturated ammonium sulfate solution was slowly added to a final concentration of 20% of saturation. The precipitated fraction was allowed to settle to the bottom of the container while stored at 4° C. overnight. The supernatant was carefully drawn off and the ammonium sulfate precipitate was resolubilized in 4.0 liters of DI water. The polymer solution was dialyzed in Spectrapor dialysis bags (MWCO=12–14 kdco) against two changes of 200 liters of cold DI water. The resultant dialysate was centrifuged in a RC5B centrifuge, GS2 rotor, at 8000 rpm, 8° C. for 60 min. The recovered supernatant was diluted to a total protein concentration (as determined by Lowry protein assay) of 1.0 mg/ml and saturated ammonium sulfate solution was again added to 20% of saturation. The second ammonium sulfate precipitate was collected as described above and resolubilized in 5.0 liters cold DI water. The polymer solution was passed through a Gelman Spiralcap 0.2 μm filter cartridge and then diafiltered against Milli-Q water using a Millipore Pellicon cassette containing a 0.5 square meter BIOMAX filter cassette (30K MWCO) until a conductivity of <20 μS/cm was obtained.

Six liters of sample at 5.7 mg/ml protein concentration was passed through a Poros HQ50 anion exchange column as described above. The collected product fractions were dialyzed against four changes of 200 liters of DI water. The final dialysate obtained was lyophilized in baked lyophilization flasks, and stored in thermally depyrogenated containers at −20° C.

Using similar methods, the polymer SELP0K was prepared.

SELP5 5VA-1

Twelve kilograms of frozen biomass was thawed and resuspended in 60 liters of 50 mM Tris-HCl, pH 8.0. The cell slurry was lysed as described above with the additional step of adding PMSF (as a 0.2 M solution in isopropanol) to a final concentration of 2.5 mM after the first pass through the Gaulin homogenizer. The cell lysate was centrifuged in a RC3B centrifuge for 60 min at 5000 rpm, 8° C. Saturated ammonium sulfate solution was slowly added to the resultant cell lysate supernatant to 25% of saturation. This was mixed for 60 min and centrifuged in the RC3B for 30 min at 5000 rpm, 8° C.

The precipitate was resuspended in 40 liters of 4.0 M lithium bromide and stirred overnight at 4° C. The solution was centrifuged in a Sharples AS14 centrifuge at a flowrate of 120 ml/min at approximately 14,000×g. The recovered supernatant was adjusted to a pH of 3.7 by slow addition of concentrated glacial acetic acid and stirred overnight at 4° C. to produce a precipitate. The precipitate was removed by centrifuging in the Sharples AS14 as described above. The supernatant (35 liters) was adjusted to pH 8.0 with concentrated ammonium hydroxide and diafiltered using a Millipore Pellicon filtration apparatus containing a 30K MWCO filter cassette (0.5 square meter) to a final conductivity less than 100 μS/cm. The retentate was centrifuged in the Sharples AS14 centrifuge at 100 ml/min flow rate. Saturated ammonium sulfate solution was added to the recovered supernatant to 25% of saturation and stirred for 60 min. The solution was centrifuged in the RC3B centrifuge for 30 min at 5000 rpm, 8° C. The precipitate was resolubilized in 4.0 liters of 4.5 M lithium bromide solution, diluted to 200 liters with DI water, and again diafiltered with the 30,000 MWCO ultrafilter as described above. When a conductivity less than 350 μS/cm was obtained, the solution was concentrated with the ultrafilter to a volume of 10 liters and lyophilized.

The material was dissolved in 10 liters of 6.0 M urea/20 mM Tris-HCl, pH 8.0 in preparation for application to the Poros HQ anion exchange column as described above. The column and downstream apparatus was depyrogenated and equilibrated as described above except that the final equilibration of the column was performed with 10 liters of ultrafiltered 6.0 M urea/20 mM Tris-HCl, pH 8.0. The sample was applied to the column and collected in sterile pyrogen-free plastic bottles (1000 ml). The column was flushed with additional depyrogenated 6.0 M urea/20 mM Tris-HCl, pH 8.0. Fractions containing protein were dialyzed in Spectrapor dialysis bags (6–8 kdco) against four changes of 200 liters of DI water. The final dialysate was lyophilized in dry-heat depyrogenated lyophilization flasks, collected in thermally depyrogenated containers and stored at −20° C.

Sample Characterization

The polymer samples prepared as described above were characterized using standard analytical methods. The samples were evaluated for moisture content, amino acid composition and elemental composition (carbon, hydrogen, and nitrogen). Using the theoretical values for amino acid and elemental composition as expected from a 100% pure product, it is possible to estimate the purity of the samples based on the actual composition of the samples compared to theoretical.

Lyophilized SELP samples contain various amounts of water depending on the lyophilization conditions and their subsequent exposure history to ambient atmospheres. Therefore, it is important to determine the moisture content of SELP samples both at the time of production and again when critical experiments and measurements are made. Moisture content is determined by measuring the weight loss after drying to constant weight at 110° C.

Elemental composition can be used to determine the weight percent carbon and nitrogen contained in a sample. Because proteins are more abundant in nitrogen than almost all other macromolecules (C/N ratio of SELP8K is 3.25), and making the assumption that any contaminants contained in the sample will contribute to the carbon content to a greater degree than the nitrogen content, we may use the excess carbon with respect to nitrogen in the sample as a maximum estimate of chemical purity. It should be noted, however, as is the case for the SELP5 sample below, C/N values less than theoretical denote excess nitrogen in the sample which might be due to residual processing chemicals such as urea, ammonium sulfate or Tris buffer each of which have high nitrogen contents.

Amino acid composition analysis (AA Comp) determines the amount of each amino acid contained in the sample. AA Comp does not evaluate any other chemical species in the sample besides protein. Because the SELP polymers consist of only a limited number of amino acids (G, A, S, V, P, and K are the main ones) and completely lack one amino acid (isoleucine, I), AA Comp data can be used to estimate the protein purity of the sample (ie. the fraction of protein in the sample which is SELP). E. coli proteins that might contaminate SELP samples were determined by amino acid composition analysis to contain 4.8 weight % isoleucine. The amount of isoleucine detected in SELP samples, as derived from E. coli proteins, divided by 0.048 represents the amount of protein in the sample contributed by such contaminants. The detection limit of our analysis for any single amino acid is 0.1%. Therefore, the limit of contaminant protein detection based on isoleucine will be 0.001/0.048= 0.021 or 2.1%.

Because SELPs consist almost exclusively of the six amino acids listed above, the fraction of the total amino acids constituted by these amino acids as compared to the theoretical content of a 100% pure sample of the product is also an estimate of purity. This estimate is only good for relatively pure samples where contaminating proteins contribute only small amounts of the amino acids used in the analysis. E. coli proteins contain 22.9% by weight G+A+S+P+V and 31.1% by weight G+A+S+P+V+K. If a SELP sample is 98% pure, for example, the E. coli protein contaminants would contribute 0.02×0.311=0.006 or 0.6% of the total G+A+S+P+V+K in the sample (+0.6% error). At 95% purity, the error of this estimate may be +1.6%. For SELP8 and SELP5, which contain very little lysine, K is not included in the analysis. Therefore, the potential errors at 95% and 98% purity for these two polymers are 1.15% and 0.5%, respectively. Table 7 lists the results of these analyses from several SELP sample preparations.

TABLE 7

Characterization of SELP Samples

|  | | Elemental Analysis | | Amino Acid Composition | |
| --- | --- | --- | --- | --- | --- |
|  | Moisture | C/N | Purity | Protein Purity based on: | |
| Polymer Batch | Analysis Weight (%) | ratio (Theor. C/N) | based on Excess C (%) | Isoleucine Content (%) | % G + A + S + V + P (+ K)* (%) |
| SELP8K 96072 | 16.1 | 3.28 (3.25) | 99.1 ± 0.1 | None Detected >97.9 | 100.8 |
| SELP8 96083 | 12.1 | 3.46 (3.32) | 95.7 ± 0.2 | None Detected >97.9 | 100.7 |
| SELP9K 96084 | 18.0 | 3.36 (3.32) | 98.8 ± 0.7 | None Detected >97.9 | 100.9 |
| SELP5 5VA1 | 5.6 | 3.25 (3.32) | NA** | 95.8 | 98.3 |

*lysine was not used in the calculation of protein purity of SELP8
**purity estimate was not possible because this sample contains excess nitrogen (see discussion above)

D. Example 3

SELP Films

SELP films that were approximately 0.05 mm thickness were produced by solvent evaporation.

Approximately 1.7 grams of each polymer, except for SELP7 where only 1.05 grams was used, were solubilized in 34 mls of 88% formic acid. The solution was stirred for 7 hrs at room temperature to insure complete solubilization. The solution was then poured into a film casting apparatus consisting essentially of a rectangular polyethylene trough with a removable polyethylene bottom. The casting apparatus was placed in a vacuum oven attached to a nitrogen gas source for sparging the atmosphere. The films were dried in the sealed oven drawing a 10–15 micron vacuum with a slow continual influx of nitrogen gas at 60–75° C. After 15–18 hrs of drying, the apparatus was disassembled and the film was peeled off the polyethylene bottom. The films were exposed for 5 min to a basic atmosphere (5% open solution of ammonium hydroxide in a sealed desiccator) to neutralize any residual formic acid.

A polyethylene sheet of the same area dimensions as the protein film was roughened by hand using fine grit sand paper and a thin film of cyanoacrylate glue was spread over its surface. The protein film was applied to the wet surface. A teflon sheet was placed on top and bottom of the polyethylene and protein layers and stainless steel plates were placed around those. The entire assembly was pressed in a Carver laboratory press at a force of 0.8 metric tons for 18 hrs at room temperature. The polyethylene/protein film laminated sheet was placed on a cutting board and 1.3 cm diameter discs were punched out using a stainless steel punch and rubber mallet. The discs were placed individually in stoppered glass vials.

Specimens were produced from each of the polymers as well as denatured collagen protein (DCP) produced identically as described for the SELP films. Bovine collagen (fibrillar form, lot number 921101) was obtained from Colla-Tec, Inc. (Plainsboro, N.J.). It was completely solubilized in 88% formic acid producing a clear but viscous solution. All specimens were sterilized by electron beam irradiation at 2.5+/− 0.2 Mrads. Each disk was implanted subcutaneously in the back of rats such that the protein film was in direct contact with the muscle tissue. The specimens remained in the animals for different periods of time: one, four and seven weeks post implantation. At each time interval six specimens per polymer group were retrieved for protein analysis. Additional specimens from each group were evaluated for tissue reaction by histology.

Non-implanted and retrieved specimens were analyzed to determine the mass of SELP film contained per specimen. Amino acid analysis was performed on each specimen by sealing them individually in an hydrolysis vial with constant boiling hydrochloric acid and heating for 24 hr at 100–110° C. After hydrolysis, the specimen was extracted and an aliquot of the extract was derivatized with PTC. The derivatized amino acids were separated by reverse phase HPLC and quantified by their absorbance at 254 nm according to the methods of Henrickson and Meredith, *Anal. Biochem.* 137:65–74 (1984).

The mass of the SELP film present on each specimen was determined. The amino acid contribution of the SELP protein was estimated based on the total content of the amino acids G, A, S, V and P which for the pure polymers is >95%. Other amino acids potentially contributed by extraneous protein deposited onto the specimens during residence in the body were excluded from these analyses. Average SELP film mass for non-implanted specimens was determined from the same batch of specimens used for implantation. Average SELP film mass for retrieved specimens was similarly calculated except that replicates having values greater than two standard deviations from the mean were discarded. Deviations in many cases were due to partial retrieval of specimens that had fragmented in the tissue after implantation and may not reflect true resorption.

Resorption Analysis and Results

Resorption analysis was conducted statistically by analyzing four specimen population treatment groups. These were: (1) non-implanted; (2) one week post-implantation; (3) four weeks post-implantation; and (4) seven weeks post-implantation.

TABLE 8

Polymer Film Mass Remaining as Determined by AA Composition Analysis (in mg)

| | SELP0 | | SELP3 | | SELP4 | | SELP5 | | SELP7 | | SELP8 | | DCP | |
|---|---|---|---|---|---|---|---|---|---|---|---|---|---|---|
| Initial Film Mass | 12.21 | +/−1.41 | 5.99 | +/−0.46 | 8.19 | +/−0.86 | 8.51 | +/−1.04 | 3.27 | +/−0.34 | 8.43 | +/−0.59 | 6.6 | +/−1.04 |
| 1 Week Film Mass | 0.53 | +/−0.31 | 5.93 | +/−0.73 | 7.89 | +/−0.55 | 7.72 | +/−1.57 | 4.67 | +/−1.33 | 11.13 | +/−1.40 | 0.15 | +/−0.07 |
| 4 Week Film Mass | 0.27 | +/−0.13 | 6.24 | +/−0.61 | 9.20 | +/−1.08 | 7.49 | +/−0.75 | 0.19 | +/−0.16 | 8.26 | +/−1.21 | 0.09 | +/−0.03 |
| 7 Week Film Mass | 0.10 | +/−0.02 | 3.49 | +/−1.60 | 8.56 | +/−0.67 | 8.77 | +/−0.97 | 0.08 | +/−0.03 | 1.52 | +/−1.40 | 0.07 | +/−0.03 |

TABLE 9

Polymer Film Remaining as Percent of Non-implanted Mass

| | SELP0 | SELP3 | SELP4 | SELP5 | SELP7 | SELP8 | DCP |
|---|---|---|---|---|---|---|---|
| Initial Film Mass | 100.0% | 100.0% | 100.0% | 100.0% | 100.0% | 100.0% | 100.0% |
| 1 Week Film Mass | 4.3% | 98.9% | 96.3% | 90.7% | 142.8% | 132.0% | 2.3% |
| 4 Week Film Mass | 2.2% | 104.1% | 112.4% | 88.0% | 5.8% | 98.0% | 1.3% |
| 7 Week Film Mass | 0.8% | 58.2% | 104.5% | 103.1% | 2.6% | 18.1% | 1.1% |

The results from Table 8 are the values for the mass of protein film contained on specimens after implantation. Each value is the mean of at least five specimen masses as determined by amino acid composition. Table 9 displays the same values as a percent of the initial weight prior to implantation as determined by the mean mass of six specimens of the non-implanted specimens. The results indicate that upon implantation, SELP0 and DCP are substantially resorbed by one week, falling below 5% of their non-implanted masses. SELP7 is substantially resorbed by four weeks with only 5.8% remaining. SELP8 and SELP3 are resorbing by seven weeks with mean values of 18.1% and 58.2% remaining, respectively. SELP4 and SELP5 films show no evidence of resorption at seven weeks.

From the above results one may conclude the following. Faster resorption correlates with compositions containing domains of silk-like blocks fewer than eight. The polymers containing eight silk-like blocks have substantially reduced rates of resorption. However, the total content of silk-like blocks in the copolymer composition does not correlate with resorption rate. While very similar compositionally, SELP7 and SELP8 resorbed quickly, while SELP4 and SELP5 do not resorb in seven weeks. The lack of resorption of SELP4 and SELP5 films at seven weeks post-implantation corresponds with repeating domains containing greater than eight elastin-like blocks. Although their silk-like block lengths are identical at eight, SELP4 and 5 with elastin-like block lengths of 12 and 16 resorb to a lesser degree than SELP3, which has an elastin-like block length of 8.

The subject polymers, regardless of their composition, form free-standing films with strength enough to allow easy handling. SELP7 and SELP4 films have tensile strengths of 19+/−1 and 21+/−8 MPa, respectively. The compositional difference between them that causes SELP7 to resorb in four weeks and SELP4 to remain intact beyond seven weeks makes little apparent difference in their tensile properties. These strengths are adequate for their use in surgical and wound healing applications.

The observed resorption of these polymers occurs via surface erosion. This is consistent with the mechanism of degradation of SELP proteins within the body. At physiological conditions, proteins will degrade only through the action of proteases. Because endogenous proteases are high molecular weight compounds of approximately 20 kDa or greater, their diffusion into the dense SELP films will be limited. The degradation of SELP films is, therefore, progressive from the external surfaces of the material. The subject materials therefore should undergo a slow loss of mechanical integrity while being reduced in mass.

E. Example 4

SELP Porous Sponges

The function of an implanted material depends greatly on its form, morphology and mechanical strength. SELP polymers have been fashioned into a variety of forms; dense films, porous sponges, and fibrillar mats. Dense films or sheets, as described above, are semi-permeable barriers which may have utility in surgical repairs by restricting fluid or gas flow, blocking cellular migration, maintaining tissue separations, and confining and protecting implanted organs or devices. Their properties will vary depending on their permeability and their thickness which may range from 0.05 mm to greater than 1 mm. For example varying their thickness will effect their mechanical strength, their resistance to abrasion, and their ultimate resorption.

SELP polymers have been produced as follows as three dimensional, porous sponges to serve as implantable materials that will support cell and tissue ingrowth.

All glassware to come in contact with the protein polymer was depyrogenated by heating to 180° C. for 6 hrs. SELP5 (0.978 g) was stirred in LAL reagent grade water until dissolved to yield a 1.0% w/v aqueous solution. This solution was aseptically transferred to a 100 ml ST 24/40 pear shaped flask and tared. This flask was fitted with a spray trap, attached to a rotary evaporator, and 65.2 g of water was evaporated using a bath temperature of 39° C., a system pressure of 42 mbar, and a rotation rate of 125 rpm, to yield a solution of 3.0% w/v concentration. This solution was poured 6 mm deep into six standard sterilized Petri dishes (mm diameter); covered with standard lids; placed on a small plastic tray; and placed in a −8° C. freezer overnight. After freezing, the lids were removed from the Petri dishes; the Petri dishes were placed into a 1200 ml wide mouth lyophilization flask and lyophilized to dryness. After completion of lyophilization, the sponges were removed from their Petri dishes and placed, individually, into a 100 ml wide mouth flask containing 75 ml of methanol at room temperature. The head space was evacuated to less than the vapor pressure of the methanol to induce eubulation and insure compete displacement of air entrained within the sponge by the methanol. The sponge, wetted with methanol was allowed to stand for 5 min at room temperature at room temperature. methanol was removed from the sponge by washing 6 times with LAL reagent grade water (175 ml per wash) and allowing each to stand for 5 min. The sponges, wetted by water, were returned to 35 mm diameter Petri dishes, frozen at −8° C., and again lyophilized. The lyophilized sponges were placed into new 35 mm diameter Petri dishes, lids applied and sealed with parafilm®, placed into a plastic instrument bag, heat sealed, and sterilized using an electron beam irradiation at 2.8 Mrads.

The sponges were dimensionally stable when immersed in saline or water. When engorged with saline, the sponge turned from white to grey and was somewhat translucent. The engorged sponge retained its original dimensions. Minimal swelling was observed. The geometry and edges of the wet sponge remained unchanged. The observed aqueous stability of the SELP5 sponges is different from the properties of collagen hemostatic sponges (Helistat, Marion Laboratories, Kansas City, Mo.) which almost immediately collapse when exposed to liquid.

SELP5 sponges were cut into 2×2×0.4 cm specimens and applied to 2×2 cm full thickness dermal wounds in pigs. 2×2×0.3 cm specimens of Helistat were similarly applied to wounds. After bleeding was controlled and the wound flushed with saline, the specimens were laid into the tissue void such that they would firmly contact the wound bed. The Helistat specimens became completely or partially engorged within a few seconds to several min after application depending on the amount of the blood in the wound. The engorged Helistat specimens collapsed and shrunk resulting in nonuniform coverage of the wound, in some cases, exposing part of the wound beds.

The SELP5 sponges remained substantially white during the 5 min observation period after application indicating that they did not immediately absorb blood. One corner of one specimen turned red within a minute after application. It remained physically unchanged. The SELP5 sponges adhered well to the wound bed and could not be lifted out of the wound with forceps using mild tension. The SELP5 sponges did not shrink upon contact with the bloody tissue and continued to completely cover the wound during observation.

All wounds were covered with petrolatum gauze pads and bandaged. After 7 days, the wounds were undressed and observed to determine the extent of healing. Wounds containing SELP5 sponges had progressed normally through the healing process as compared to wounds to which no material was applied. The sponge material had not been extruded from the wound as there was no evidence of extraneous material on the gauze pads. No evidence of excessive inflammation was observed. Epithelialization of the wound was in progress.

F. Example 5

SELP Fibrous Meshes

SELP polymers can be fabricated as non-woven fibrous meshes to produce fibrillar mats which are flexible, have good drapability, and are stable in wet environments. Fibrous meshes with similar physical properties were produced from SELP5, SELP7 and SELPF using the following procedure. 1 gram of polymer was dissolved in 88% formic acid with stirring at room temperature until homogenous. For SELP5, 5 mls of formic acid were used to dissolve the lyophilized polymer. For SELP7 and SELPF, 4 and 3 mls of formic acid were used, respectively.

The polymer dope was drawn into a 1 cc polypropylene syringe, affixed with a 75 mm×20 gauge stainless steel hypodermic needle, and mounted on a Sage Instruments syringe pump (model 341B). The pump was set to deliver approximately 0.05 to 0.07 cc/min. The tip of the needle was placed at 90° C. to a gas stream delivered from a stainless steel needle (25 mm×20 gauge). A more acute angle was also used. The dope delivery needle and the gas delivery needle were mounted onto a steel "L"-bracket using miniature "C"-clamps and pads of neoprene rubber such that a gap of 1 mm separated their tips. The tips were displaced in the vertical direction by 0.5 mm such that the gas stream passed slightly over the flanged end of the hypodermic needle. The gas stream was supplied either with compressed air or high purity (extra dry) nitrogen gas. Compressed air was supplied by an oiless compressor using a diaphragm pump. The air in the reservoir was a ca. 8 atm pressure and was regulated down to ca. 2–6 atm before being fed to the spray apparatus. When nitrogen was used, it was delivered at 20 psi. The relative humidity was less than 47%.

Fine filaments were formed on and around the edges of a rectangular, 1/16 inch polypropylene mesh that was used as a target approximately 7–12 inches from needle tips. Filaments streamed off the edges of the target and when they were approximately 5 cm in length, they were collected on a circular, metal wire loop of 38 mm in diameter. Filaments were collected across the loop forming a web of suspended filaments in the center. The web was removed from the loop by compressing the web between two 35 mm polystyrene discs and pressing the web through the wire frame. Fibrous meshes were built up by compressing 5–8 webs between the same discs.

The meshes were stabilized by flooding them with 1 ml of either 100% methanol or 100% ethanol and allowing them to dry under ambient conditions. The meshes were sterilized by electron beam irradiation at a dose of 2.5 MRads. Under microscopic observation, the meshes consisted of fine filaments which varied in diameter from 0.1 to 10 $\mu$m. The meshes were stable when placed in saline for more than 24 hrs.

The meshes were applied to 2×2 cm partial and full thickness dermal wounds in pigs in order to investigate their biocompatibility and their ability to incorporate within the healing tissue. The meshes were removed from the polystyrene discs with forceps and applied to the wound bed. The edges of the meshes could be pulled across the tissue allowing the mesh to be spread and/or rearranged over the wound. The wounds were covered and examined every two days for signs of bioincompatibility. No adverse effects were observed in wounds containing SELP fibrous meshes. After 14 days, the wounds were completely epithelialized. Histological examination of tissues from wounds to which SELPF fibrous webs had been applied showed that foreign material in the form of filaments had been incorporated into the healing tissue.

These data indicate that SELP fibrous meshes are well tolerated in healing tissue. Their presence does not interfere with normal healing. In one case, SELP filaments were clearly shown to reside within the healed tissue.

SELP films, meshes, and sponges can serve as resorbable packing materials that can be used to augment the loss of soft tissue that occurs during traumatic injury or surgical dissection. Their application at the time of injury can encourage infiltration, overgrowth, and eventual replacement of the materials with healthy tissue. The mass of the implanted material can provide enough stability to maintain the geometric contours of the body site at which the tissue was lost. Their presence can also mechanically reinforce the wound site such that delicate, healing tissues can form while protected from further physical injury.

G. Example 6

SELP Gel Characterization

The gelling behavior of three SELP polymers were investigated using a Brookfield cone and plate viscometer. The studies demonstrated that gelation was a function of time, temperature, polymer composition, and that certain additives inhibited or accelerated the onset or rate of gelation.

SELP0K batch 96042, SELP8K batch 96072 and SELP5 batch 5VA1 were dissolved in phosphate buffered saline solution (1×PBS, Irvine Scientific) at 20% (w/w). At the time of these studies, each of the polymer samples had the following moisture contents: 5VA-1, 5.55% moisture; 96072, 6.84% moisture; and 96042, 11.03% moisture. The polymer solutions were mixed by hand until dissolved (3–4 min) and centrifuged for 2–3 min at high speed in a clinical centrifuge (International Equipment Co.) in order to clear air bubbles from the solution. The polymer solution was transferred to the cup of a Brookfield Syncro-Lectric rotational viscometer (Model RVTCP, CP-52 cone and cup configuration, Brookfield Engineering Laboratories) using a 1.0 cc polypropylene syringe (Becton Dickinson). Generally, the elapsed time from which the 1×PBS was added to the protein to the time in which the viscometer was started, was about 6 to 10 min.

The CP-52 cone, which had a cone angle of 3.0°, permitted the use of a 0.5 mL sample and the measurement of viscosities up to 196.6 Pa·sec. The cup, which allowed the circulation of liquid to control sample temperature, was connected to either a Cannon constant temperature bath (Cannon Instrument Company, Model M-1) or a VWR thermostated bath (VWR Scientific, Model 1150). Generally, the VWR thermostated bath was used for ambient and sub-ambient temperatures. For supra-ambient temperatures, either one of the temperature control systems was used interchangeably. Both temperature control systems were capable of controlling temperature to within ±0.1° C. Temperature was monitored using a type J thermocouple (OMEGA Engineering, catalog number SA1-J) surface-mounted on the exterior of the cup. The temperatures used in this study were 4, 23, and 37° C.

Prior to use, the temperature of the cone and cup on the Brookfield viscometer was allowed to equilibrate, and then the gap between the cone and cup was set according to the manufacturers instructions. The viscometer was started and allowed to rotate continuously at 20 rpm. The initial viscosity and subsequent viscosities were measured. The experiments were generally allowed to continue until the viscometer approached its maximum capability.

The gelation of SELP8K batch 96072 was also studied in solutions containing additives that affect gelation. 20% (w/w) SELP8K batch 96072 was studied in 1×PBS containing 6 molar urea (UltraPURE™ Urea, Life Technologies). Urea is known to inhibit the crystallization of proteins by disrupting hydrogen bonding. The gelation of SELP8K batch 96072 solution to which pregelled SELP8K powder was added was also studied. Previously gelled SELP8K batch 96072 solution was frozen at −20° C. and lyophilized. The lyophilized SELP8K protein was comminuted to a powder by milling in methanol against 240 grit carborundum paper. The crude protein powder was transferred to a vial and chloroform was added to float the protein powder away from the carborundum residues. Residual chloroform was allowed to evaporate overnight under ambient conditions. 2.19 mg of pregelled protein powder was added to 1.18 g of 20% (by weight) SELP8K batch 96072 solution. The actual weight-fraction protein for this solution was 20% (w/w), thus 0.24 g of protein was present. The addition of pregelled protein on a weight basis was calculated to be about 0.9% (by weight, based on protein content).

The behavior of SELP8K solutions was measured using modulated differential scanning calorimetry (MDSC) TA Instruments Modulated DSC, Model MDSC 2920. 20.4780 milligrams of a 33% (w/w) solution of SELP8K batch 95092 in 1×PBS was hermetically sealed inside of a 40 microliter aluminum pan. The amplitude and period of the sinusoidally applied heating function was 1.0° C. and 60 seconds, respectively. The experiment showed that, after an induction time, an exothermic peak occurred (FIG. 1). The exothermic peak (the lower trace in FIG. 1) was integrated using a software-adjusted baseline based on the change in heat capacity of the sample. The 18.90 $J \cdot g^{-1}$ peak integration corresponds to the entire mass of the sample which was 33% by weight protein polymer. Thus, the integration value was multiplied by a factor of 3 to adjust for that portion of the sample which was water. The corrected integration of the peak which takes into consideration only the mass of the polymer which caused the exotherm, was 56.70 $J \cdot g^{-1}$. This peak was consistent with the occurrence of a non-reversible crystallization event. Data gathered to date suggests that the viscosity build-up observed in solutions of various SELP polymers is due to crystallization of the protein chains, most likely, the silk-like blocks through a mechanism involving, at least in part, hydrogen bond formation.

Figure 2:
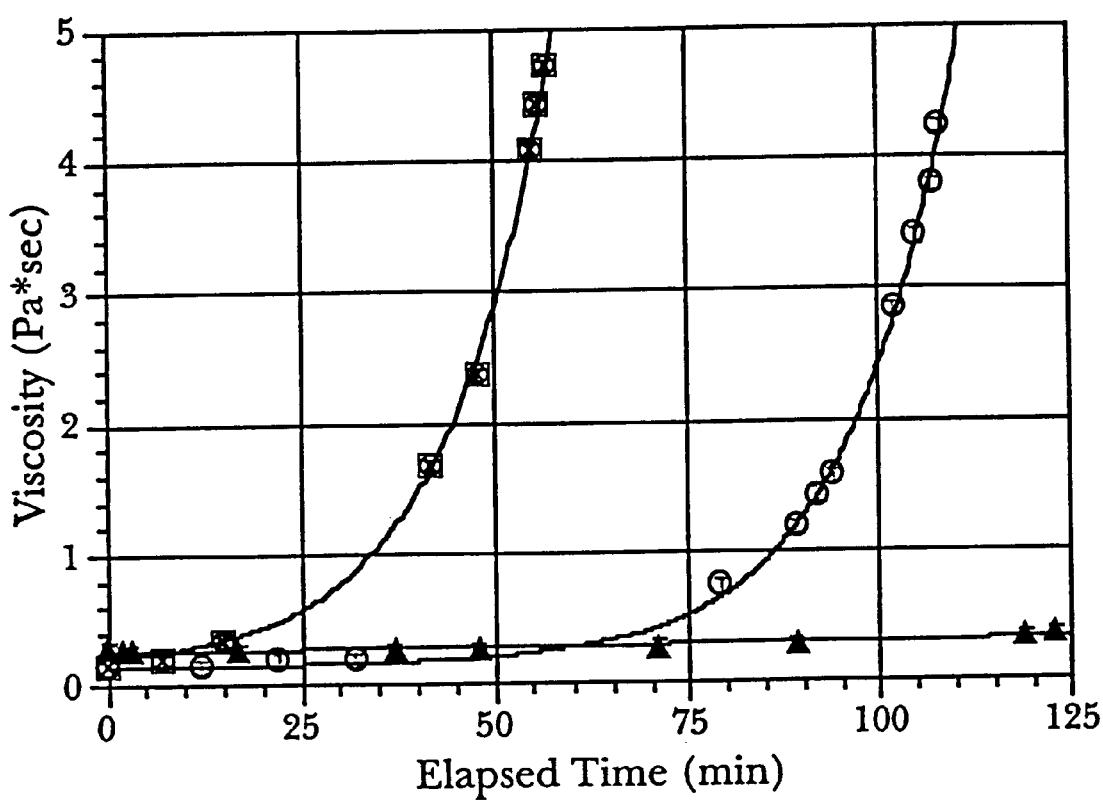
FIG. 2. Viscosity Versus Time of 20% (w/w) Solutions of SELP5, SELP8K and SELP0K. Presented is viscosity versus time of 20% (w/w) solutions of SELP5 (□), SELP8K (○), and SELP0K (▲) at 37° C.

The results of Brookfield viscometry experiments also add further validation that gelation of SELP solutions occurs and that the process might be controlled by adjusting conditions that affect crystallization. Three SELPs with varying amounts of silk-like blocks in their repeat units were chosen for this study. The experiments were performed isothermally at 37° C. The protein solutions were 20% (w/w) in 1×PBS and subjected to a steady shear rate of 40 $s^{-1}$. FIG. 2 shows that the viscosity build-up as a function of time ranked the polymers according to the number of silk-like blocks contained in their repeat units. SELP0K, which has only two silk blocks per repeat unit, demonstrated no rise in viscosity over the time period studied. SELP8K, which has 4 silk-like blocks per repeat unit, showed a delayed viscosity rise with time when compared to SELP5 which has 8 silk-like blocks per repeat unit.

Figure 3:
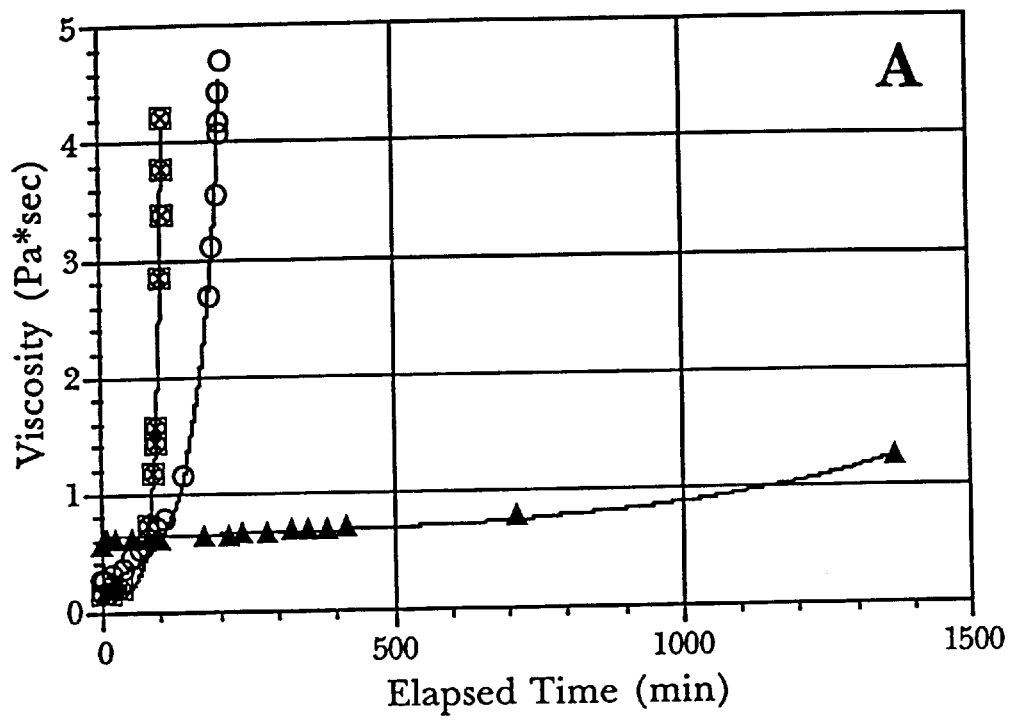
FIGS. 3A and 3B. Viscosity Versus Time of 20% (w/w) Solutions of SELP8K and SELP5 at Various Temperatures. A. Presented is viscosity versus time of 20% (w/w) solutions of SELP8K at 4° C. (▲), 23° C. (○) and 37° C. (□). B. Presented is viscosity versus time of 20% (w/w) solutions of SELP5 at 4° C. (▲), 23° C. (○) and 37° C. (□).
Figure 3:
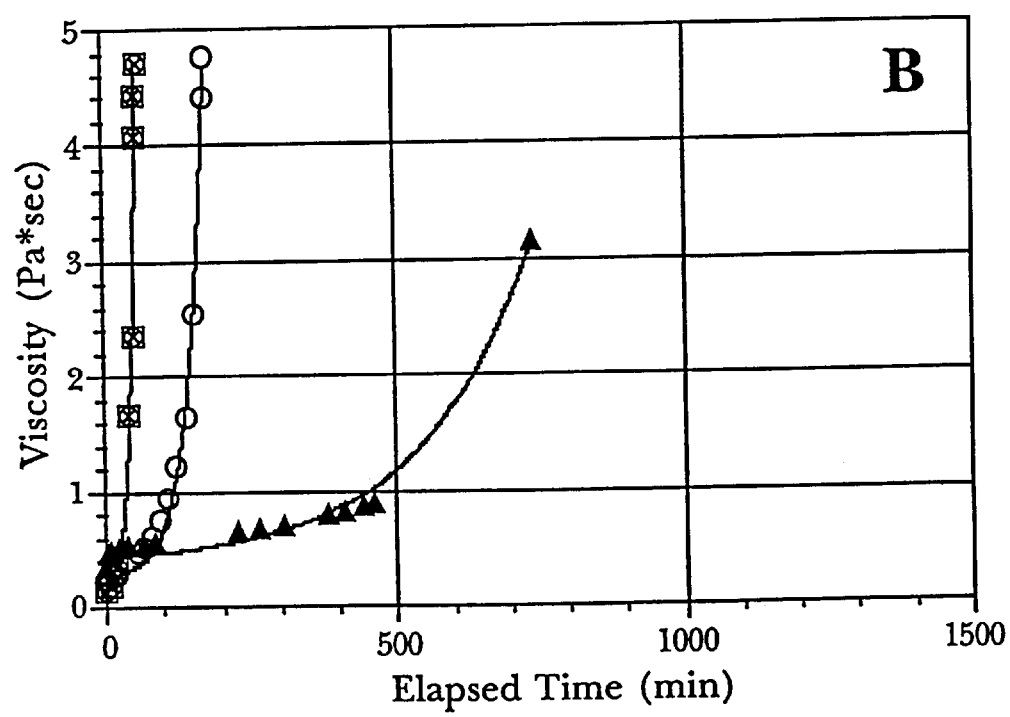

Further evidence of crystallization was obtained from examining the viscosity buildup of SELP solutions at various temperatures. FIGS. 3A and 3B show the viscosity results for 20% (w/w) solutions of SELP8K and SELP5, respectively. SELP5, which has more silk units than SELP8K, gelled faster than SELP8K at all temperatures.

Both graphs show that temperature dramatically affects the rate of gelation. Higher temperatures resulted in faster rates of gelation.

Figure 4:
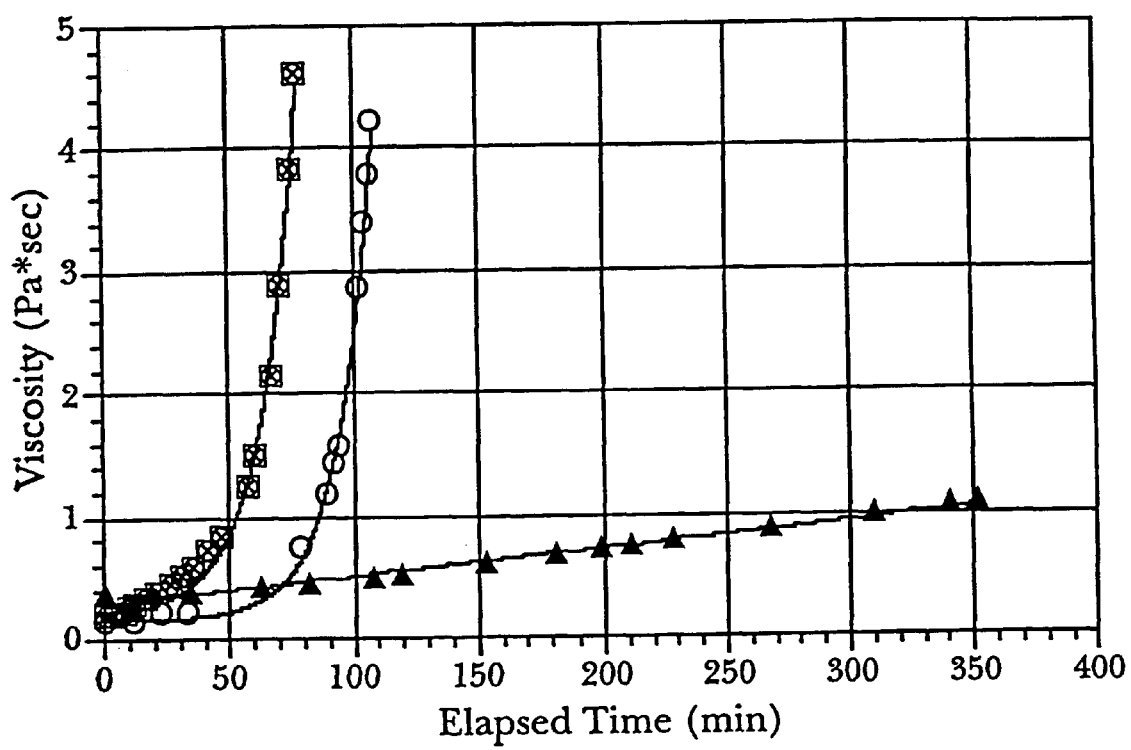
FIG. 4. Viscosity Versus Time of 20% (w/w) Solutions of SELP8K Containing Various Additives. Presented is viscosity versus time of 20% (w/w) solutions of SELP8K in 1×PBS (○), 1×PBS containing 6M urea (▲) and 1×PBS containing precrystallized SELP8K (□) at 37° C.

Additives which control the rate of crystallization of SELP polymer solutions were identified. Urea is known to denature proteins by disrupting and preventing the formation of hydrogen bonds. If crystallization is the mechanism by which SELP solutions gel, urea should retard or inhibit gelation. Additionally, crystallization is a process that can be accelerated by additives which serve to nucleate crystal formation. Precrystallized SELP incorporated into a fresh SELP solution is expected to act as a nucleating agent. FIG. 4 shows that the gelation of 20% (w/w) solutions of SELP8K at 37° C. was effectively accelerated by the addition of pregelled SELP8K protein, an expected nucleating agent, and virtually eliminated by the addition of urea, compared to the gelation rate of the control, SELP8K in 1×PBS. The slow increase in viscosity of the 6 M urea-containing solution was due to moisture loss during the experiment.

H. Example 7

Release of Compounds From SELP Gels

The release of compounds incorporated into SELP solutions that had been converted to gels at 37° C. was studied. SELP powder was dissolved in phosphate buffered saline (1×PBS, pH 7.4) at various concentrations and fluorescently labeled amino acids and dextrans of various molecular weights were added. The solutions were mixed and loaded into 0.5 and 1.0 cc plastic syringes and incubated at 37° C. Gel discs were excised from the syringes and placed in elution tubes with 5 ml of phosphate buffered saline containing 0.01% sodium azide (1×PBSA) and incubated at 37° C. At various times, the tubes were removed from the incubator, agitated by inversion and the eluate measured for fluorescence using a Sequoia and Turner fluorometer, model 450. Dansyl derivatives were read using excitation and emission filters NB360 and SC475, respectively. Fluorescein derivatives were read using excitation and emission filters NB490 and SC515. The tubes were replaced at 37° C. for further analysis. The loading amounts of each compound was adjusted such that 100% release would allow a fluorescent reading within the linear range of the instrument. The fluorescence remaining in the gel at termination was determined by dissolving the gel in 88% formic acid, neutralizing with sodium hydroxide, and diluting to a total volume of 5 ml with PBS containing 2 M Urea. Dansyl-L-glutamine (free acid, FW 379.4) and N(epsilon)-dansyl-L-lysine (free acid, FW 379.5) were obtained from Sigma Chemical, Co., St. Louis, Mo. Dextran, dansyl, 40,000 MW and 70,000 MW and dextran, fluorescein, 10,000 MW and 500,000 MW were obtained from Molecular Probes, Inc., Eugene, Oreg.

Figure 5:
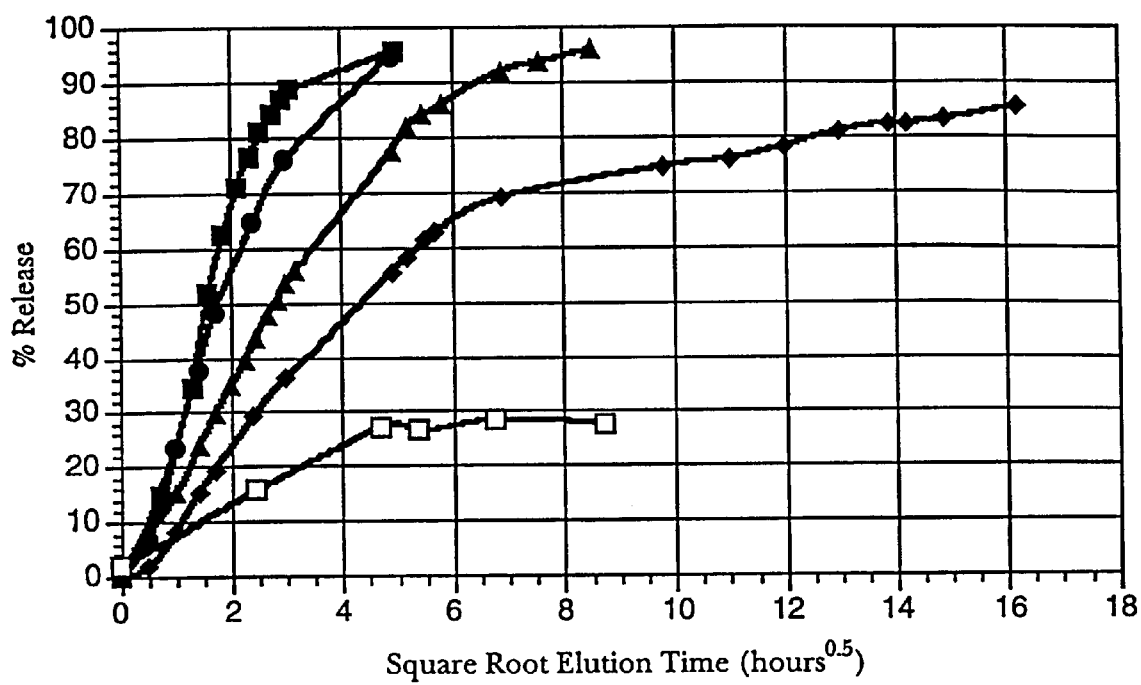
FIG. 5. Release of Various Molecular Weight Compounds From SELP8K Gels in 1×PBSA at 37° C. Presented is the release of various molecular weight compounds from SELP8K gels in 1×PBSA at 37° C. wherein (■) represents 20% (w/w) SELP8K containing 0.25% dansyl-lysine (mw 379.5), (●) represents 20% (w/w) SELP8K containing 0.004% fluorescein-dextran (mw 10,000), (▲) represents 20% (w/w) SELP8K containing 1% dansyl-dextran (mw 40,000), (♦) represents 20% (w/w) SELP8K containing 0.02% fluorescein-dextran (mw 500,000) and (□) represents 33% (w/w) SELP8K (mw 69,814).

FIG. 5 shows that compounds ranging in molecular weight from several hundred to 500,000 kD can be released from SELP gels at 37° C. in PBS. The amount of compound eluted is a linear function of the square root of time, indicitive of Fickian diffusion. The release of SELP protein from SELP gels was also monitored to determine the stability of the gelled matrix. Approximately 28% of the SELP protein in the gel was released in 24 hrs. After that time, the gel was stable in PBS at 37° C.

The consistency of the gel as observed by the release characteristics of added compounds is dependent on the concentration of SELP in solution prior to gelation. The time required to achieve 50% release of dansyl-glutamine (FW 379.4), dansyl-dextran (40 kDa), and fluorescein-dextran (500 kDa) from SELP gels containing 20%, 30% and 40% (w/w) SELP is shown in Table 10. Increasing the SELP concentration from 20% to 30% had no effect on the release of dansyl-glutamine and had little effect on the release of 40 kDa dansyl-dextran. However, an increase from 30% to 40% tripled the time required to achieve 50% release of 40 kDa dansyl-dextran. Increasing the SELP concentration from 20% to 30% almost tripled the time required to achieve 50% release of 500 kDa fluorescein-dextran, and increasing the SELP concentration from 30% to 40% increased its 50% release time more than 8-fold.

TABLE 10

Time Required For 50% Release of Fluorescent Compounds from SELP Gels

| SELP8K Concentration (w/w) | Dansyl-glutamine (MW 379.4) | Dansyl-dextran (40 kDa) | Fluorescein-dextran (500 kDa) |
|---|---|---|---|
| 20% | 2 hours | 5 hours | 12 hours |
| 30% | 1.5 hours | 6 hours | 34 hours |
| 40% | Not Determined | 18 hours | >288 hours |

Figure 6:
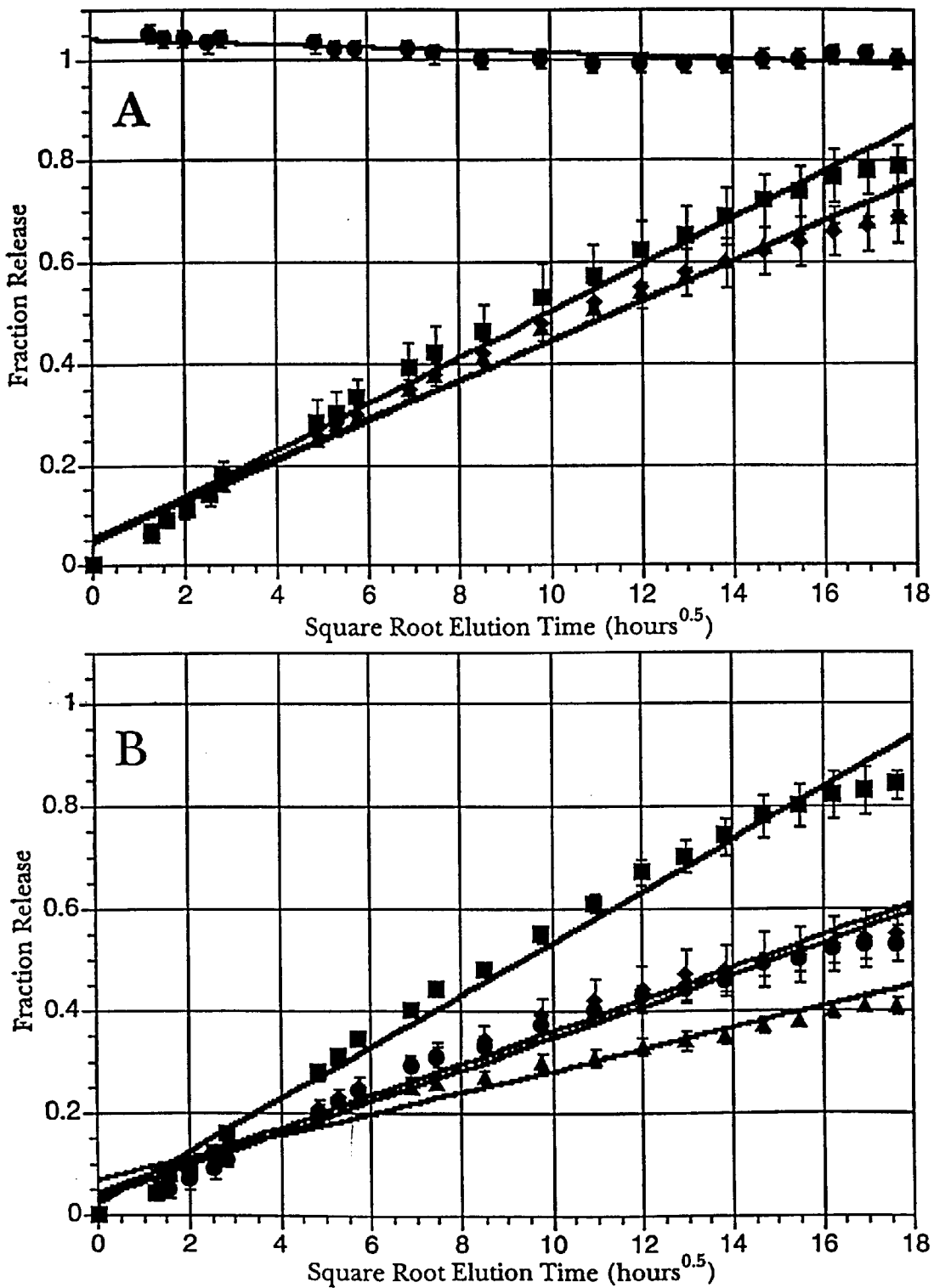
FIGS. 6A and 6B. Effect of SELP Composition on the Release of 70 Kd Dansyl-Dextran. A. Presented is the rate of release of 70 Kd dansyl-dextran from 20% (w/w) SELP8 (●), SELP9K (■), SELP5 (♦) and SELP8K (▲) gels incubated in 1×PBSA at 37° C. Error bars represent one standard deviation (n=3). B. Presented is the rate of release of 70 Kd dansyl-dextran from 40% (w/w) SELP8 (●), SELP9K (■), SELP5 (♦) and SELP8K (▲) gels incubated in 1×PBSA at 37° C. Error bars represent one standard deviation (n=3).

This effect is further illustrated in FIG. 6 where the release of 70 kda dansyl-dextran was studied as a function of SELP composition and concentration. The results show that at 20% (w/w) SELP8 did not gel and, therefore, it released its entire content of dansyl-dextran immediately into the elution medium. 20% SELP9K, SELP5 and SELP8K released 70 kda dansyl-dextran over 300 hrs with similar, first order release rates. At 40% (w/w), the release rate of dansyl-dextran from SELP9K gel was not changed over that of the 20% gel. 40% SELP8 and SELP5 gels gave identical release profiles and the release from the SELP5 gel at 40% was reduced by about 15% over that of the 20% gel. The release rate of 40% SELP8K gel was reduced by 40% over that of the SELP8K gel at 20%.

The timing of SELP gel formation and its effect on release rate was investigated in a mode that would approximate the use of a SELP solution containing a releasing compound injected into the body at 37° C. 0.2 grams of lyophilized SELP8K batch 96072 was dissolved in 0.675 ml 1×PBSA (50 mM sodium phosphate, pH 7.4, 100 mM sodium chloride, 0.01% sodium azide) and 0.125 ml of 20 mg/ml 70 kda dansyl-dextran in 1×PBS to make a 20% (w/w) solution of SELP8K. The solution was mixed several minutes until homogeneous and centrifuged for 3 min in a table top clinical centrifuge to clear entrapped bubbles. 0.1 ml of solution was dispensed into the bottom of glass 12×75 mm test tubes that had been prewarmed to 37° C. using a syringe and a 26 gauge needle. 5 ml of prewarmed (37° C.) 1×PBSA was immediately added to one tube and mixed by inversion. The SELP solution dispersed with no visible gel remaining on the tube. The remaining tubes were preincubated at 37° C. for various periods of time before 5 ml of prewarmed (37° C.) 1×PBSA was added. Preincubation times included 5, 45 min, 4.25 and 21 hrs. The release of fluorescent 70 kda dansyl-dextran into the elution medium was monitored as a function of time at 37° C. with time zero corresponding to the time that 1×PBSA was added to the tube.

The SELP8K solution was observed to have formed a solid gel that adhered to the bottom walls of the glass tube even after repeated mixing by inversion at even the shortest preincubation time (5 min). Preincubation time at 37° C. had no effect on release characteristics of 70 kDa dansyl-dextran. Prepared and dispensed in this manner, SELP8K solutions formed solid gels in less than 5 min at 37° C.

I. EXAMPLE 8

Compatibility and Release of a Protein Drug From SELP Gel rFGF-SAP is a genetically engineered mitotoxin produced by Prizm Pharmaceuticals, Inc., San Diego, Calif., called Pantarin (Casscells et al., *Proc. Natl. Acad. Sci. USA* 89:7159–7163 (1992) and Lappi and Baird, *Progress in Growth Factor Research* 2:223–236 (1990)). The protein is a recombinantly produced fusion of human basic fibroblast growth factor, bFGF, and the plant toxin, saporin. The product has been shown to significantly inhibit the proliferation of numerous FGF receptor expressing cell types including tumor cells and vascular smooth muscle cells in in vitro and in vivo systems. It would be of particular interest to deliver this product in vivo in a sustained, localized fashion to tissues that undergo pathological hyperproliferation.

Figure 7:
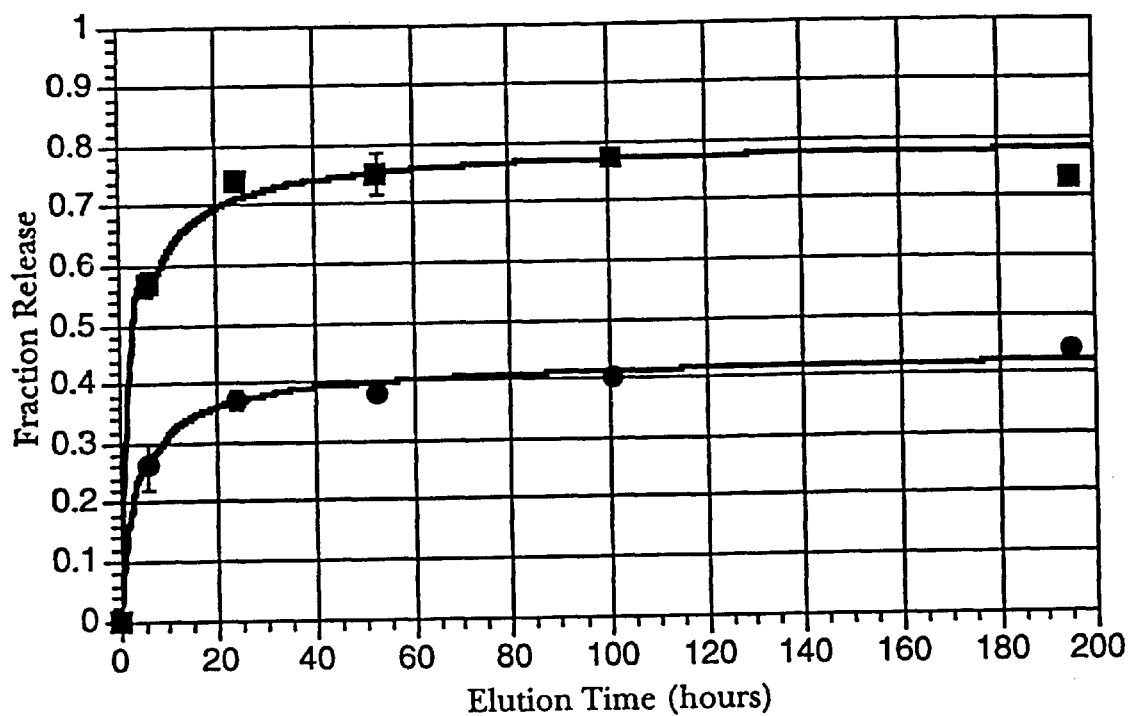
FIG. 7. Release of Pantarin at 37° C. from 33% (w/w) SELP8K Gels. Presented is the rate of release of Pantarin at 37° C. from 33% (w/w) SELP8K gels after a 4 hour (■) and a 24 hour (●) preincubation at 37° C. Error bars represent one standard deviation (n=3).

SELP8K gels were measured for controlled delivery of Pantarin. $^{125}$I-Pantarin was incorporated into 33% (w/w) SELP8K gel at an approximate loading concentration of 0.2 mg/ml using a buffer system previously shown to provide optimal stability to the structure and activity of Pantarin. The buffer composition was 50 mM sodium citrate, 80 mM NaCl, 0.1 mM EDTA, pH 6.0 (CBS). The gel was cast in a 0.5 cc hypodermic syringe at 37° C. Cylindrical sections of the gel were cut from the syringe and placed in elution tubes containing CBSGT buffer (CBS buffer containing 0.1% gelatin, 0.05% Tween-20) at 37° C. The radioactivity remaining in the gel specimens were monitored using a gamma counter. An initial rapid release of Pantarin in the first 24 hrs was followed by a slow, steady release of approximately 1% per day for at least 8 days (FIG. 7). The time allowed for gelation (preincubation time) of the SELP/Pantarin solution at 37° C. prior to initiation of elution affected the amount of Pantarin released in the initial phase. 56% and 26% Pantarin release was observed after 6 hrs of elution from 4 and 24 hr preincubated gels, respectively. At 24 hrs of elution, 74% and 37% of Pantarin was released, respectively.

The bioactivity of Pantarin released from 33% (w/w) SELP8K gels after 24 hrs at 37° C. was investigated using an in vitro bioactivity assay (McDonald et al., *Protein Expression and Purification* 8:97–108 (1996)). Control doses of fresh Pantarin or Pantarin eluted from SELP gel for 6 and 24 hrs at 37° C. were added to growing cells. The amount of Pantarin in the test sample was quantified by comparison to a dose response curve generated with a Pantarin reference standard. Control samples of Pantarin incubated in elution buffer for 6 and 24 hrs at 37° C. with no SELP gel were also included as controls. The results shown in Table 11 demonstrate that Pantarin was stable after being mixed with SELP, allowed to gel, and eluted from the gel at 37° C. for at least 24 hrs. Recovery of 70 to 82% of the bioactivity of the Pantarin contained in the SELP gel samples after 6 and 24 hrs of elution time is consistent with the release experiments which indicate that up to 70% of Pantarin could be released at 24 hrs.

TABLE 11

Bioactivity of Pantarin Released from SELP Gels

| Sample | Incubation Time or Elution Time at 37 C. | Pantarin Concentration Assayed (Average) | Expected Concentration if 100% Recovered | % of Expected Recovery |
|---|---|---|---|---|
| 33% SELP8K gel | 6 hours | 18.9 ug/ml (n = 6) | 27 ug/ml | 70% |
| Control Pantarin* | 6 hours | 136 ug/ml (n = 3) | 133 ug/ml | 102% |
| 33% SELP8K gel | 24 hours | 22.1 ug/ml (n = 6) | 27 ug/ml | 82% |

TABLE 11-continued

Bioactivity of Pantarin Released from SELP Gels

| Sample | Incubation Time or Elution Time at 37 C. | Pantarin Concentration Assayed (Average) | Expected Concentration if 100% Recovered | % of Expected Recovery |
|---|---|---|---|---|
| Control Pantarin* | 24 hours | 133 ug/ml (n = 3) | 133 ug/ml | 100% |
| Pantarin** | None | 124 ug/ml | 133 ug/ml | 93% |

*Incubated in elution buffer for 6 or 24 hours as indicated.
**Not incubated in elution buffer prior to assay.

J. Example 9

In Vivo Biocompatibility and Resorption of Injected SELP Gels

SELP8K batch 96072 solutions were produced at 20% (w/w) in cell culture grade PBS, filter sterilized through 0.22 $\mu$m syringe filters and loaded into 5 cc sterile plastic syringes. A syringe was mounted onto a programmable syringe pump (Cole Parmer). The tip of the syringe was adapted with approximately 8 inches of $\frac{1}{16}$ inch i.d. PTFE extension tubing to which Luer press fit syringe-to-tubing adaptors were attached. The other end of the tubing was fit with a disposable 30 gauge stainless steel hypodermic needle. 0.1 cc of SELP8K solution was injected into guinea pigs subcutaneously and intradermally (six injections per animal). Each 5 cc syringe of solution was used over the course of several hours at surgical room temperature through which time it remained fluid and injectable.

Under the skin of the injection sites, injected material converted to a firm mass momentarily after injection. The material did not migrate during the several hours of post-surgical inspection. No evidence of material migration was observed in any of the injection sites through one week of daily observations followed by weekly examinations.

Animals were sacrificed at 3, 7, and 28 days. The injection sites were excised, fixed, sectioned and stained with Hematoxylin/Eosin and Masson's Trichrome. The in vivo biocompatibility of SELP solutions was investigated by histological examination. No gross clinical signs of tissue reaction due to toxicity, allergy or irritancy were observed. Histologically, the injected material could be seen throughout the observation period in the tissues either interpenetrating the tissue collagen or isolated in subcutaneous pockets. In both cases, there was minimal evidence of acute inflammation. At 28 days, cells infiltrated the periphery of the gel and could be seen apparently resorbing the material. There were no signs of immunological reactivity. Occasionally, isolated portions of gel material located subcutaneously were observed at 28 days to be mildly encapsulated.

K. Example 10

Release of DNA From SELP Gels

20% (w/w) solutions of SELP8K and SELP9K were produced in TSAE buffer (50 mM Tris-HCl, pH 7.5, 0.9% sodium chloride, 0.02% sodium aside, 1 mM EDTA) in which DNA was dissolved. The DNA was a BanI REN digest of a purified *E. coli* plasmid that generated the following size fragments: 21, 114, 520, 1097, and 1374 bp. 0.5 mg of DNA was added to 100 mg of SELP solution to give a loading concentration of 0.5% (w/w). After mixing, the solutions were centrifuged for 2 min in a microfuge to collect them bubble-free in the bottom of 1.5 ml capped microfuge tubes. The solutions were incubated at 37° C. for either 1.5 hrs or 4 hrs prior to commencing elution experiments. The gels were overlayed with 0.1 ml of TSAE and incubated at 37° C. Periodically, the gels were centrifuged for 2 min in the microfuge and the elution buffer was collected and replaced with fresh buffer. Elution samples were applied to a 6% polyacrylamide gel cast and run in 1×TBE buffer and analyzed by electrophoresis and ethidium bromide staining to visualize the eluted DNA.

Figure 8:
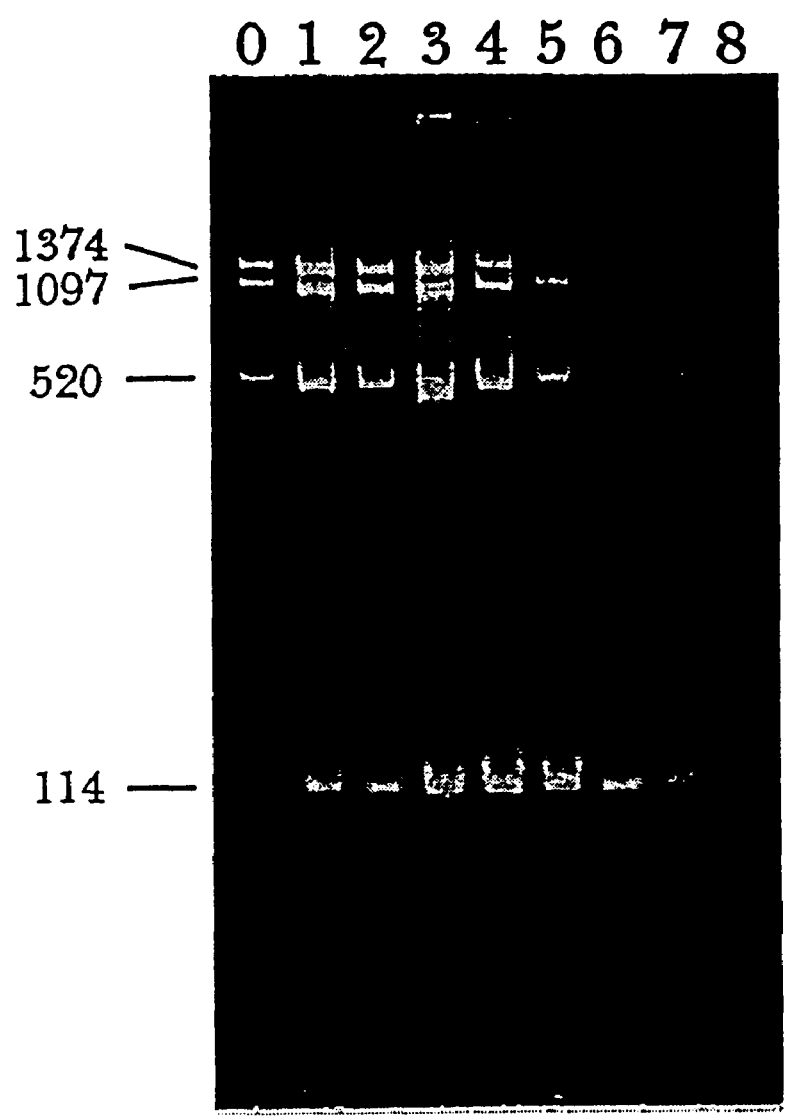
FIG. 8. DNA Release From SELP9K Gels. Presented is DNA release from SELP9K gels. BanII REN digested plasmid DNA containing fragment sizes of 1374, 1097, 520, and 114 bp was codissolved with SELP9K protein to yield a gel consisting of 20% (w/w) protein and 0.5% (w/w) DNA. Elutions were collected incrementally in TSAE buffer at 37° C. at specific time periods. Samples of the elution medium were analyzed by PAGE on a 6% polyacrylamide gel and stained with ethidium bromide. Lane 0, 0.5 ug of plasmid digest; lanes 1–8, 25 ul of elution medium collected from 0–2 hours, 2–4 hours, 4–24 hours, 24–48 hours, 48–72 hours, 96–120 hours, 120–144 hours and 144–168 hours, respectively. The sizes of the bands are given in bp.

DNA fragments were released from the SELP9K gel at a much greater rate than from the SELP8K. For the first 2 days, DNA bands of all sizes eluted according to their initial concentration in the DNA digest from the SELP9K gel (FIG. 8). After 6 days, elution of the 114 bp DNA fragment was rapidly diminishing while that of the larger fragments (520 bp and up) continued.

In order to examine the release of larger (gene size) fragments of DNA from SELP gels, an $^{35}$S-end-labeled lambda phage DNA digest containing 17 fragments ranging in size from 60 bp to 22,000 bp (Amersham, cat. No. SJ5000) was added to SELP5, SELP8K and SELP9K gels prepared as described above. In this case, 100 mg of each SELP solution was loaded with 3.9 $\mu$Ci of labeled DNA. The amount in weight of DNA was not known. The gels were allowed to set for 24 hrs at 37° C. before elution commenced. 0.1 cc of TSAE elution buffer was added to each gel, withdrawn and replaced with fresh elution buffer after specific incubation periods at 37° C. The samples were analyzed by PAGE using 3–10% gradient acrylamide gels, dried, and autoradiographed. The results indicate that throughout the 7 days of analysis DNA fragments up to 22,000 bp were released from the three SELP gels.

It is evident from the above results, that the subject compositions have particularly desirable properties for uses in implants, for tissue augmentation and for sustained release of bioactive compounds in vivo. By varying compositional ratios, the rate of resorption can be varied greatly, without significant changes in the tensile properties of polymer films. The compositions can be formed in a wide variety of devices or objects, to find extensive use for a variety of purposes and context as implants.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for altering the physical dimensions of a body tissue in a mammal, said method comprising:
   introducing into or onto said body tissue a composition comprising a liquid solution of a protein polymer of at least 15 kD which comprises alternating blocks of at least 2 units each of (a) an amino acid sequence of from about 3 to 30 amino acids which promotes protein crystallization and (b) an amino acid sequence element selected from the group consisting of an elastin-like element, a collagen-like element or a keratin-like element;
   wherein after said introducing step said protein polymer acquires a non-liquid form under physiological conditions in less than about 500 minutes,
   and wherein said protein polymer solution is capable of acquiring a non-liquid form without chemical crosslinking.

2. The method according to claim 1, wherein said amino acid sequence which promotes protein crystallization is GAGAGS (SEQ ID NO:1) or SGAGAG (SEQ ID NO:2).

3. The method according to claim 1, wherein said amino acid sequence element (b) is the amino acid sequence VPGG (SEQ ID NO:3), APGVGV (SEQ ID NO:4), GXGVP (SEQ ID NO:5) or VPGXG (SEQ ID NO:6), where X is valine, lysine, histidine, glutamic acid, arginine, aspartic acid, serine, tryptophan, tyrosine, phenylalanine, leucine, glutamine, asparagine, cysteine or methionine.

4. The method according to claim 3, wherein amino acid X is valine or lysine.

5. The method according to claim 1, wherein the step of introducing comprises injecting said composition in liquid form which acquires a non-liquid form subsequent to injection.

6. The method according to claim 1, wherein said protein polymer is about 10% (w/w) to about 50% (w/w) of said composition.

7. The method according to claim 2, wherein said amino acid sequence GAGAGS or SGAGAG is repeated from 2 to 16 times per alternating block.

8. The method according to claim 1, wherein said protein polymer comprises an amino acid sequence selected from the group consisting of:
   (a) $[(VPGVG)_8(GAGAGS)_8]_{12}$ (SEQ ID NO:29);
   (b) $[(VPGVG)_{12}(GAGAGS)_8]_9$ (SEQ ID NO:30);
   (c) $[(VPGVG)_{16}(GAGAGS)_8]_8$ (SEQ ID NO:31);
   (d) $[(VPGVG)_{32}(GAGAGS)_8]_5$ (SEQ ID NO:32);
   (e) $[(VPGVG)_8(GAGAGS)_6]_{13}$ (SEQ ID NO:28);
   (f) $[(VPGVG)_8(GAGAGS)_4]_{13}$; (SEQ ID NO:27)
   (g) $[(GVGVP)_4 \; GKGVP \; (GVGVP)_3 \; (GAGAGS)_4]_{12}$ (SEQ ID NO:35); and
   (h) $[GAGAGS \; (GVGVP)_4 \; GKGVP \; (GVGVP)_3 \; (GAGAGS)_2]_{12}$ (SEQ ID NO:36).

9. The method according to claim 1, wherein said composition further comprises a biologically active substance.

10. The method according to claim 1, wherein said protein polymer consists of the amino acid sequence MDPVVLQRRDWENPGVTQLNRL AAHPPFASDPMGAGSGAGAGS $[(GVGVP)_8 \; (GAGAGS)_4]_{12} \; (GVGVP)_8 \; (GAGAGS)_2$ GAGAMDPGRYQLSAGRYHYQLVWCQK (SEQ ID NO:19).

* * * * *

UNITED STATES PATENT AND TRADEMARK OFFICE
CERTIFICATE OF CORRECTION

PATENT NO. : 6,380,154
DATED : April 30, 2002
INVENTOR(S) : Joseph Capello and Erwin R. Stedronsky It is certified that error appears in the above-identified patent and that said Letters Patent is hereby corrected as shown below:

Column 1,
Line 5, after the title "SYNTHETIC PROTEINS FOR IN VIVO DRUG DELIVERY AND TISSUE AUGMENTATION", insert the following paragraph:

-- CROSS-REFERENCE TO RELATED APPLICATIONS
This application is a continuation-in-part of U.S. application Serial No. 08/212,237, filed March 11, 1994, now patent 5,606,019. --

Signed and Sealed this

Eleventh Day of June, 2002

*Attest:*

JAMES E. ROGAN
*Director of the United States Patent and Trademark Office*

*Attesting Officer*